(12) United States Patent
Schneider et al.

(10) Patent No.: US 7,211,376 B2
(45) Date of Patent: May 1, 2007

(54) POLYPEPTIDE FINGERPRINTING METHODS

(75) Inventors: Luke V. Schneider, Half Moon Bay, CA (US); Michael P. Hall, San Carlos, CA (US); Robert Petesch, Newark, CA (US); Jeffrey N. Peterson, Foster City, CA (US)

(73) Assignee: Target Discovery, Inc., Palo Alto, CA (US)

( * ) Notice: Subject to any disclaimer, the term of this patent is extended or adjusted under 35 U.S.C. 154(b) by 101 days.

(21) Appl. No.: 10/721,047

(22) Filed: Nov. 21, 2003

(65) Prior Publication Data
US 2005/0089930 A1    Apr. 28, 2005

Related U.S. Application Data

(62) Division of application No. 09/513,907, filed on Feb. 25, 2000, now Pat. No. 6,677,114.

(60) Provisional application No. 60/130,238, filed on Apr. 20, 1999.

(51) Int. Cl.
| | |
|---|---|
| C12Q 1/00 | (2006.01) |
| G01N 33/00 | (2006.01) |
| G01N 24/00 | (2006.01) |
| G01N 1/00 | (2006.01) |

(52) U.S. Cl. .................. 435/4; 435/6; 436/86; 436/87; 436/173; 436/175

(58) Field of Classification Search ..................... None
See application file for complete search history.

(56) References Cited

U.S. PATENT DOCUMENTS

| | | | |
|---|---|---|---|
| 4,842,701 A | 6/1989 | Smith et al. | |
| 4,994,165 A | 2/1991 | Lee et al. | |
| 5,306,412 A | 4/1994 | Whitehouse et al. | |
| 5,505,832 A | 4/1996 | Laukien et al. | |
| 5,856,082 A | 1/1999 | Aebersold et al. | |
| 5,872,010 A | 2/1999 | Karger et al. | |
| 5,985,121 A | 11/1999 | Wu et al. | |
| 6,393,367 B1 * | 5/2002 | Tang et al. | ................... 702/19 |

OTHER PUBLICATIONS

Mann and Wilm, "Error-Tolerant Identification of Peptides in Sequence Databases by Peptide Sequence Tags", *Anal. Chem.*, 66:(24) 4390-4399 (Dec. 15, 1994).

Wu, et al., "Fluorescence imaging detection for capillary isoelectric focusing," *Electrophoresis*, 16(8):1474-1478 (1995).

Jensen et al., "Sequence patterns produced by incomplete enzymatic digestion or one-step Edman degradation of peptide mixtures as probes for protein database searches", *Electrophoresis*, 17:938-944 (1996).

Wilkins et al., "Protein identification with sequence tags", *Current Biology*, 6(12):1543-1544 (1996).

(Continued)

*Primary Examiner*—Young J. Kim
(74) *Attorney, Agent, or Firm*—Townsend and Townsend and Crew LLP

(57) ABSTRACT

The invention provides methods, compositions, apparatus, and a computer data retrieval system for conducting proteomics.

9 Claims, 29 Drawing Sheets

OTHER PUBLICATIONS

Wilkins et al., "Rapid Protein Identification Using N-Terminal "Sequence Tag" and Amonio Acid Analysis", *Biochemical and Biophysical Research Communications*, 221:609-613, (1996) Article No. 0643.

Neubauer, et al., "Identification of the proteins of the yeast U1 small nuclear ribonucleoprotein complex by mass spectrometry," *Proc. Natl. Acad. Sci. USA*, 94:385-390 (1997).

Tang, et al., Two-dimensional analysis of recombinant *E. coli* proteins using capillary isoelectric focusing Electrospray ionization mass spectrometry, *Analytical Chemistry*, 69:3177-3182 (1997).

Wilkins et al., "Proteins Identification with N and C-Terminal Sequence Tags in Proteome Projects", *J. Mol. Biol.*, 278: 599-608 (1998).

Li, G., et al., "Improvements on sample handling for rapid mass spectrometric identification of proteins resolved by 2D gel electrophoresis," *Book of Abstracts*, 213th ACS National Meeting, San Francisco, pp. 13-17 (Apr. 1997).

Escoubas, et al., "Multidimensional peptide fingerprinting by high performance liquid chromatography, capillary zone electrophoresis and matrix-assisted laser desorption/ionization . . . " *Rapid Communications in Mass Spec.*, 12(16):1075-1084 (1998).

* cited by examiner

SEQUENCE LISTING

<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: 1425.7 Da peptide

<400> SEQUENCE: 1

His Ser Asp Ala Val Phe Thr Asp Asn Tyr Thr Arg
1               5                   10

```
<210> SEQ ID NO 2
<211> LENGTH: 6
<212> TYPE: PRT
<213> ORGANISM: Artificial Sequence
<220> FEATURE:
<223> OTHER INFORMATION: N-terminal amino acid sequence of rabbit
      glycogen phosphorylase A

<400> SEQUENCE: 2

Ser Arg Pro Leu Ser Asp
 1               5

<210> SEQ ID NO 3
<211> LENGTH: 4
<212> TYPE: PRT
<213> ORGANISM: Artificial Sequence
<220> FEATURE:
<223> OTHER INFORMATION: N-terminal amino acid sequence of human
      bradykinin

<400> SEQUENCE: 3

Arg Pro Pro Gly
 1

<210> SEQ ID NO 4
<211> LENGTH: 5
<212> TYPE: PRT
<213> ORGANISM: Artificial Sequence
<220> FEATURE:
<223> OTHER INFORMATION: N-terminal amino acid sequence of human
      bradykinin

<400> SEQUENCE: 4

Arg Pro Pro Gly Phe
 1               5

<210> SEQ ID NO 5
<211> LENGTH: 6
<212> TYPE: PRT
<213> ORGANISM: Artificial Sequence
<220> FEATURE:
<223> OTHER INFORMATION: N-terminal amino acid sequence of human
      bradykinin

<400> SEQUENCE: 5

Arg Pro Pro Gly Phe Ser
 1               5

<210> SEQ ID NO 6
<211> LENGTH: 7
<212> TYPE: PRT
<213> ORGANISM: Artificial Sequence
<220> FEATURE:
<223> OTHER INFORMATION: N-terminal amino acid sequence of rabbit
      glycogen phosphorylase A
<220> FEATURE:
<221> NAME/KEY: MOD_RES
<222> LOCATION: (1)...(1)
<223> OTHER INFORMATION: Xaa = acetyl-Ser

<400> SEQUENCE: 6

Xaa Arg Pro Ser Leu Asp Gln
 1               5

<210> SEQ ID NO 7
<211> LENGTH: 9
<212> TYPE: PRT
<213> ORGANISM: Artificial Sequence
<220> FEATURE:
```

```
<223> OTHER INFORMATION: PITC-labeled bradykinin
<220> FEATURE:
<221> NAME/KEY: MOD_RES
<222> LOCATION: (1)...(1)
<223> OTHER INFORMATION: Xaa = Arg modified by phenylisothiocyanate
      (PITC)

<400> SEQUENCE: 7

Xaa Pro Pro Gly Phe Ser Pro Phe Arg
 1               5

<210> SEQ ID NO 8
<211> LENGTH: 9
<212> TYPE: PRT
<213> ORGANISM: Artificial Sequence
<220> FEATURE:
<223> OTHER INFORMATION: IMB-labeled bradykinin
<220> FEATURE:
<221> NAME/KEY: MOD_RES
<222> LOCATION: (1)...(1)
<223> OTHER INFORMATION: Xaa = arginine modified by iminobiotin (IMB)

<400> SEQUENCE: 8

Xaa Pro Pro Gly Phe Ser Pro Phe Arg
 1               5

<210> SEQ ID NO 9
<211> LENGTH: 5
<212> TYPE: PRT
<213> ORGANISM: Artificial Sequence
<220> FEATURE:
<223> OTHER INFORMATION: SPITC-labeled horse apomyoglobin peptide
<220> FEATURE:
<221> NAME/KEY: MOD_RES
<222> LOCATION: (1)...(1)
<223> OTHER INFORMATION: Xaa = Gly modified by
      4-sulfophenylisothiocyanate (SPITC)

<400> SEQUENCE: 9

Xaa Leu Ser Asp Gly
 1               5

<210> SEQ ID NO 10
<211> LENGTH: 9
<212> TYPE: PRT
<213> ORGANISM: Artificial Sequence
<220> FEATURE:
<223> OTHER INFORMATION: C-terminal 2-AETA-labeled bradykinin
<220> FEATURE:
<221> NAME/KEY: MOD_RES
<222> LOCATION: (9)...(9)
<223> OTHER INFORMATION: Xaa = Arg modified by
      (2-aminoethyl)trimethylammonium

<400> SEQUENCE: 10

Arg Pro Pro Gly Phe Ser Pro Phe Xaa
 1               5

<210> SEQ ID NO 11
<211> LENGTH: 6
<212> TYPE: PRT
<213> ORGANISM: Artificial Sequence
<220> FEATURE:
<223> OTHER INFORMATION: N-terminal amino acid sequence of rabbit
      glycogen phosphorylase A
```

```
-continued

<220> FEATURE:
<221> NAME/KEY: MOD_RES
<222> LOCATION: (1)...(1)
<223> OTHER INFORMATION: Xaa = acetyl-Ser

<400> SEQUENCE: 11

Xaa Arg Pro Leu Ser Asp
 1               5
```

POLYPEPTIDE FINGERPRINTING METHODS

CROSS-REFERENCES TO RELATED APPLICATIONS

This application is a division of U.S. patent application Ser. No. 09/513,907, filed on Feb. 25, 2000, now U.S. Pat. No. 6,677,114 which claims priority to U.S. Provisional Application Ser. No. 60/130,238, filed on Apr. 20, 1999. U.S. patent application Ser. No. 09/513,907 is also related to U.S. Provisional Patent Application 60/075,715, filed on Feb. 24, 1998, U.S. patent application Ser. No. 09/513,486 (now U.S. Pat. No. 6,537,432), filed on Feb. 25, 2000, and U.S. patent application Ser. No. 09/513,395 (now U.S. Pat. No. 6,379,971) filed on Feb. 25, 2000. All of these applications are herein incorporated by reference in their entirety for all purposes.

FIELD OF THE INVENTION

This invention relates to the field of protein separation and proteomics.

BACKGROUND OF THE INVENTION

A goal of genomics research and differential gene expression analysis is to develop correlations between gene expression and particular cellular states (e.g., disease states, particular developmental stages, states resulting from exposure to certain environmental stimuli and states associated with therapeutic treatments). Such correlations have the potential to provide significant insight into the mechanism of disease, cellular development and differentiation, as well as in the identification of new therapeutics, drug targets, and disease markers. Correlations of patterns of gene expression can also be used to provide similar insights into disease and organism metabolism that can be used to speed the development of agricultural products, transgenic species, and for metabolic engineering of organisms to increase bioproduct yields or desirable metabolic activities.

Many functional genomic studies focus on changes in mRNA levels as being indicative of a cellular response to a particular condition or state. Recent research, however, has demonstrated that often there is a poor correlation between gene expression as measured by mRNA levels and actual active gene product formed (i.e., protein encoded by the mRNA). [4] This finding is not surprising since many factors—including differences in translational efficiency, turnover rates, extracellular expression or compartmentalization, and post-translational modification—affect protein levels independently of transcriptional controls. Thus, the evidence indicates that functional genomics is best accomplished by measuring actual protein levels (i.e., utilizing proteomic methods) rather than with nucleic acid based methods. The successful use of proteins for functional genomic analyses, however, requires reproducible quantification and identification of individual proteins expressed in cell or tissue samples.

It is at the protein level that metabolic control is exercised in cells and tissues. Comparison of the levels of protein expression between healthy and diseased tissues, or between pathogenic and nonpathogenic microbial strains, can speed the discovery and development of new drug compounds or agricultural products. Analysis of the protein expression pattern in diseased tissues or in tissues excised from organisms undergoing treatment can also serve as diagnostics of disease states or the efficacy of treatment strategies, as well as provide prognostic information regarding suitable treatment modalities and therapeutic options for individual patients.

Many proteins are expressed at varying levels in different cells. Proteins extracted from tissue or cell samples, using conventional techniques, must first be separated into individual proteins by gel or capillary electrophoresis or affinity techniques, before the individual proteins levels can be compared both within a sample and across samples obtained from different tissue sources. Because of the number of proteins expressed by a cell at any given time, multiple electrophoretic techniques (e.g., isoelectric focussing followed by electroporation through a polyacrylamide gel) are often applied to isolate all the individual proteins contained in a given sample.

Several techniques have been used to quantify the relative amounts of each protein present after the separation, including: staining proteins separated in a polyacrylamide gel with dyes (e.g., Brilliant Blue and Fast Green), with colloidial metals (e.g., gold or silver staining), or by prior labelling of the proteins during cellular synthesis by the addition of radioactive compounds (e.g., with 35S-methionine or 14C-amino acids, or 3H-leucine). Staining techniques yield poorly quantitative results because varying amounts of stain are incorporated into each protein and the stained protein must be resolved against the stained background of the gel or electroblotting substrate. Since radioactive labels are applied only to the proteins prior to separation, they overcome the background problem of staining techniques. However, feeding radioactive compounds to human subjects or handling radioactive materials in an uncontrolled field environment (e.g., crop plants) restricts the usefulness of this approach. Both staining and radiolabelling techniques also require inordinately long times to achieve detection. Staining and destaining of gels is a diffusion limited process requiring hours. Radiolabels must be quantified by exposing the labelled gel to photographic film or a phosphor screen for several hours to days while waiting for the radioactive decay process to produce a quantitative image. Direct infrared spectrophotometric interrogation of the proteins in a gel has also been used previously as a method for providing quantitative protein expression data. However, this quantitative resolution possible from this approach is adversely affected by variations in gel thickness and differential spreading of the protein spot between gels (changing the local concentration). Furthermore, the comparatively low absorption cross-section of proteins in the infrared limits the detection sensitivity. Analysis of the protein expression pattern does not provide sufficient information for many applications.

Several methods have also been proposed for the identification of proteins once they are resolved. The most common methods involve referencing the separation coordinates of individual proteins (e.g., isoelectric point and apparent molecular weight) to those obtained from archived separation coordinate data (e.g., annotated 2-D gel image databases) or control samples, performing a chemilytic or enzymatic digestion of a protein coupled with determination of the mass of the resulting peptide fragments and correlating this peptide mass fingerprint with that predicted to arise from the predicted genetic sequence of a set of known proteins (see James, P., M. Quandroni, E. Carafoli, and G. Gonnet, *Biochem. Biophys. Res. Commun.,* 195:58–64 (1993); Yates, J. R., S. Speicher, P. R. Griffin, and T. Hunkapiller, *Anal. Biochem.,* 214:397–408 (1993)), the generation of a partial protein sequence that is compared to the predicted sequences obtained from a genomic database (see Mann, M., paper presented at the IBC Proteomics conference, Boston, Mass. (Nov. 10–11, 1997); Wilm, M., A. Shevchenko, T. Houthaeve, S. Breit, L. Schweiger, T. Fotsis and M. Mann, *Nature,* 379:466–469 (1996); Chait, B. T, R. Wang, R. C. Beavis and S. B. H. Kent, *Science,* 262:89–92 (1993)), or combinations of these methods (see Mann, M., paper presented at the IBC Proteomics conference, Boston, Mass. (Nov. 10–11, 1997); Wilm, M., A. Shevchenko, T. Houthaeve, S. Breit, L. Schweiger, T. Fotsis and M. Mann, *Nature,* 379:466–469 (1996); Chait, B. T, R. Wang, R. C. Beavis and S. B. H. Kent, *Science,* 262:89–92 (1993)). Recent work indicates that proteins can only be unambiguously identified through the determination of a partial sequence, called a protein sequence tag (PST), that allows reference to the theoretical sequences determined from genomic databases (see Clauser, K. R., S. C. Hall, D. M. Smith, J. W. Webb, L. E. Andrews, H. M. Tran, L. B. Epstein, and A. L. Burlingame, "Proc. Natl. Acad. Sci. (USA), 92:5072–5076 (1995); Li, G., M. Walthan, N. L. Anderson, E. Unworth, A. Treston and J. N. Weinstein, *Electrophoresis,* 18:391–402 (1997)). However, between 8 to 18 hours is currently required to generate a PST for a single protein sample by conventional techniques, with a substantial fraction of this time devoted to recovery of the protein sample from the separation method in a form suitable for subsequent sequencing (see Shevchenko, A., et al., *Proc. Natl. Acad. Sci.* (*USA*), 93:14440–14445 (1996); Mark, J., paper presented at the PE/Sciex Seminar Series, Protein Characterization and Proteomics: Automated high throughput technologies for drug discovery, Foster City, Calif. (March, 1998). This makes the identification of all separated proteins from a tissue a time and cost prohibitive endeavor. This has restricted more widespread use of proteomic methods, despite their advantages for functional genomics and inhibited the development of proteomic databases, analogous to the genome databases now available (e.g., Genbank and the Genome Sequence Database).

Thus, current methods for identifying and quantitating the protein expression patterns ("protein fingerprints") of cells, tissues, and organs are lacking sufficient resolution, precision, and/or sensitivity. The present invention addresses these features lacking in the methods known in the art.

Polypeptide Separation Methods: Capillary Electrophoresis

Two-dimensional (2-D) gel electrophoresis is currently the most widely adopted method for separating individual proteins isolated from cell or tissue samples [5, 6, 7]. Evidence for this is seen in the proliferation (more than 20) of protein gel image databases, such as the Protein-Disease Database maintained by the NIH [8]. These databases provide images of reference 2-D gels to assist in the identification of proteins in gels prepared from various tissues.

Capillary electrophoresis (CE) is a different type of electrophoresis, and involves resolving components in a mixture within a capillary to which an electric field is applied. The capillary used to conduct electrophoresis is filled with an electrolyte and a sample introduced into one end of the capillary using various methods such as hydrodynamic pressure, electroosmotically-induced flow, and electrokinetic transport. The ends of the capillary are then placed in contact with an anode solution and a cathode solution and a voltage applied across the capillary. Positively charged ions are attracted towards the cathode, whereas negatively charged ions are attracted to the anode. Species with the highest mobility travel the fastest through the capillary matrix. However, the order of elution of each species, and even from which end of the capillary a species elutes, depends on its apparent mobility. Apparent mobility is the sum of a species electrophoretic mobility in the electrophoretic matrix and the mobility of the electrophoretic matrix itself relative to the capillary. The electrophoretic matrix may be mobilized by hydrodynamic pressure gradients across the capillary or by electroosmotically-induced flow (electrosomotic flow).

A number of different electrophoretic methods exist. Capillary isoelectric focusing (CIEF) involves separating analytes such as proteins within a pH gradient according to their isoelectric point (i.e., the pH at which the analyte has no net charge) of the analytes. A second method, capillary zone electrophoresis (CZE) fractionates analytes on the basis of their intrinsic charge-to-mass ratio. Capillary gel electrophoresis (CGE) is designed to separate proteins according to their molecular weight. (For reviews of electrophoresis generally, and CIEF and CZE specifically, see, e.g., Palmieri, R. and Nolan, J. A., "Protein Capillary Electrophoresis: Theoretical and Experimental Considerations for Methods Development," in *CRC Handbook of Capillary Electrophoresis: A Practical Approach,* CRC Press, chapter 13, pp. 325–368 (1994) (electrophoresis generally); Kilar, F., "Isoelectric Focusing in Capillaries," in *CRC Handbook of Capillary Electrophoresis: A Practical Approach,* CRC Press, chapter 4, pp. 325–368 (1994); and McCormick, R. M., "Capillary Zone Electrophoresis of Peptides," in *CRC Handbook of Capillary Electrophoresis: A Practical Approach,* CRC Press, chapter 12, pp. 287–323 (1994). All of these references are incorporated by reference in their entirety for all purposes).

While 2-D gel electrophoresis is widely practiced, several limitations restrict its utility in functional genomics research. First, because 2-D gels are limited to spatial resolution, it is difficult to resolve the large number of proteins that are expressed in the average cell (1000 to 10,000 proteins). High abundance proteins can distort carrier ampholyte gradients in capillary isoelectric focusing electrophoresis and result in crowding in the gel matrix of size sieving electrophoretic methods (e.g., the second dimension of 2-D gel electrophoresis and CGE), thus causing irreproducibility in the spatial pattern of resolved proteins [20, 21 and 22]. High abundance proteins can also precipitate in a gel and cause streaking of fractionated proteins [20]. Variations in the cross-linking density and electric field strength in cast gels can further distort the spatial pattern of resolved proteins [23, 24]. Another problem is the inability to resolve low abundance proteins neighboring high abundance proteins in a gel because of the high staining background and limited dynamic range of gel staining and imaging techniques [25, 22]. Limitations with staining also make it difficult to obtain reproducible and quantifiable protein concentration values. In some recent experiments, for example, investigators were only able to match 62% of test spots of the spots formed on 37 gels run under similar conditions [21; see also 28, 29]. Additionally, many proteins are not soluble in buffers compatible with acrylamide gels, or fail to enter the gel efficiently because of their high molecular weight [26, 27].

Thus, currently used methods of capillary electrophoresis provide significant limitations with regard to their usefulness is providing a detailed protein expression fingerprint of a cell or tissue sample.

Protein Species Identification/Protein Sequence Tags

In contrast to characterizing proteins on the basis of their electrophoretic mobility or isoelectric point, an approach to identifying the protein species that are expressed in a tissue or cell sample is to obtain partial or complete peptide sequence information from proteins purified from the sample. Needless to say, but this approach is laborious and is of limited-sensitivity as it requires extensive and often problematic purification steps to isolate individual protein species to allow for unambiguous sequence determination, and in many cases is simply not feasible for proteins which are not highly abundant and/or are not readily purifiable free from contaminant protein species.

It is also important that primary amino acid sequence or a partial sequence (i.e., a protein sequence tag, "PST") be determined so that the reason underlying changes in the protein expression pattern related to proteins that appearing at different separation coordinates, can be determined. Proteins may appear at more than one separation coordinate, depending on the degree of post-translational modification exercised on that protein by the cell or tissue. The separation coordinate for a protein may also change due to genetic mutations. Changes in the relative abundance of a protein at any given separation coordinate may also be due to changes in the regulation of gene expression. Only by unambiguously identifying each of the proteins resolved can the reason underlying any variations in protein expression across different samples be deduced.

Several methods have previously been proposed for determining the sequence or a protein sequence tag of separated proteins. These include: sequential rounds of N-terminal or C-terminal labeling followed by liberation and determination of the labeled amino acid, exoproteolytic digestion of the protein one amino acid at a time, endoproteolytic digestion of larger proteins into smaller peptides followed by N- and C-terminal labeling and amino acid determination, and mass spectrometric fragmentation pattern recognition. Sequential labeling and digestion techniques (e.g., Edman chemistry) are time consuming, even when automated, because the process must be repeated through many cycles before a sufficiently large protein sequence tag can be accumulated. Propagation of errors-i.e., either from incomplete labeling on each round, incomplete liberation of the labeled amino acid, or both-also limits the length of protein sequence that can be determined using these techniques. While a more complete protein sequence can be obtained by first using endoproteases to cleave the protein into smaller fragments prior to application of the sequential labeling and digestion chemistry, this also introduces the time and labor intensive step of reseparating and purifying the protein fragments, usually by reapplication of an electrophoretic separation technique. Determining the sequence order of these peptide fragments in the original protein can also present additional problems. Carboxy-terminal methoxy labeling of cyanogen bromide digests has been used to identify the C-terminal peptide fragment from other fragments formed by cyanogen bromide digestion of a larger protein.

Protein Sequence Determination By Mass Spectrometry

Mass spectrometric techniques are increasingly being applied to protein identification because of their speed advantage over the more traditional methods. Electrospray and matrix assisted laser desorption ionization (MALDI) are the most common mass spectrometric techniques applied to protein analysis because they are best able to ionize large, low volatility, molecular species. Two basic strategies have been proposed for the MS identification of proteins after separation: 1) mass profile fingerprinting ('MS fingerprinting') and 2) sequencing of one or more peptide domains by MS/MS ('MS/MS sequencing'). MS fingerprinting is achieved by accurately measuring the masses of several peptides generated by a proteolytic digest of the intact protein and searching a database for a known protein with that peptide mass fingerprint. MS/MS sequencing involves actual determination of one or more PSTs of peptides derived from the protein digest by generation of sequence-specific fragmentation ions in the quadrapole of an MS/MS instrument. Refinements in both of these techniques have also reduced the amount of individual proteins needed to achieve signature detection.

In one approach, a protein is chemilytically (e.g., cyanogen bromide) or enzymatically (e.g., trypsin) digested at sequence specific sites to form peptides. The specificity of the cleavage yields peptides of reproducible masses that can subsequently be determined by MS. The mass spectrometric peptide pattern detected from an individual protein is then compared to a database of similar patterns generated from purified proteins with known sequences or predicted from the theoretical protein sequence based on the expected digestion pattern. The identity of the unknown protein is then inferred to be that of the known protein that best matches its peptide mass fingerprint.

Historically, techniques such as Edman degradation have been extensively used for protein sequencing. However, sequencing by collision-induced dissociation MS methods (MS/MS sequencing) has rapidly evolved and has proved to be faster and require less protein than Edman techniques. MS sequencing is accomplished either by using higher voltages in the ionization zone of the MS to randomly fragment a single peptide isolated from a protein digest, or more typically by tandem MS using collision-induced dissociation in the ion trap (quadrapole). However, the application of CID methods to protein sequencing require that the protein first be chemilytically or enzymatically digested.

Several techniques can be used to select the peptide fragment used for MS/MS sequencing, including accumulation of the parent peptide fragment ion in the quadrapole MS unit, capillary electrophoretic separation coupled to ES-TOF MS detection, or other liquid chromatographic separations. The amino acid sequence of the peptide is deduced from the molecular weight differences observed in the resulting MS fragmentation pattern of the peptide using the published masses associated with individual amino acid residues in the MS, and has been codified into a semi-autonomous peptide sequencing algorithm. In this approach the peptide to be sequenced is typically accumulated in the quadrapole of a mass spectrometer. CID is then accomplished by injecting a neutral collision gas, typically Ar, into this ion trap to force high energy collisions with the peptide ion. Some of these collisions result in cleavage of the peptide backbone and the generation of smaller ions that, by virtue of their different mass to charge ratio, leave the quadrapole and are detected. The majority of the peptide cleavage reactions occur in a relatively few number of ways, resulting in a high abundance of certain types of cleavage ions. The peptide sequence is then deduced from the apparent masses of these high abundance peptide fragments detected.

Mass spectrometry has the additional advantage in that it can be efficiently coupled to electrophoretic separation techniques both with or without endoproteolytic (e.g., trypsin digestion) or chemilytic (e.g., cyanogen bromide) cleavage of the protein into smaller fragments. However, no mass spectrometric technique has previously been described that directly determines the protein sequence or a protein sequence tag of unknown proteins. Furthermore, no MS sequencing technique has previously been described that directly couples to electrophoretic methods used to separate large numbers of proteins from a mixed protein sample.

For example, in the mass spectrum of a 1425.7 Da peptide (HSDAVFTDNYTR (SEQ ID NO:1)) isolated in an MS/MS experiment acquired in positive ion mode, the difference between the full peptide 1425.7 Da and the next largest mass fragment ($y_{11}$, 1288.7 Da) is 137 Da. This corresponds to the expected mass of an N-terminal histidine residue that is cleaved at the amide bond. For this peptide, complete sequencing is possible as a result of the generation of high-abundance fragment ions that correspond to cleavage of the peptide at almost every residue along the peptide backbone. The generation of an essentially complete set of positively-charged fragment ions that include either end of the peptide is a result of the basicity of both the N- and C-terminal residues (H and R, respectively). If a basic residue is located at the N- or C-terminus, especially R, most of the ions produced in the CID spectrum will contain that residue since positive charge is essentially localized at that site. This greatly simplifies the resulting spectrum since these basic sites direct the fragmentation into a limited series of specific daughter ions. Peptides that lack basic residues tend to fragment into a more complex mixture of fragment ions that makes sequence determination more difficult.

Extending this idea, others demonstrated that attaching a hard positive charge to the N-terminus is an effective approach for directing the production of a complete series of N-terminal fragment ions from a parent peptide in CID experiments regardless of the presence of a basic residue at the N-terminus. Theoretically, all fragment ions are produced by charge-remote fragmentation directed by the fixed-charged group. Peptides have now been modified with several classes of fixed-charged groups, including dimethylalkylammonium, substituted pyridinium, quaternary phosphonium, and sulfonium derivatives. The characteristics of the most desirable labels are that they are easily synthesized, increase the ionization efficiency of the peptide, and (most importantly) direct the formation of a specific fragment ion series with minimal unfavorable label fragmentation. The most favorable derivatives that satisfy these criteria are those of the dimethylalkylammonium class with quaternary phosphonium derivatives being only less favorable due to their more difficult synthesis. Substituted pyridinium derivatives are better suited for high-energy CID as opposed to alkylammonium derivatives.

Despite some progress in peptide analysis, protein identification remains a major bottleneck in field of Proteomics, with up to 18 hours being required to generate a protein sequence tag of sufficient length to allow the identification of a single purified protein from its predicted genomic sequence. Unambiguous protein identification is attained by generating a protein sequence tag (PST), which is now preferentially accomplished by collision-induced dissociation in the quadrapole of an MS/MS instrument. Limitations on the ionization efficiency of larger peptides and proteins restrict the intrinsic detection sensitivity of MS techniques and inhibit the use of MS for the identification of low abundance proteins. Limitations on the mass accuracy of time of flight (TOF) detectors can also constrain the usefulness of MS/MS sequencing, requiring that proteins be digested by proteolytic and chemolytic means into more manageable peptides prior to sequencing. Clearly, rapid and cost effective protein sequencing techniques would improve the speed and lower the cost of proteomics research. Finally, the separation agents and buffers used in traditional protein separation techniques are often incompatible with MS identification methods.

The present invention provides such methods.

Applications of Protein Expression Datasets

Although the limited usefulness of existing protein expression profiling techniques have yielded fairly small and incomplete datasets of protein expression information, the art has been considering theoretical uses of higher resolution protein expression datasets, should they become available in view of new or improved techniques.

If high-resolution, high-sensitivity protein expression profiling methods and datasets were to become available to the art, significant progress in the areas of diagnostics, therapeutics, drug development, biosensor development, and other related areas would be possible. For example, multiple disease markers could be identified and utilized for better confirmation of a disease condition or stage (see U.S. Pat. Nos. 5,672,480; 5,599,677; 5,939,533; and 5,710,007). Subcellular toxicological information could be generated to better direct drug structure and activity correlations (see Anderson, L., "Pharmaceutical Proteomics: Targets, Mechanism, and Function," paper presented at the IBC Proteomics conference, Coronado, Calif. (Jun. 11–12, 1998). Subcellular toxicological information can also be utilized in a biological sensor device to predict the likely toxicological effect of chemical exposures and likely tolerable exposure thresholds (see U.S. Pat. No. 5,811,231).

The present invention provides compositions, methods, apparatus, and computer-based databasing systems for high-throughput, high-resolution, and sensitive protein expression profiling from samples containing a plurality of polypeptide species, such as for example cells, tissues, and organs of bacteria, plants, and animals, and related aspects and uses thereof.

The literature citations discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides electrophoretic methods and devices for separating biological macromolecules (including polypeptides), methods for determining the partial or complete sequence of a polypeptide using mass spectroscopy, methods combining electrophoretic methods with polypeptide sequencing by mass spectroscopy, methods using the above to generate protein expression fingerprint datasets from a sample or a plurality of samples, and computer-based database query and retrieval systems for utilizing said protein expression fingerprint datasets for various uses, including but not limited to diagnostics, therapeutics, drug discovery, drug development, environmental monitoring by bioassay, toxin quantitation, biosensor development, gene therapy, pharmacological monitoring, illicit drug testing, transgenics, metabolic engineering, and related uses described herein or evident to the ordinarily-skilled artisan in view of the present teaching of the specification. The invention also provides the use of each of these methods, apparatuses, compositions, and computerized database query and retrieval systems.

In an aspect, the invention provides a method for separating a polypeptide species from a sample solution containing a plurality of polypeptide species and identifying said polypeptide species, the method comprising electrophoresing said sample solution containing a plurality of polypeptide species in a capillary electrophoresis device to separate and elute polypeptide species and thereby resolving said protein species based on at least one first biophysical parameter which discriminates protein species; and obtaining, by mass spectrographic fragmentation of eluted polypeptide species, a polypeptide sequence tag ("PST") identifying at least one resolved protein species. In a variation of the method, at least two capillary electrophoresis methods are used sequentially prior to mass spectrographic fragmentation of one or more eluted polypeptide species. In a variation of the method, a suitable mass spectrometry label is covalently attached to polypeptide species prior to mass spectrographic fragmentation. In a variation of the method the PST comprises at least 2, and preferably 3 or 4 amino acid residues of the carboxy and/or amino terminal sequence of the eluted polypeptide species. In an embodiment of the method, at least 75 percent of polypeptide species present in the sample solution are separated and identified by PST determination. In an embodiment of the method, at least 5,000 unique polypeptide species present in the sample solution are separated and identified by PST determination; preferably at least 7,500 or more unique polypeptide species can be separated and identified in this method. In an embodiment of the method the polypeptide species in the sample solution are naturally-occurring polypeptides obtained from a sample of a tissue, organ, or cell population.

In an aspect, the invention provides a method of obtaining a protein expression profile from a sample containing a cell population or a protein containing extract thereof, the method comprising: electrophoresing in a first capillary electrophoresis apparatus a solution containing a plurality of protein species obtained from a cell population and thereby resolving said protein species based on at least one first biophysical parameter which discriminates protein species, eluting fractions from said first electrophoresis apparatus and electrophoresing said fractions, separately, in a second capillary electrophoresis apparatus and thereby resolving said protein species based on at least one second biophysical parameter which discriminates protein species, and eluting the protein species and identifying the PSTs of a plurality of protein species from the sample by mass spectroscopy fragmentation. In an embodiment, at least 1,000 resolved proteins from the sample are identified by PST determination; in an embodiment at least 5,000 to 7,500 or more resolved proteins from the sample are identified by PST determination. In a variation, two samples are employed, a first sample from a standard (control or normal) cell population and a second sample from a test cell population; test cell populations can be, for example and not limitation, cells of a different histological type than the standard cell population, pathological cells of the same histological type as the standard cells, treated cells that have been exposed to a toxicological or pharmacological agent but which are of the same histological type as the standard cells, cells of a different passage level or age or replicative potential than the standard cells, or any other variation apparent to those skilled in the art seeking to ascertain protein expression profile differences between a first cell sample and a second cell sample. In an embodiment the test cell population is a biopsy of a putative neoplastic lesion and the standard cell population is a biopsy of surrounding apparently non-neoplastic tissue of the same histological origin, both obtained from a human patient, animal, or plant (e.g., crown gall tumor).

The present invention provides a variety of electrophoretic methods and apparatus for separating mixtures of proteins. The methods involve conducting multiple capillary electrophoresis methods in series, wherein samples for each method other than the initial method contain only a subset of the proteins from the preceding step (e.g., from fractions containing resolved protein from the preceding method). By using a variety of techniques to control elution during electrophoresis, the methods are capable of resolving proteins in even complex mixtures such as obtained from tissues and native cells. Utilizing various labeling schemes and detection methods, certain methods can provide quantitative information on the amount of each of the separated proteins. Such information can be used in the development of protein databases in which proteins expressed under certain conditions are characterized and catalogued. Comparative studies to identify proteins that are differentially expressed between different types of cells or tissues carlalso be conducted with the methods of the present invention. The methods can also be used in diagnostic, structure activity and metabolic engineering studies.

In general, the methods involve performing a plurality of electrophoretic methods in series. Each method in the series includes electrophoresing a sample containing multiple proteins to obtain a plurality of resolved proteins. The sample that is electrophoresed contains only a subset of the plurality of resolved proteins from the immediately preceding method in the series (except the first method of the series in which the sample is the initial sample that contains all the proteins). The resolved proteins from the final electrophoretic method are then detected using various techniques.

The electrophoretic methods typically are capillary electrophoresis methods, such as capillary isoelectric focusing electrophoresis (CIEF), capillary zone electrophoresis (CZE) and capillary gel electrophoresis (CGE), although the methods are amenable to other capillary electrophoresis methods as well. The particular order of the methods can vary. Typically, the methods utilize combinations of electrophoretic methods which separate proteins on the basis of different characteristics (e.g., size, charge, isoelectric point).

In certain methods, the proteins are labeled so that the resolved proteins are more easily detected and to increase the signal-to-noise ratio. Labeling also enables certain methods to be conducted such that the resolved proteins obtained from the final electrophoretic method are quantitated. Quantitation allows the relative abundance of proteins within a sample, or within different samples, to be determined. In certain methods, the time at which proteins are labeled is selected to precede electrophoresis by capillary zone electrophoresis. By selectively labeling certain residues, resolution of proteins during capillary zone electrophoresis can be increased.

Resolution, quantitation and reproducibility are enhanced by utilizing a variety of techniques to control elution of proteins during an electrophoretic method. The particular elution technique employed depends in part upon the particular electrophoretic method. However, in general, hydrodynamic, salt mobilization, pH mobilization and electroosmotic flow are utilized to controllably elute resolved proteins at the end of each electrophoretic separation.

Some methods provide for additional analysis after the electrophoretic separation. The type of analysis can vary and include, for example, infra-red spectroscopy, nuclear magnetic resonance spectroscopy, UV/VIS spectroscopy and complete or partial sequencing. In certain methods, proteins in the final fractions are further analyzed by mass spectroscopy to determine at least a partial sequence for each of the resolved proteins (i.e., to determine a protein sequence tag).

Thus, certain other methods involve performing one or more capillary electrophoretic methods, each of the one or more methods involving: (i) electrophoresing a sample containing multiple proteins within an electrophoretic medium contained within a capillary, and withdrawing and collecting multiple fractions, each fraction containing proteins resolved during the electrophoresing step. Each method in the series is conducted with a sample from a fraction collected in the preceding electrophoretic method, except the first electrophoretic method which is conducted with a sample containing the original mixture of proteins. Prior to conducting the last electrophoretic method, either the proteins in the initial sample are labeled (i.e., labeling precedes all the electrophoretic separations) or by labeling proteins contained in fractions collected prior to the last electrophoretic method. The final electrophoretic method is performed, and resolved protein within, or withdrawn from, the capillary utilized to conduct the final method is detected with a detector. Hence, the detector is adapted to detect resolved protein within the capillary used in the final method or is connected in line with the capillary to detect resolved proteins as they elute from the capillary. In some instances, the detected proteins are quantitated and further analyzed by mass spectroscopy to determine the relative abundance and to establish a protein sequence tag for each resolved protein.

In one aspect, the present invention provides a method for sequencing a portion of a protein, comprising:

(a) contacting a protein with a C-terminus or N-terminus labeling moiety to covalently attach a label to the C— or N-terminus of the protein and form a labeled protein; and (b) analyzing the labeled protein using a mass spectrometric fragmentation method to determine the sequence of at least the two C-terminus or two N-terminus residues.

In one group of embodiments, the method further comprises:

(c) identifying the protein by using the sequence of the at least two C-terminus or two N-terminus residues to search predicted protein sequences from a database of gene sequence data.

In a variation, the method further comprises:

(d) further identifying the protein by using one or more of the separation coordinates (i.e., approximate values of the biophysical parameters used to separate the protein prior to sequencing), for example, the apparent molecular weight, isoelectric point, or electrophoretic mobility.

In another variation, the method further comprises:

(e) further identifying the protein by using other known biological or measurable biophysical parameters of the protein (e.g., cell or tissue type extracted from, subcellular localization, the total or partial amino acid composition, the masses of any peptides resulting from chemilytic or enzymatic digestion).

In a variation, the method further comprises assisted fragmentation of the labeled protein in the mass spectrometer through the use of reactive collision gasses. Illustrative reactive gases may include hydrazine, cyanogen bromide, hydrogen peroxide, ozone, and peracetic acid. Other similar reactive gases will be obvious to those skilled in the art.

In another variation, the method further comprises assisted fragmentation of the labeled protein in the mass spectrometer through the injection of high energy materials in the ionization zone. High energy materials may include transient compounds formed in a plasma or corona discharge, high energy electrons from a beta emitter or electron beam, high energy photons from a laser or high intensity light source of a minimum wavelength of 560 nm. Other high energy materials will be obvious to those skilled in the art.

In another aspect, the present invention provides a method for sequencing a portion of a protein in a protein mixture, the method comprising:

(a) contacting the protein mixture with a C-terminus or N-terminus labeling moiety to covalently attach a label to the C— or N-terminus of the protein and form a labeled protein mixture;

(b) separating individual labeled proteins in the labeled protein mixture; and (c) analyzing the labeled proteins from step (b) by a mass spectrometric method to determine the sequence of at least two C-terminus or two N-terminus residues.

In one group of embodiments, the method further comprises:

(d) identifying the protein by using the sequence of at least two C-terminus or two N-terminus residues in combination with a separation coordinate of the labeled protein and the protein terminus location of the sequence to search predicted protein sequences from a database of gene sequence data.

In each of the methods above, the use of nonproteolytic protein sequencing by in-source fragmentation provides advantages over conventional MS/MS sequencing approaches. One particular advantage is time savings due to elimination of protein digestion steps and elimination of the need to accumulate low volatility peptide ions in the quadrapole. Another advantage is that fewer sequence ambiguities result due to the improved absolute mass accuracy gained by working at the low end of the mass spectrum. Yet another advantage is that better ionization efficiency and corresponding detection sensitivity result from using more energetic ionization conditions and adding one or more charged groups on the labeled fragments. A charged group consisting of a "hard" charge, that is a permanently ionized group such as tetraalkyl- or tetraaryl-ammonium, tetraalkyl- or tetraaryl-phoshonium, N-substituted pyridinium, or tetraalkyl- or tetraaryl-borate species. A charged group further consisting of a "soft" charge, that is an ionizable group which accepts or donates a proton to become ionized, such as carboxylate, phosphonate, sulfonate, alkyl ammonium, pyridinium species. This method provides a contiguous protein sequence tag (PST) that can be used both for unambiguous protein identification by query of a computer database containing genomic sequence information or mRNA sequence information to establish naturally-occurring encoding sequences corresponding to the PST or to generate an N- or C-terminal nucleic acid probe useful for isolating the corresponding cDNA from native cell or tissue samples by polymerase chain reaction amplification or nucleic acid hybridization techniques.

The invention further provides the identification and method of use of chemical labels suitable for enhanced quantitation of the proteins upon electrophoretic separation and subsequent sequencing of said proteins. In one embodiment a single chemical label contains groups that: (i) react with primary amino or carboxylic acid functionalities on the protein, including the N-terminus and C-terminus, (ii) enhance detection sensitivity, and (iii) provide a unique mass signature for the N- or C-terminal labeled peptide fragments generated during fragmentation in a mass spectrometer. In a variation, the label may consist of a mixture of isotopically distinct labels, such that the unique mass signature consists of two or more peaks for each peptide fragment that are separated by more than one amu at a single charge state in the mass spectrum. In another variation, the unique mass signature component and the detection enhancement component may be one and the same. In another embodiment, the chemical label may be modified by partial cleavage and/or addition subsequent to its use for protein quantitation and prior to its use for protein sequencing. In one variation, label addition or cleavage is conducted in solution during withdrawal and transport between the last capillary separation step and injection into the mass spectrometer. In another variation, label addition or cleavage is conducted in the gas phase during ionization in the mass spectrometer.

The invention further provides a method incorporating volatile buffers and surfactants in the final capillary electrophoretic method to facilitate direct coupling of the separation and mass spectrometric detection methods. A volatile buffer is a salt composed of an anion and cation that readily accept or give up a proton to for a volatile organic compound that negligibly interfere with the ionization of proteins or peptides in the mass spectrometer. Illustrative examples include ammonium acetate, ammonium carbonate or bicarbonate, ammonium N-morpholinoethanesulfonate, triethylammonium acetate, pyridium acetate, and pryidium N-morpholinoethanesulfonate. Illustrative examples of volatile surfactants include ammonium, pyridinium, tetramethylammonium, and trimethyl ammonium salts of dodecylsulfate and partially fluorinated or perfluorinated carboxylic, sulfonic, or phosphonic acids of aliphatic hydrocarbons with at least 5 carbon atoms. Many other examples will be evident to those skilled in the art.

The present invention overcomes many of the difficulties associated with current MS-based protein sequencing technologies, including, for example, ionization inefficiency and inaccuracies in fragment mass. Because the methods of the invention preferably eliminate the need for proteolytic or chemolytic digestion of the protein, the present methods provide protein sequencing times that are significantly reduced from the times obtainable using prior methods. Moreover, because the proteins being sequenced are highly fragmented using the present methods, the ionization efficiency and the volatility of the resulting fragments are higher than those of the parent protein, thus leading to a detection sensitivity that is improved over prior methods.

The invention provides a method for identifying a high-resolution protein expression fingerprint for a cell type, tissue, or pathological sample, comprising obtaining a protein-containing extract of a cellular sample and electrophoresing said extract with a first capillary electrophoresis apparatus, eluting protein-containing fractions therefrom, electrophoresing said protein containing fractions on a second capillary electrophoresis apparatus, or plurality thereof in parallel, and identifying the species of proteins by fragmentation mass spectroscopy sequencing to obtain PSTs for a plurality of protein species, and compiling a dataset (or fingerprint record) containing the collection of PSTs obtained thereby. A variation of the method comprises quantitative detection of protein species and compiling a dataset wherein the relative abundance and/or absolute amount of a plurality of protein species eluted from said second capillary electrophoresis is/are cross-tabulated with the PST identification. A typical embodiment comprises attachment of a mass spectroscopy label to the proteins in the protein-containing prior to the last capillary electrophoresis step. In a variation, more than two capillary electrophoresis steps are used; in an embodiment, capillary isoelectric focusing (CIEF) is the first capillary electrophoresis, and the second capillary electrophoresis is either capillary zone electrophoresis (CZE) or capillary gel electrophoresis (CGE).

A protein expression fingerprint comprises an array of at least 100 protein species each having a unique identifier (which may comprise PST and/or electrophoretic mobility data and/or pI and/or any other biophysical property ascertainable by capillary electrophoresis, and/or any other biophysical property known by virtue of the origin of the sample prior to electrophoresis, and/or any other measurable biophysical property), optionally including cross-tabulation with quantitative data indicating relative and/or absolute abundance of each species in the sample. A protein expression fingerprint record comprises a protein expression fingerprint cross-tabulated to data indicating sample source and optionally other bioinformational data (pathological condition, age, passage history, etc.).

In a variation, the invention provides a method for producing a computer database comprising a computer and software for storing in computer-retrievable form a collection of protein expression fingerprint records cross-tabulated with data specifying the source of the protein-containing sample from which each protein expression fingerprint record was obtained. In a variation, at least one of the sources is from a tissue sample known to be free of pathological disorders. In a variation, at least one of the sources is a known pathological tissue specimen, for example but not limitation a neoplastic lesion or a tissue specimen containing an infectious agent such as a virus, or the like. In a variation, the protein expression fingerprint records cross-tabulate at least the following parameters for each protein species in a sample: (1) a unique identification code, which can comprise a PST and/or characteristic electrophoretic separation coordinate; (2) sample source; optionally (3) absolute and/or relative quantity of the protein species present in the sample, optionally (4) presence or absence of amino or carboxyterminal post-translational modifications, and/or optionally (5) original electropherograms and/or mass spectra used to identify the proteins and PST. A database comprises a plurality of protein expression fingerprint records, each of which represents a protein expression fingerprint from one sample or a subfraction thereof.

The invention also provides for the storage and retrieval of a collection of such polypeptide fingerprints in a computer data storage apparatus, which can include magnetic disks, optical disks, magneto-optical disks, DRAM, SRAM, SGRAM, SDRAM, magnetic bubble memory devices, and other data storage devices, including CPU registers and on-CPU data storage arrays. Typically, the polypeptide fingerprint records are stored as a bit pattern in an array of magnetic domains on a magnetizable medium or as an array of charge states or transistor gate states, such as an array of cells in a DRAM device (e.g., each cell comprised of a transistor and a charge storage area, which may be on said transistor). The invention provides such storage devices, and computer systems built therewith, comprising a bit pattern encoding a protein expression fingerprint record comprising unique identifiers for at least 100 protein species cross-tabulated with sample source. The invention provides a method for identifying related polynucleotide or polypeptide sequences, comprising performing a computerized comparison between a PST sequence stored in or retrieved from a computer storage device or database and at least one other sequence; such comparison can comprise a sequence analysis or comparison algorithm or computer program embodiment thereof (e.g., FASTA, TFASTA, GAP, BESTFIT) and/ or the comparison may be of the relative amount of a PST sequence in a pool of sequences determined from a polynucleotide sample of a specimen. The invention provides a computer system comprising a storage device having a bit pattern encoding a database having at least 100 protein expression fingerprint records obtained by the methods of the invention, and a program for sequence alignment and comparison to predetermined genetic or protein sequences. The invention also provides a magnetic disk, such as an IBM-compatible (DOS, Windows, Windows95/98/2000, Windows NT, OS/2) or other format (e.g., Linux, SunOS, Solaris, AIX, SCO Unix, VMS, MV, Macintosh, etc.) floppy diskette or hard (fixed, Winchester) disk drive, comprising a bit pattern encoding a protein expression fingerprint record; often the disk will comprise at least one other bit pattern encoding a polynucleotide and/or polypeptide sequence other than a protein expression fingerprint record of the invention, typically in a file format suitable for retrieval and processing in a computerized sequence analysis, comparison, or relative quantitation method. The invention also provides a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding a protein expression fingerprint record of the invention. The invention also provides a method for transmitting a protein expression fingerprint record of the invention, which is uniquely determined by the methodology employed to generate it, comprising generating an electronic signal on an electronic communications device, such as a modem, ISDN terminal adapter, DSL, cable modem, ATM switch, or the like, whereby said signal comprises (in native or encrypted format) a bit pattern encoding a protein expression fingerprint record or a database comprising a plurality of protein expression fingerprint records obtained by the method of the invention, respectively.

The invention provides a computer system for comparing a query polypeptide sequence or query polynucleotide sequence to a database containing an array of PST sequences and other data structures of a protein expression fingerprint record obtained by the method of the invention, and ranking database sequences based on the degree of sequence identity and gap weight to query sequence. A central processor is initialized to load and execute computer program for alignment and/or comparison of amino acid sequences or nucleotide sequences. A query sequence comprising at least 4 amino acids or 12 nucleotides is entered into the central processor via I/O device. Execution of computer program results in central processor retrieving sequence data from data file, which comprises a binary description of a protein expression fingerprint record or portion thereof containing polypeptide sequence data for the record. Said sequence data or record and said computer program can be transferred to secondary memory, which is typically random access memory (e.g., DRAM, SRAM, SGRAM, or SDRAM). Sequences are ranked according to the degree of sequence identity to the query sequence and results are output via an I/O device. For example and not to limit the invention, a central processor can be a conventional computer (e.g., Intel Pentium, PowerPC, Alpha, PA-8000, SPARC, MIPS 4400, MIPS 10000, VAX, etc.); a program can be a commercial or public domain molecular biology software package (e.g., UWGCG Sequence Analysis Software, Darwin, blastn); a data file can be an optical or magnetic disk, a data server, a memory device (e.g., DRAM, SRAM, SGRAM, SDRAM, EPROM, bubble memory, flash memory, etc.); an I/O device can be a terminal comprising a video display and a keyboard, a modem, an ISDN terminal adapter, an Ethernet port, a punched card reader, a magnetic strip reader, or other suitable I/O device.

The invention provides a computer program for comparing query polypeptide sequence(s) or query polynucleotide sequence(s) or a query protein expression fingerprint to a protein expression fingerprint database obtained by a method of the invention and ranking database sequences based on the degree of similarity of protein species expressed and relative and/or absolute abundances in a sample. The initial step is input of a query polynucleotide or polypeptide sequence, or protein expression fingerprint record obtained by a method of the invention, input via n I/O device. A data file is accessed in to retrieve a collection of protein expression fingerprint records for comparison to the query; said collection comprises protein expression fingerprint records obtained by a method of the invention. Individually or collectively sequences or other cross-tabulated information of the protein expression fingerprint collection are optimally matched to the query sequence(s) or query protein expression record such as by the algorithm of Needleman and Wunsch or the algorithm of Smith and Waterman or other suitable algorithm obtainable by those skilled in the art. Once aligned or matched, the percentage of sequence or fingerprint similarity is computed in for each aligned or matched sequence to generate a similarity value for each sequence or fingerprint in the protein expression fingerprint record collection as compared to the query sequence(s) or fingerprint(s). Sequences are ranked in order of greatest sequence identity or weighted match to the query sequence or query fingerprint, and the relative ranking of the sequence or fingerprint to the best matches in the collection of records is thus generated. A determination is made: if more sequences or fingerprint records exist in the data file, the additional sequences/fingerprints or a subset thereof are retrieved and the process is iterated; if no additional sequences/fingerprints exist in the data file, the rank ordered sequences/fingerprints are via an I/O device, thereby displaying the relative ranking of sequences/fingerprints among the sequences/fingerprints of the data file optimally matched and compared to the query sequence(s) or fingerprint(s).

The invention also provides the use of a computer system described above, which comprises: (1) a computer, (2) a stored bit pattern encoding a collection of protein expression fingerprint records obtained by the methods of the invention, which may be located in said computer, (3) a comparison sequence or fingerprint, such as a query sequence or a data file containing fingerprint information, and (4) a program for alignment and comparison, typically with rank-ordering of comparison results on the basis of computed similarity values. In an embodiment, neural network pattern matching/recognition software is trained to identify and match fingerprint records based on back propagation using empirical data input by a user. The computer system and methods described permit the identification of the relative relationship of a query protein expression fingerprint to a collection of protein expression fingerprints; preferably all protein expression fingerprints (query and database) are obtained by the methods of the invention.

A further understanding of the nature and advantages of the invention will become apparent by reference to the remaining portions of the specification and drawings.

DETAILED DESCRIPTION

Definitions

Figure 1:
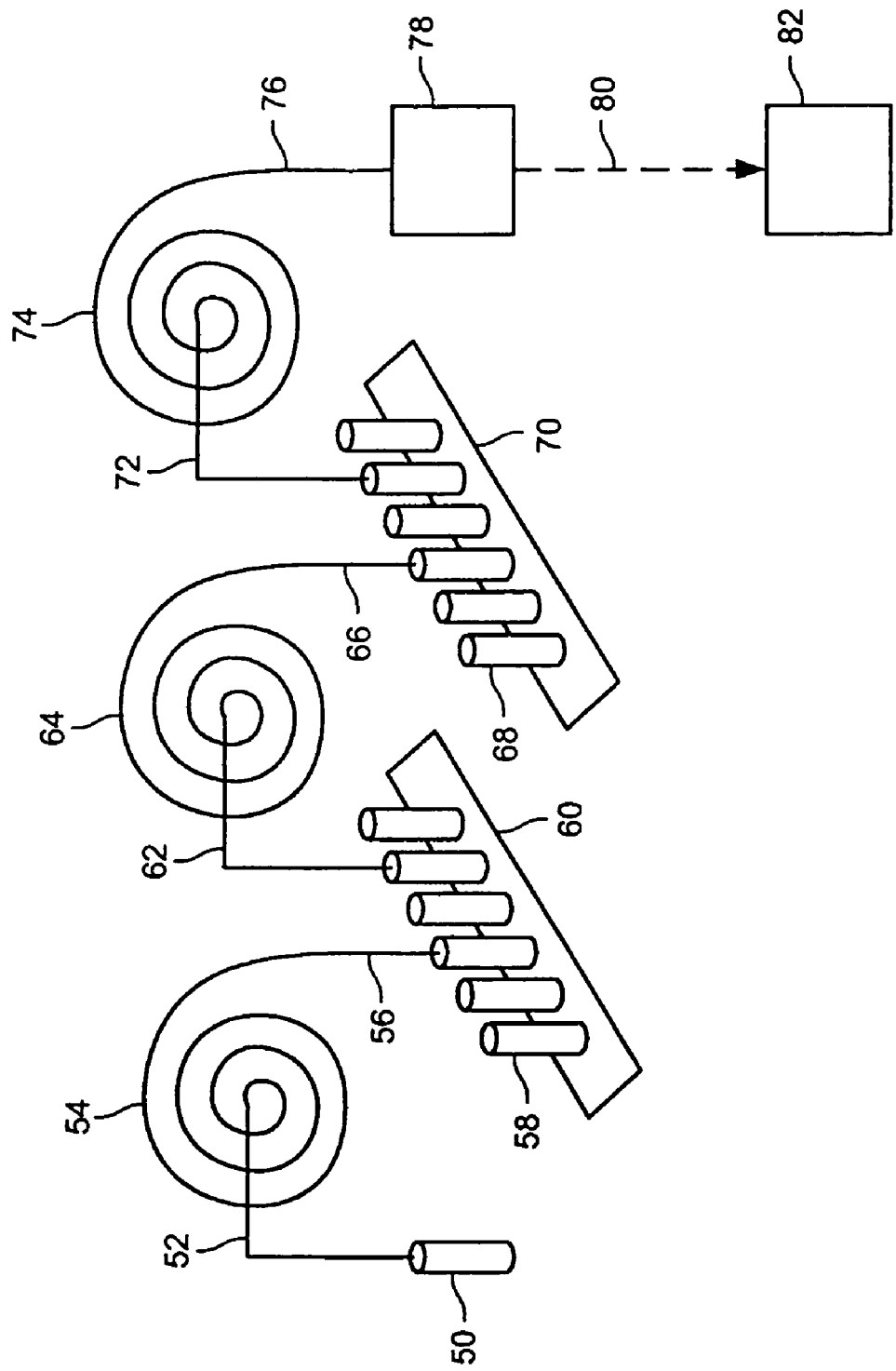
FIG. 1 is a schematic representation of one example of an electrophoretic system that can be utilized with certain methods of the invention.

Unless defined otherwise, all technical and scientific terms used herein generally have the same meaning as commonly understood by one of ordinary skill in the art to which this invention belongs. Generally, the nomenclature used herein and the laboratory procedures in molecular biology, organic chemistry described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references—(see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those known and employed in the art. Standard techniques, or modifications thereof, are used for chemical syntheses and chemical analyses.

As used herein, the terms protein, peptide and polypeptide refer to a polymer of amino acid residues. The terms also apply to amino acid polymers in which one or more amino acids are chemical analogues of corresponding naturally-occurring amino acids, including amino acids which are modified by post-translational processes (e.g., glycosylation and phosphorylation). "Protein", as used herein, means any protein, including, but not limited to peptides, enzymes, glycoproteins, hormones, receptors, antigens, antibodies, growth factors, etc., without limitation. Presently preferred proteins include those comprised of at least 25 amino acid residues, more preferably at least 35 amino acid residues and still more preferably at least 50 amino acid residues.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. The of the amino acids may be either the D- or L-isomer. The L-isomers are generally preferred. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991)). Stereoisomers (e.g., D-amino acids) of the twenty conventional amino acids, unnatural amino acids such as, -disubstituted amino acids, N-alkyl amino acids, lactic acid, and other unconventional amino acids may also be suitable components for polypeptides of the present invention. Examples of unconventional amino acids include: 4-hydroxyproline, -carboxyglutamate, —N,N,N-trimethyllysine, —N-acetyllysine, O-phosphoserine, N-acetylserine, N-formylmethionine, 3-methylhistidine, 5-hydroxylysine, —N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specifies otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The term "agent" is used herein to denote a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein "normal blood" or "normal human blood" refers to blood from a healthy human individual who does not have an active neoplastic disease or other disorder of lymphocytic proliferation, or an identified predisposition for developing a neoplastic disease. Similarly, "normal cells", "normal cellular sample", "normal tissue", and "normal lymph node" refers to the respective sample obtained from a healthy human individual who does not have an active neoplastic disease or other lymphoproliferative disorder.

As used herein the terms "pathognomonic concentration", "pathognomonic amount", and "pathognomonic staining pattern" refer to a concentration, amount, or localization pattern, respectively, of a protein or protein fingerprint in a sample, that indicates the presence of a pathological (e.g., neoplastic, senescent, immunodeficient, neurodegenerative, inflammatory, etc.) condition or a predisposition to developing a neoplastic disease, such as carcinoma, sarcoma, or leukemia. A pathognomonic amount is an amount of a protein or protein expression fingerprint feature in a cell or cellular sample that falls outside the range of normal clinical values that is established by prospective and/or retrospective statistical clinical studies. Generally, an individual having a neoplastic disease (e.g., carcinoma, sarcoma, or leukemia) will exhibit an amount of a predetermined protein or a matched protein expression fingerprint in a cell or tissue sample that is outside the range of concentrations that characterize normal, undiseased individuals; typically the pathognomonic concentration is at least about one standard deviation outside the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50–200 mM NaCl or KCl, pH 6.5–8.5, 20–45 C and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or nonionic detergents and/or membrane fractions and/or antifoam agents and/or scintillants.

As used herein, the term "multimer" comprises dimer and higher order complexes (trimer, tetramer, pentamer, hexamer, heptamer, octamer, etc.). "Homomultimer" refers to complexes comprised of the same subunit species. "Heteromultimer" refers to complexes comprised of more than one subunit species.

The term "alkyl" is used herein to refer to a branched or unbranched, saturated or unsaturated, monovalent hydrocarbon radical, generally having from about 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls," and "cyclic alkyl."

"Substituted alkyl" refers to alkyl as just described including one or more substituents such as lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "aryl" is used herein to refer to an aromatic substituent, which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "arylalkyl" is used herein to refer to a subset of "aryl" in which the aryl group is attached to another group by an alkyl group as defined herein.

"Substituted arylalkyl" defines a subset of "substituted aryl" wherein the substituted aryl group is attached to another group by an alkyl group as defined herein.

The term "acyl" is used to describe a ketone substituent, —(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to —NRR', wherein R and R' are independently H, alkyl, aryl or substituted analogues thereof. "Amino" encompasses "alkylamino" denoting secondary and tertiary amines and "acylamino" describing the group RC(O)NR'.

The term "alkoxy" is used herein to refer to the —OR group, where R is alkyl, or a substituted analogue thereof. Suitable alkoxy radicals include, for example, methoxy, ethoxy, t-butoxy, etc.

As used herein, the term "aryloxy" denotes aromatic groups that are linked to another group directly through an oxygen atom. This term encompasses "substituted aryloxy" moieties in which the aromatic group is substituted as described above for "substituted aryl." Exemplary aryloxy moieties include phenoxy, substituted phenoxy, benzyloxy, phenethyloxy, etc.

As used herein "aryloxyalkyl" defines aromatic groups attached, through an oxygen atom to an alkyl group, as defined herein. The term "aryloxyalkyl" encompasses "substituted aryloxyalkyl" moieties in which the aromatic group is substituted as described for "substituted aryl."

As used herein, the term "mercapto" defines moieties of the general structure —S—R wherein R is H, alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are replaced by a heteroatom such as nitrogen, oxygen or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to another group.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to another group.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to another group.

I. Overview

The present invention provides methods and apparatus for achieving the separation of proteins, including significant resolution of proteins in complex mixtures from native cell and tissue samples. The invention is based in part upon the recognition that multidimensional electrophoretic methods involving multiple (typically different) electrophoretic methods performed in series utilizing controlled fractionation techniques to obtain defined fractions can be used to achieve high resolution of proteins. In a variation, labeling and detection steps can be included to increase sensitivity and to obtain accurate and reproducible quantitative information about the resolved proteins. In another variation, the buffer system can be altered in the last separation step, through the use of volatile salts, organic solvents, and ephemeral surfactants to make the eluent compatible with subsequent mass spectrometric analysis. Typically, the electrophoretic methods are capillary electrophoresis methods, particularly combinations of capillary isoelectric focusing (CIEF), capillary zone electrophoresis (CZE) and capillary gel electrophoresis (CGE).

Several features enable methods to be performed in a controlled and reproducible fashion. For example, once proteins have had an opportunity to fractionate within the electrophoretic medium contained within a capillary, elution conditions are tailored so that separated proteins are eluted in a controlled fashion to yield defined fractions in which the proteins contained within a fraction fall within a certain pH range, electrophoretic mobility range, or molecular weight range, for example. In certain methods, proteins are labeled at a selected stage of the separation process and the labeled proteins detected using a detector. Labeling enables proteins present at low concentration to more easily be detected and enhances reproducibility by increasing signal-to-noise ratios. The detector can be used to detect proteins as separated within an electrophoretic cavity or after they are eluted from the cavity. The combination of labeling and detection also enables separated proteins to be quantified. In a variation, the labeling moiety consists of components that impart a covalent linkage to the N-terminus or C-terminus of the protein, at least one component that increases the detectability of the protein, and, optionally, a component that imparts a unique mass signature to the protein, or labeled peptide fragments of the protein in a mass spectrometer.

If additional information is desired, the methods can be expanded to include further analysis by techniques besides electrophoresis. For example, in certain method variations, fractions collected from the final electrophoretic method are individually analyzed by mass spectroscopy to obtain additional information, such as molecular weight and a partial sequence, the masses of chemilytic or enzymatically derived peptides, and total or partial amino acid compositions. In a variation, the initial sample is fractionated by ammonium sulfate precipitation, subcellular fractionation, or chromatographic means (e.g., reverse phase, size exclusion, affinity, and ion). In a further variation, the biological or biophysical parameters underlying each expansion to the method can be incorporated as separation parameters and utilized to further identify any protein species resolved by the method and/or annotate the description of the protein species resolved by the method in a database of such protein species.

Quantitative detection and the ability to automate the methods means that the methods are amenable to a variety of screening, comparative and diagnostic studies. For example, the methods can be utilized to develop comparative protein expression data. Such comparative studies can be utilized to identify markers of specific diseases, potential targets for pharmaceuticals and/or drug candidates. Once markers that are selectively expressed in certain disease states, for example, are identified, the methods of the invention have utility in diagnostic applications. In a variation, the methods can be incorporated into miniaturized separation and detection devices, in which a plurality of capillary electrophoretic methods are used to resolve, detect, and quantify one or more protein markers for diagnostic purposes. The methods of the invention can also be utilized to develop a protein database that includes, for example, isoelectric points, apparent molecular weights and relative abundance information and partial or complete protein sequence information for proteins obtained from different cells, tissues or physiological states. The methods also find utility in studies on structure/activity relationships and in metabolic engineering investigations in which one genetically modifies a certain gene and then determines what effects such a modification has on cellular protein expression.

II. Separation Methods

Summary

The present invention provides a variety of electrophoretic methods and apparatus for separating mixtures of proteins. The methods involve conducting multiple capillary electrophoresis methods in series, wherein samples for each method other than the initial method contain only a subset of the proteins from the preceding step (e.g., from fractions containing resolved protein from the preceding method). By using a variety of techniques to control elution during electrophoresis, the methods are capable of resolving proteins in even complex mixtures such as obtained from tissues and native cells. Utilizing various labeling schemes and detection methods, certain methods can provide quantitative information on the amount of each of the separated proteins. Such information can be used in the development of protein databases in which proteins expressed under certain conditions are characterized and catalogued. Comparative studies to identify proteins that are differentially expressed between different types of cells or tissues can also be conducted with the methods of the present invention. The methods can also be used in diagnostic, structure activity and metabolic engineering studies.

In general, the methods involve performing a plurality of electrophoretic methods in series. Each method in the series includes electrophoresing a sample containing multiple proteins to obtain a plurality of resolved proteins. The sample that is electrophoresed contains only a subset of the plurality of resolved proteins from the immediately preceding method in the series (except the first method of the series in which the sample is the initial sample that contains all the proteins). The resolved proteins from the final electrophoretic method are then detected using various techniques.

The electrophoretic methods typically are capillary electrophoresis methods, such as capillary isoelectric focusing electrophoresis (CIEF), capillary zone electrophoresis (CZE) and capillary gel electrophoresis (CGE), although the methods are amenable to other capillary electrophoresis methods as well. The particular order of the methods can vary. Typically, the methods utilize combinations of electrophoretic methods which separate proteins on the basis of different characteristics (e.g., size, charge, isoelectric point).

In certain methods, the proteins are labeled to more easily detect the resolved proteins, to alter the charge of the proteins, to facilitate their separation, and/or to increase the signal-to-noise ratio. Labeling also enables certain methods to be conducted such that the resolved proteins obtained from the final electrophoretic method are quantitated. Quantitation allows the relative abundance of proteins within a sample, or within different samples, to be determined. In certain methods, the time at which proteins are labeled is selected to precede electrophoresis by capillary zone electrophoresis. By selectively labeling certain residues, resolution of proteins during capillary zone electrophoresis can be increased.

Resolution, quantitation and reproducibility are enhanced by utilizing a variety of techniques to control elution of proteins during an electrophoretic method. The particular elution technique employed depends in part upon the particular electrophoretic method. However, in general, hydrodynamic, salt mobilization, pH mobilization and electroosmotic flow are utilized to controllably elute resolved proteins at the end of each electrophoretic separation.

Some methods provide for additional analysis after the electrophoretic separation. The type of analysis can vary and include, for example, infra-red spectroscopy, nuclear magnetic resonance spectroscopy, UV/VIS spectroscopy, fluorescence spectroscopy, and complete or partial sequencing. In certain methods, proteins in-he final fractions are farther analyzed by mass spectroscopy to determine at least a partial sequence for each of the resolved proteins (i.e., to determine a protein sequence tag).

Thus, certain other methods involve performing one or more capillary electrophoretic methods, each of the one or more methods involving: (i) electrophoresing a sample containing multiple proteins within an electrophoretic medium contained within a capillary, and (ii) withdrawing and collecting multiple fractions, each fraction containing proteins resolved during the electrophoresing step. Each method in the series is conducted with a sample from a fraction collected in the preceding electrophoretic method, except the first electrophoretic method which is conducted with a sample containing the original mixture of proteins. The proteins are labeled prior to conducting the last electrophoretic method. Either the proteins in the initial sample are labeled (i.e., labeling precedes all the electrophoretic separations), or the proteins contained in fractions collected are labeled prior to the last electrophoretic method. The final electrophoretic method is performed, and resolved protein within, or withdrawn from, the capillary utilized to conduct the final method is detected with a detector. Hence, the detector is adapted to detect resolved protein within the capillary used in the final method or is connected in line with the capillary to detect resolved proteins as they elute from the capillary. In some instances, the detected proteins are quantitated and further analyzed by mass spectroscopy to determine their relative abundance and/or to establish a protein sequence tag for each resolved protein.

The present invention provides methods and apparatus for achieving the separation of proteins, including significant resolution of proteins in complex mixtures from native cell and tissue samples. The invention is based in part upon the recognition that multidimensional electrophoretic methods involving multiple (typically different) electrophoretic methods performed in series utilizing controlled fractionation techniques to obtain defined fractions can be used to achieve high resolution of proteins. Labeling and detection steps can be included to increase sensitivity, alter the separation coordinates of the proteins, and to obtain accurate and reproducible quantitative information about the resolved proteins. Typically, the electrophoretic methods are capillary electrophoresis methods, particularly combinations of capillary isoelectric focusing (CIEF), capillary zone electrophoresis (CZE) and capillary gel electrophoresis (CGE).

Several features enable methods to be performed in a controlled and reproducible fashion. For example, once proteins have had an opportunity to fractionate within the electrophoretic medium contained within a capillary, elution conditions are tailored so that separated proteins are eluted in a controlled fashion to yield defined fractions in which the proteins contained within a fraction fall within a certain pH range, electrophoretic mobility range, or molecular weight range, for example. In certain methods, proteins are labeled at a selected stage of the separation process and the labeled proteins detected using a detector. Labeling enables proteins present at low concentration to more easily be detected and enhances reproducibility by increasing signal-to-noise ratios. The detector can be used to detect proteins as separated within an electrophoretic cavity or after they are eluted from the cavity. The combination of labeling and detection also enables separated proteins to be quantified. The combination of labeling and separation can alter the net charge or solubility of the proteins causing a change in their separation coordinates, for example, their separation order, the fraction in which they are collected, and elution time.

If additional information is desired, the methods can be expanded to include further analysis by techniques besides electrophoresis. For example, in certain methods, fractions collected from the final electrophoretic method are individually analyzed by mass spectroscopy to obtain additional information, such as molecular weight and partial sequence.

Quantitative detection and the ability to automate the methods means that the methods are amenable to a variety of screening, comparative and diagnostic studies. For example, the methods can be utilized to develop comparative protein expression data. Such comparative studies can be utilized to identify markers of specific diseases, potential targets for pharmaceuticals and/or drug candidates. Once markers that are selectively expressed in certain disease states, for example, are identified, the methods of the invention have utility in diagnostic applications. The methods of the invention can also be utilized to develop a protein database that includes, for example, separation coordinates, isoelectric points, apparent molecular weights and relative abundance information for proteins in different cells, tissues or states. The methods also find utility in studies on structure/activity relationships and in metabolic engineering investigations in which one genetically modifies a certain gene and then determines what effects such a modification has on cellular protein expression.

General Separation Methodology

The methods of the present invention utilize a combination of electrophoretic methods conducted in series to resolve mixtures of proteins. The methods are said to be conducted in series because the sample(s) electrophoresed in each method are from solutions or fractions containing proteins electrophoresed in the preceding method, with the exception of the sample electrophoresed in the initial electrophoretic method. As used herein, the terms protein, peptide and polypeptide are used interchangeably and refer to a polymer of amino acid residues. The term also applies to amino acid polymers in which one or more amino acids are chemical analogues of corresponding naturally-occurring amino acids, including amino acids which are modified by post-translational processes (e.g., glycosylation and phosphorylation).

The series of electrophoretic methods are typically conducted in such a way that proteins in an applied sample for each electrophoretic method of the series are isolated or resolved physically, temporally or spacially to form a plurality of fractions each of which include only a subset of proteins of the applied sample. Thus, a fraction refers to a protein or mixture of proteins that are resolved physically, temporally or spacially from other proteins in a sample subjected to electrophoresis. Resolved proteins can refer to a single species or a mixture of proteins that are separated from other proteins during an electrophoretic method. As just noted, samples in the various electrophoretic methods are obtained from such fractions, with the exception of the first electrophoretic method in which the sample is the original sample containing all the proteins to be separated.

Typically, these multiple electrophoretic methods in the series separate proteins according to different characteristics. For example, one method can separate proteins on the basis of isoelectric points (e.g., capillary isoelectric focusing electrophoresis), other methods can separate proteins on the basis of their intrinsic or induced (through the application of a label to certain ionizable amino acid residues) charge-to-mass ratio at any given pH (e.g., capillary zone electrophoresis), whereas other methods separate according to the size of the proteins (e.g., capillary gel electrophoresis). Such approaches that separate proteins through a series of electrophoretic methods are referred to herein as "multidimensional" electrophoretic methods, wherein each particular electrophoretic method constitutes a "dimension."

Figure 2A:
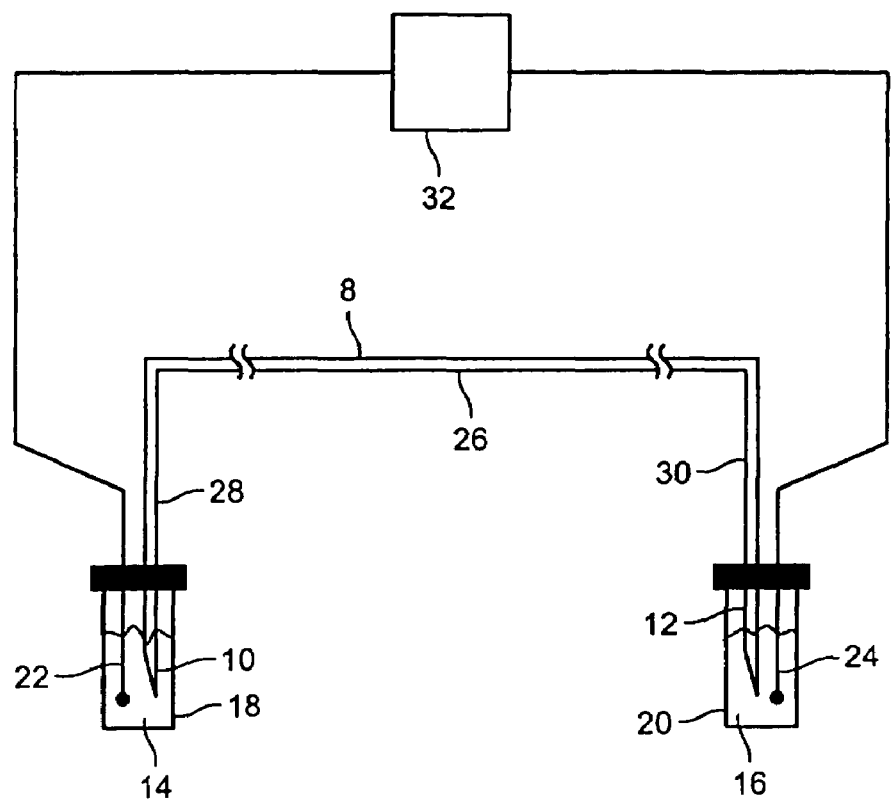
FIG. 2A is a schematic representation of some of the major elements of an electrophoretic system utilized in conducting certain electrophoretic methods of the invention.

Apparatus used to conduct various electrophoretic methods are known in the art. In general, however, and as shown in FIG. 2A, the basic configuration of a typical capillary electrophoretic system utilized in certain methods of the invention-includes a capillary 8 having two ends 10, 12. One end 10 is in contact with an anode solution or analyte 14 contained in an anode reservoir 18 and the other end 12 is in contact with a cathode solution or catholyte 16 in a cathode reservoir 20. One electrode (the anode) 22 is positioned to be in electrical communication with the anode solution 14 and a second electrode 24 is positioned to be in electrical communication with the cathode solution 16. The cavity 26 of the capillary 8 is filled with an electrophoretic medium, which in some instances can include a polymer matrix. As used herein, the term anode refers to the positively charged electrode. Thus, negatively charged species move through the electrophoretic medium toward the anode. The term cathode refers to the negatively charged electrode; positively charged species migrate toward this electrode.

Sample is introduced into the capillary 8 via an inlet 28, and the protein components therein resolved as an electrical field is applied between the two electrodes 22, 24 by a power source 32 and the proteins separate within the electrophoretic medium contained within the separation cavity 26. Protein components can be controllably eluted from the capillary via outlet 30 by controlling various parameters such as electroosmotic flow (see infra) and/or by changing the composition of one or both of the reservoir solutions (e.g., adjusting the pH or salt concentration). Typically, the inlet 28 and the outlet 30 are simply portions of the capillary formed to allow facile insertion into a container containing sample, analyte or catholyte.

The term "capillary" as used in reference to the electrophoretic device in which electrophoresis is carried out in the methods of the invention is used for the sake of convenience. The term should not be construed to limit the particular shape of the cavity or device in which electrophoresis is conducted. In particular, the cavity need not be cylindrical in shape. The term "capillary" as used herein with regard to any electrophoretic method includes other shapes wherein the internal dimensions between at least one set of opposing faces are approximately 2 to 1000 microns, and more typically 25 to 250 microns. An example of a non-tubular arrangement that can be used in certain methods of the invention is the a Hele-Shaw flow cell. Further, the capillary need not be linear; in some instances, the capillary is wound into a spiral configuration, for example.

An example of a system utilized with certain methods of the invention is illustrated in FIG. 1. This particular example shows a system in which three electrophoresis methods (initial, intermediate and final methods) are linked. The particular number of electrophoretic methods conducted can vary, although the methods of the invention include at least two electrophoretic methods. Most typically, the methods utilize two or three electrophoretic separation methods.

As can be seen in FIG. 1, an initial sample containing a plurality of proteins is introduced from sample container 50 into a first separation cavity of a first capillary 54 via sample inlet 52 utilizing any of a number of methods known in the art. Examples of suitable methods include, pulling sample into the sample inlet 52 under vacuum (e.g., by pulling a vacuum on the sample outlet) or pushing sample into the sample inlet 52 by pressurizing the sample container 50. Electromigration, often referred to as electrokinetic injection, is another option. Once the initial sample is introduced into sample inlet 52, the sample is then electrophoresed within the first separation cavity within the first capillary 54. The first separation cavity contains a desired electrophoretic medium in which proteins in the initial sample are at least partially resolved. Electrophoretic medium containing resolved proteins is withdrawn from the first cavity, typically out the end of the separation cavity opposite the end in which sample was introduced, although other withdrawal sites can be utilized (see infra). The withdrawn medium travels through outlet 56 and is collected in separate containers 58 as multiple fractions. As shown in FIG. 1B, the containers 58 into which fractions are collected are typically associated with a fraction collection device (a portion of which is shown 60) capable of automatically advancing a set of containers 58 to collect defined fractions (e.g., fractions of a certain volume or covering a selected pH range).

A sample from a fraction collected from the first electrophoretic method is then withdrawn from one of the plurality of containers 58, again utilizing techniques such as those described supra, via a second sample inlet 62. Proteins in the sample from the fraction can then be further resolved by conducting an intermediate electrophoretic method (in the example shown in FIG. 1, the second electrophoretic method). The sample is introduced into a second capillary 64 via inlet 62 and the proteins within the sample further separated within the electrophoretic medium contained within the second separation cavity of the second capillary 64 and then eluted from the cavity via outlet 66. As with the first electrophoretic separation, the electrophoretic medium containing the resolved or partially resolved proteins is collected as separate fractions within containers 68 typically aligned and advanced by a second fraction collection device (a portion of which is shown 70).

A process similar to the second/intermediate method is conducted during the final electrophoretic method (the third electrophoretic separation method shown in FIG. 1). Sample is drawn via inlet 72 from a container 68 containing a fraction obtained during the preceding method and is introduced into a third or final electrophoretic cavity of a third capillary 74 containing a third electrophoretic medium in which proteins contained in the applied sample are separated still further yet by electrophoresis. The third electrophoretic medium containing the further isolated proteins is subsequently withdrawn through outlet 76.

As noted above, more than the three electrophoretic methods shown in FIG. 1 can be performed. Such methods essentially involve repeating the general steps described for the second/intermediate electrophoretic separation above one or more times.

Following the final electrophoretic separation, a variety of different options for analyzing the resolved proteins are available. As shown in FIG. 1, withdrawn electrophoretic medium can be passed through a detector 78 in fluid communication with the separation cavity of the last capillary 74 to detect the resolved proteins. The detector 78, or an optional quantifying device capable of receiving a signal from the detector (not shown), can be used to quantitate the amount of protein within a certain portion or fraction of the electrophoretic medium.

Alternatively, or in addition, fractions can be taken from the electrophoretic medium exiting the final capillary 74 or the detector 78 and analyzed by an analyzer 82 using some technique other than electrophoresis. Examples of such techniques include various spectroscopic methods (e.g., IR, UV/VIS and NMR) and various mass spectroscopy methods (e.g., electrospray ionization-time of flight [ESI-TOF] mass spectroscopy). Mass spectral data, for example, can be utilized to deduce a partial or full sequence of the protein(s) (i.e., determine a protein sequence tag) within a particular fraction. FIG. 1 depicts a situation in which sample is withdrawn via line 80 (dashed to indicate optional nature of this step) to another analyzer 82 (e.g., mass spectrometer).

A number of other configurations can be utilized. For example, the capillaries and detector(s) can be fabricated within a microfluidic chip (see infra).

The specific elution conditions utilized to withdraw resolved proteins from the separation cavity depends upon the type of electrophoretic method conducted and is described more fully below for each of the electrophoretic methods typically utilized in the present invention. In general, however, once proteins have been resolved, the conditions within the separation cavity are adjusted as necessary (or the initial conditions selected) to achieve selective or controlled elution of the proteins from the cavity. For example, elution can be achieved by adding salts to, or adjusting the pH of, the anode or cathode solution, by regulating electroosmotic flow, by applying hydrodynamic pressure or combinations of the foregoing.

Using the methods of the invention, resolved proteins can be isolated physically (e.g., placement into different containers such as illustrated in FIG. 1), spatially (e.g., spread throughout the electrophoretic medium contained in the separation cavity) and/or temporally (e.g., controlling elution so different proteins within a sample elute from the capillary at different times). Thus, the methods of the invention can separate mixtures of proteins as a function of the composition of elution buffers and/or time, and are not limited to the spatial separation of proteins as are certain traditional two-dimensional (2-D) gel electrophoresis systems. Instead, with controlled elution, fractions can be collected so that proteins within a fraction fall within a range of isoelectric, electrophoretic mobility, or molecular weight values, for example. Controlled elution of proteins means that methods can be performed in a reproducible fashion. Such reproducibility is important in conducting comparative studies and in diagnostic applications, for example.

During the elution or withdrawing of resolved proteins, generally only a portion of the electrophoretic medium containing the resolved proteins is typically collected in any given fraction. This contrasts with certain 2-D methods in which a gel containing all the resolved proteins is exuded from the separation cavity and the exuded gel containing all the proteins is used to conduct another electrophoretic separation.

Spacially, physically or temporally resolved proteins obtained at the conclusion of one electrophoretic method are then used as the source of samples for further separation of proteins contained within the fraction during a subsequent electrophoretic method. As illustrated in FIG. 1, typically samples from different resolved fractions are sequentially electrophoresed on the same capillary. Normally another sample is not applied until the proteins in the preceding sample are sufficiently withdrawn from the separation cavity so that there is no overlap of proteins contained in different fractions. Sequential elution of fractions through the same column can significantly reduce or eliminate variations resulting from differences in cross-linking or electric field strength that can be problematic in certain slab gel electrophoretic methods. Hence, sequential separation can further enhance the reproducibility of the methods of the invention. Other methods, however, can be performed in a parallel format, wherein samples from different fractions are electrophoresed on separate capillaries. This approach allows for separations to be completed more quickly. However, the use of multiple capillaries can increase the variability in separation conditions, thereby reducing to some extent reproducibility between different samples.

In certain methods, proteins are labeled at a selected stage of the separation process and then detected using the detector. Labeling enables proteins present at low concentration to more easily be detected and enhances reproducibility by increasing signal-to-noise ratios. The detector can be used to detect proteins as separated within an electrophoretic cavity or after they are eluted from the cavity. The combination of labeling and detection also enables separated proteins to be quantified. The point in the overall method at which labeling is conducted depends in part on the particular electrophoretic methods being conducted as discussed more fully below. In general, however, labeling is typically conducted before a gel capillary electrophoretic separation is performed; whereas, labeling is normally conducted after capillary isoelectric focusing is performed rather than before. Labeling can also be used before a zone capillary electrophotesis separation is performed as a means to modify the net charge on the proteins and their relative electrophoretic mobilities.

As noted above, some of the more commonly used electrophoretic methods utilized in the present invention are capillary isoelectric focusing electrophoresis, capillary zone electrophoresis and capillary gel electrophoresis. Specific issues regarding the performance of these methods are described in the following sections.

Capillary Isoelectric Focusing Electrophoresis
(CIEF)

General

Isoelectric focusing is an electrophoretic method in which zwitterionic substances such as proteins are separated on the basis of their isoelectric points (pI). The pI is the pH at which a zwitterionic species such as a protein has no net charge and therefore does not move when subjected to an electric field. In the present invention, proteins can be separated within a pH gradient generated using ampholytes or other amphoteric substances within an electric field. A cathode is located at the high pH side of the gradient and an anode is located at the low pH side of the gradient.

Proteins introduced into the gradient focus within the pH gradient according to their isoelectric points and then remain there. General methods for conducting CIEF are described, for example, by Kilar, F., "Isoelectric Focusing in Capillaries," in *CRC Handbook on Capillary Electrophoresis: A Practical Approach*, CRC Press, Inc., chapter 4, pp. 95–109 (1994); and Schwartz, H., and T. Pritchett, "Separation of Proteins and Peptides by Capillary Electrophoresis: Application to Analytical Biotechnology," Part No. 266923 (Beckman-Coulter, Fullerton, Calif., 1994); Wehr, T., Rodriquez-Diaz, R., and Zhu, M., "Capillary Electrophoresis of Proteins," (Marcel Dekker, N.Y., 1999), which are incorporated herein by reference in their entirety.

System and Solutions

Because CIEF is primarily an equilibrium technique with low current densities, capillary heating typically is not a problem. Therefore, fairly large bore capillaries can be utilized. Suitable sizes include, but are not limited to, capillaries having internal diameters of 2–600 µm, although more typically capillaries having internal diameters of 25–250 µm are utilized. The use of relatively large bore capillaries means the method can use relatively high protein loads, which facilitates detection in the following dimension(s). This feature of CIEF makes the method well-suited for the initial or one of the early electrophoretic separations in the series. However, smaller diameter capillaries enable temperature to be controlled more carefully and, in some methods, result in improved signal detection (e.g., by laser induced fluorescence (LIF) detection of fluorescently labeled proteins).

The capillaries can have varying lengths. The length selected depends in part on factors such as the extent of separation required. Typically, the capillaries are about 10 to 100 cm in length, although somewhat shorter and longer capillaries can be used. While longer capillaries typically result in better separations and improved resolution of protein mixtures, longer capillaries also afford more opportunities for protein-wall interactions and lower field strength. Consequently, there tends to be an upper limit on capillary length beyond which resolution may be lost. Longer capillaries can be of particular use in resolving low abundance proteins. Further guidance on size and length of capillaries is set forth, for example, in Palmieri, R. and J. A. Nolan, "Protein capillary electrophoresis: Theoretical and experimental considerations for methods development," in: CRC Handbook of Capillary Electrophoresis: A Practical Approach, Chp. 13, pgs. 325–368 (CRC Press, Boca Raton, 1994).

Generally, the capillaries are composed of fused silica, although plastic capillaries and PYREX (i.e., amorphous glass) can be utilized in certain methods. As noted above, the capillaries do not need to have a round or tubular shape. Other shapes wherein the internal dimension between opposing faces is within the general range set forth in this section can also be utilized.

A variety of different anode and cathode solutions can be used. Common solutions include sodium hydroxide as the catholyte and phosphoric acid as the anolyte. Similarly, a number of different ampholytes can be utilized to generate the pH gradient, including numerous commercially available ampholyte solutions (e.g., BioLyte, Pharmalyte and Servalyte). The selection of ampholytes and the breadth of the ampholyte-gradient can impact the resolution that is achieved by CIEF methods. Narrow ampholyte gradients increase the number of theoretical plates in the separation and can be beneficial for higher resolution separations over narrow pI ranges.

CIEF methods utilized in the separations of the invention can be conducted in capillaries containing polymeric matrices or in free solution (i.e., no gel or other polymeric matrix). Polymer matricies are typically added to slow electroosmotic flow; however, in some instances, inclusion of polymeric matrices can restrict movement of larger proteins (see, e.g., Patton, 26). The use of free solutions is preferable in such cases possibly in combination with other methods (e.g., capillary coatings, gel plugs, or induced electric fields) to control the electroosmotic flow.

Sample Preparation

Typically protein samples to be electrophoresed by CIEF are denatured prior to loading the sample into the capillary. This ensures that the same proteins all have the same charge and thus identical proteins focus at the same location rather than potentially at multiple zones within the capillary. Denaturants (e.g., urea), non- and zwitterionic-surfactants (e.g., IGEPAL CA-630 or 3-[{3-cholamidopropyl}dimethylammonio]-1-propane sulfonate) can also be used to suppress protein-wall and/or protein-protein interactions that can result in protein precipitation. Another advantage of denaturing the proteins prior to electrophoresis is that the results can be used in comparisons with archival data typically obtained under denaturing conditions.

A typical denaturing buffer includes urea and a nonionic or zwitterionic surfactant as denaturants; a reducing agent (e.g., dithiothreitol (DTT) or mercaptoethanol) is typically included to reduce any disulfide bonds present in the proteins. Other denaturants besides urea that can be used include, but are not limited to, thiourea and dimethylformamide (DMF). Generally, guanidine hydrochloride is not utilized as a denaturant because of the very high ionic strength it imparts to a sample. Exemplary neutral detergents include polyoxyethylene ethers ("tritons"), such as nonaethylene glycol octylcyclohexyl ether ("TRITON" X-100), polyglycol ethers, particularly polyalkylene alkyl phenyl ethers, such as nonaethylene glycol octylphenyl ether ("NONIDET" P-40 or IGEPAL CA-630), polyoxyethylene sorbitan esters, such as polyoxyethylene sorbitan monolaurare ("TWEEN"-20), polyoxyethylene ethers, such as polyoxyethylene lauryl ether ($C_{12}E_{23}$) ("BRIJ"-35), polyoxyethylene esters, such as 21 stearyl ether ($C_{18}E_{23}$) ("BRIJ"721), N,N-bis[3-gluconamido-propyl]cholamide ("BIGCHAP"), decanoyl-N-methylglucamide, glucosides such as octylglucoside, 3-[{3-cholamidopropyl}dimethylammonio]-1-propane sulfonate and the like.

The optimal amount of denaturant and detergent depends on the particular detergent used. In general the denaturing sample buffers contain up to 10 M urea (more typically 4–8 M and most typically 6–8 M). Specific examples of suitable buffers (and denaturants and nonionic surfactants for inclusion therein) include those described by Hochstrasser et al.[5] and O'Farrell[6]. Denaturation is typically advanced by heating for 10 min at 95° C. prior to injection into the capillary. Adjustments in the denaturing sample buffers are made as necessary to account for any electroosmotic flow or heating effects that occur (see, e.g., Kilar, F., "Isoelectric Focusing in Capillaries," in *CRC Handbook on Capillary Electrophoresis: A Practical Approach*, CRC Press, Inc., chapter 4, pp. 95–109 (1994)).

The amount of protein within a sample can vary and, as noted above, depends in part of the size of the capillary used. In general, the capillary is loaded with 0.1 to 5.0 mg of total protein. Samples can be spiked with one or more known pI standards to assess the performance of the method.

Elution

A variety of techniques can be utilized to elute or withdraw electrophoretic medium containing resolved proteins out from the capillary, but these methods fall into three general categories: hydrodynamic elution, electroelution and control of electroosmotic flow.

Hydrodynamic/Pressure Elution

Hydrodynamic or pressure elution involves applying pressure (or pulling a vacuum) via an appropriate pump connected with one end of the capillary (see, e.g. Kilar, F., "Isoelectric Focusing in Capillaries," in *CRC Handbook on Capillary Electrophoresis: A Practical Approach*, CRC Press, Inc., chapter 4, pp. 95–109 (1994)). However, hydrodynamic elution can cause band broadening and loss of resolution due to the parabolic flow profile that is formed in the capillary.

Electroelution

Electroelution, the other major approach, encompasses a variety of techniques and in general involves altering the solution at the anode and/or cathode to change some parameter (e.g., pH, ionic strength, salt concentration) of the electrophoretic medium in the separation cavity sufficiently to effect elution.

Salt Mobilization

One electroelution approach involves addition of a salt to the catholyte or anolyte, the salt having a non-acidic or non-basic counterion of the same charge as the acidic or basic species within the reservoir to which the salt is added so that the counterion migrates from the reservoir into the capillary. Since electrical neutrality must be maintained within the capillary, the movement of the counterion into the capillary results in a reduction of the concentration of protons or hydroxide within the capillary, and thus the pH is either raised or lowered. The theoretical basis for this type of mobilization is described by. S. Hjerten, J.-L. Liao, and K. Yao, J. Chromatogr., 387: 127 (1987). For example, if the catholyte is sodium hydroxide (i.e., the basic species is hydroxide) then a salt having a negatively charged counterion other than hydroxide is added, for example sodium chloride. Movement of chloride ion into the capillary reduces the local concentration of hydroxide within the capillary, thereby decreasing the pH. As another example, if the anolyte is phosphoric acid, then a salt having a counterion other than a proton is added, for example sodium phosphate. In this instance, movement of sodium ion into the capillary reduces the local concentration of protons within the capillary thereby increasing the pH. As the pH is lowered or raised within regions of the capillary due to the presence of the added counterion, elution occurs since the ampholytes, and the focused proteins, migrate to the newly-defined pH regions corresponding to their isoelectric points. It has been shown that both the type and concentration of salt used for mobilization has impact on the resolution of eluted protein peaks [R. Rodriguez-Diaz, M. Zhu, and T. Wehr, J. Chromatogr. A, 772:145 (1997)]. In particular, the addition of sodium tetraborate instead of sodium chloride to the catholyte results in greatly increased resolution of separated proteins.

pH Mobilization

Another technique, referred to herein as "pH mobilization" can also be utilized to elute proteins during CIEF. In this approach, an additive is added to either the anode or cathode solution to alter the pH of the solution. Unlike salt mobilization, however, the additive does not contribute a mobile counterion that moves into the capillary. Here, the elution occurs as a result of the pH gradient being redefined by the pH of one or both of the reservoirs; therefore, proteins with pI's that fall outside of this redefined pH gradient are eluted into either the anode or cathode reservoirs. Typically, the technique for cathodic mobilization would proceed as follows. Once the proteins are focused in an exemplary pI range of 3–10 using phosphoric acid as the anolyte and sodium hydroxide as the catholyte, the cathodic capillary end is immersed into a reservoir containing a solution that has a pH slightly less than 10, for example 50 mM imidazole (pKa 7) which has a pH of 9.85. The proteins are then allowed to refocus in the capillary, recognizable by a stabilization of the current through the capillary, the pI range now being defined by 3–9.85. Any proteins with an isoelectric point of 9.85 to 10 are eluted into the catholyte. The process can be repeated with catholyte containing a species that reduces the pH to slightly less than 9.85. In a stepwise fashion, the pH can be continued to be reduced to pH 7, thereby collecting separated proteins in fractions that span the range of 7–10. At this point, anodic mobilization can proceed by replacing the anolyte with acids of increasing pKa to selectively increase the pH from 3 to 7, thereby collecting fractions in the acidic range (pH 3–7). The number of fractions can vary depending on the desired fractionation resolution. Typically, these fractions are defined by differences of 0.05–0.5 pH units.

The technique of pH mobilization can be useful for protein samples containing a high concentration of one or more proteins that may cause uneven spatial gradients inside the capillary. Using pH mobilization, only those proteins with isoelectric points below or above the pI range that is defined by the reservoir pH's are eluted. This elution would, therefore, be reproducible regardless of differences in the shape of the capillary pH gradient or-he presence of uneven spatial gradients inside the capillary.

Electroosmotic Flow (EOF)

Regulating the magnitude of electroosmotic flow (EOF) significantly affects the preceding electroelution methods (see supra) and is another means by which resolved proteins can be selectively withdrawn upon conclusion of an isoelectric focusing separation. EOF is generated by the ionization of silanol functionalities on the surface of a silica capillary. Such ionization results in a layer of protons in the electrophoretic medium at the surface of the silica capillary. Once an electric field is applied, the layer of protons essentially constitutes a positively charged column of fluid which migrates toward the cathode, thereby causing bulk flow of the electrophoretic medium within the capillary. Apparent velocity of analytes is equal to the sum of the electroosmotic flow and their electrophoretic mobility. Thus, by controlling EOF, one can control or regulate the rate at which proteins move through the capillary. In CIEF methods, generally EOF should be controlled to allow proteins within an injected sample sufficient time to focus before the proteins begin eluting from the capillary.

A variety of techniques can be utilized to regulate EOF. One approach involves coating the walls of capillaries with various agents. For example, EOF along glass silicate surfaces can be substantially reduced by silanizing them with a neutral silane reagent that masks a substantial percentage of surface silanol groups (e.g., polyacrylamide, polyethylene glycol and polyethylene oxide). The magnitude of EOF can be further controlled by using silanizing reagents that include positively or negatively charged groups. Positively charged coatings can be used to nullify surface negative charges to give a net surface charge of zero, so that EOF approaches zero. Coatings with higher positive charge densities can be used to reverse the direction of EOF for charged surface materials. This can be useful for slowing the net migration rates of positively charged sample species. Conversely, negatively charged coatings can be used to impart to or increase the magnitude of the negative charge on surfaces, so as to increase the net migration rates of negatively charged species. Representative positively charged coatings include trialkoxysilanes with polyethyleneimine, quaternized polyethyleneimine, poly(N-ethylaminoacrylamide) and chitosans, for example. Representative negatively charged coatings include trialkoxysilanes with carboxylate and sulfonate containing materials such as poly(methylglutamate) and 2-acrylamido-2-methylpropanesulfonate polymers, for example. It will be recognized that charged coatings can also effectively reduce sample adsorption, especially for samples having the same charge polarity as the coating.

The separation medium can also include soluble agents for dynamically coating the walls of the separation cavity, to help reduce EOF during electrophoresis. Such soluble coating agents include quaternary ammonium-containing polymers, methyl cellulose derivatives, cellulose acetate, polyethylene oxide, chitosan, polyvinyl alcohol, polyethylene glycol, polyethylenimine, and polyethylene oxide-polypropylene oxide-polyethylene oxide triblock copolymers, for example. Typically, soluble coating agents are included at concentrations of about 0.05% to about 4%, and more typically of about 1% to about 2%.

EOF and sample absorption can also be adjusted by including suitable reagents in the. separation medium and running buffers. For example, negative surface charges can be masked by including a cationic additive in the medium, such as metal amine complexes, amines and polyamines such as propylamine, triethylamine, tripropylamine, triethanolamine, putrescine, spermine, 1,3-diaminopropane, morpholine, and the like. Zwitterionic species comprising both negatively and positively charged groups that are isoelectric at the pH of electrophoresis can also be used, such as trialkylammonium propyl sulfonates, where alkyl is methyl, ethyl, propyl, and longer alkyl chains.

Another approach involves the generation of a current that opposes EOF. Typically, this is accomplished by applying a thin film of metal (e.g., iridium tin oxide or copper) to an external surface of the capillary. Application of current to the film generates a relatively small induced current within the capillary to reverse the EOF (see, e.g., Schasfoort, R. B. M., Schlautmann, S., Hendrikse, J., and van den Berg, A., "Field-Effect Flow Control for Microfabricated Fluidic Networks," Science, 286:942–945 (1999)).

Figure 2B:
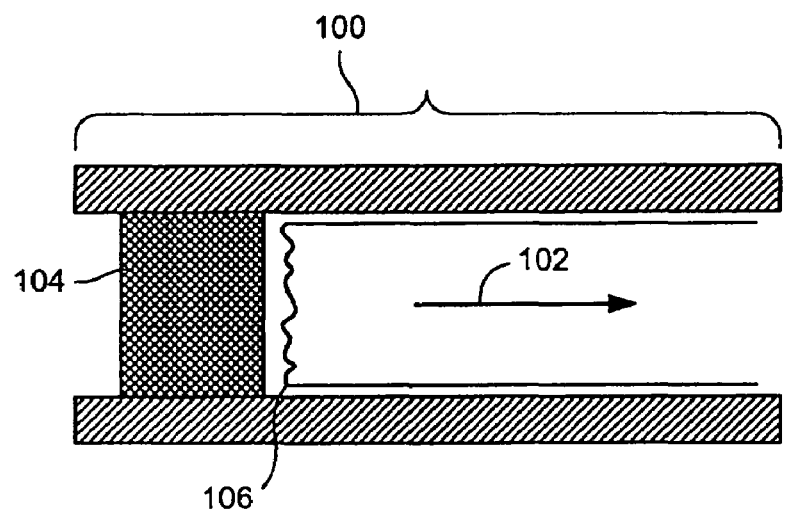
FIG. 2B is a cross-sectional view of a capillary showing the orientation of a porous plug inserted into the capillary to control electroosmotic flow in certain methods of the invention.

Placing a porous plug at a location upstream from where sample is introduced (upstream referring to a direction opposite the flow of proteins through the capillary) can also be utilized to control EOF. An example illustrating the location of the plug is illustrated in FIG. 2B where the capillary 100 extends from the anode reservoir (not shown) at one end and the cathode reservoir at the other end (not shown). Protein migration is in the direction of arrow 102 (i.e., from the anode to cathode direction).

As can be seen, the porous plug 104 is positioned to be upstream of the trailing edge 106 of the sample once introduced into the capillary 100. The porous plug 104 is typically formed of a polymeric material and remains relatively stationary during electrophoretic runs. Examples of suitable materials from which the plug can be formed include polymerized acrylamide with diacrylamide crosslinkers and agarose. Although not intending to be bound by any particular theory, the porous plug 104 appears to function as a momentum transfer barrier by blocking replacement of bulk fluid that in the absence of the plug 104 would move toward the cathode reservoir.

In some methods, such as those containing large amounts of protein and/or a large number of different proteins, EOF should be reduced to very low levels to allow proteins the opportunity to focus before the electrophoretic medium begins eluting from the capillary due to EOF. In certain methods an EOF of $0.5 \times 10^{-6}$ cm$^2$/V-s (at pH 8.6, and 25 mM TRIS-phosphate) has been found to allow ample time for the necessary focusing of proteins before sample elutes from the capillary. Methods described above can reduce EOFs to these levels.

Thus, the foregoing approaches enable fractions to be collected according to different criteria. Electroelution techniques, for example, can be used to collect fractions having a defined pH range. EOF elution and pressure elution, in contrast, can be used to separate fractions according to time of elution. Other techniques can also be utilized to elute resolved proteins after CIEF (see, e.g. Kilar, F., "Isoelectric Focusing in Capillaries," in *CRC Handbook or Capillary Electrophoresis: A Practical Approach*, CRC Press, Inc., chapter 4, pp. 95–109 (1994)). The controlled elution techniques are useful for enhancing reproducibility, an important factor in comparative and diagnostic methods. Such techniques also provide improved tolerance of high abundance proteins as compared to methods relying on spatial separation.

Capillary Zone Electrophoresis (CZE)

General

Capillary zone electrophoresis is an electrophoretic method conducted in free solution without a gel matrix and results in the separation of molecules such as proteins based upon their intrinsic charge-to-mass ratio. One advantage to CZE methods is the ability to run with solvent systems that would normally be incompatible with typical water soluble gel matrices. Nonaqueous or water miscible solvent systems can be used to improve the solubility of hydrophobic and membrane bound proteins that would normally not be resolved by gel electrophoretic methods. General methods for conducting the method are described, for example, by McCormick, R. M. "Capillary Zone Electrophoresis of Peptides," in *CRC Handbook of Capillary Electrophoresis: A Practical Approach*, CRC Press Inc., chapter 12, pp. 287–323 (1994); Jorgenson, J. W. and Lukacs, K. D., *J. High Resolut. Chromatogr. Commun.*, 4:230 (1981); and Jorgenson, J. W. and Lukacs, K. D., *Anal. Chem.* 53:1298 (1981)), each of which is incorporated by reference in its entirety.

System and Solutions

In general, the capillaries described above for CIEF are also suitable for conducting CZE methods. Often the capillaries have internal diameters of about 50 to 100 microns. Buffer composition and pH can significantly influence separations since separations in CZE are based upon charge-to-mass ratios and the charge of a protein is dependent upon the pH of the surrounding solution. At the extremes of pH (i.e., below 2 and above 10) it is typically difficult to achieve resolution of proteins because all residues are either fully protonated or deprotonated and many proteins have a similar number of acidic and basic residues per unit mass. Selectivity is typically enhanced at intermediate pH. For proteins having a relatively high percentage of acidic residues, selectivity can often be enhanced near pH 4.5. For those proteins having a high concentration of basic residues, selectivity can be enhanced near pH 10.

In CZE, solutions at the anode and cathode are typically the same. The buffer utilized can be essentially any buffer, the choice of buffer being controlled in part by the pH range at which the electrophoretic method is conducted and its influence on the detector noise. Examples of useful buffers at low pH include, but are not limited to, phosphate and citrate; useful buffers at high pH include Tris/Tricine, borate and CAPS (3-(cyclohexylamino)-1-propane sulfonic acid). Further guidance regarding suitable buffers and buffer additives is described by McCormick, R. M. "Capillary Zone Electrophoresis of Peptides," in *CRC Handbook of Capillary Electrophoresis: A Practical Approach*, CRC Press Inc., chapter 12, pp. 287–323 (1994).

Elution

Elution can be accomplished utilizing some of the same methods described above for CIEF, namely pressure and EOF. As with CIEF, controlling EOF can be important in certain methods to prevent electrophoretic medium containing protein from eluting from the capillary before the proteins within the loaded sample have had an opportunity to separate. EOF can be controlled using the same methods utilized for controlling EOF in CIEF methods (e.g., coating the internal walls of the capillary, using a porous plug and generating an induced field to counteract EOF). Regulating and carefully selecting the pH and ionic strength of the electrophoretic medium is another technique that can be used. Because EOF results from ionization of the silanol groups on the interior capillary surface, by conducting CZE at relatively low pH (e.g., pH 2–5, more typically about pH 3–4) the number of silanol groups that are ionized is reduced. Such a reduction reduces EOF. To prevent sample elution prior to complete separation, in certain analyses the EOF should be reduced to <$1\times10^{-4}$ cm$^2$/V-s (at pH 8.6 and 25 mM TRIS-phosphate buffer). EOFs of this level can be obtained using the methods just described.

Another approach that is described more fully below in the detection and labeling section is to label proteins in the sample prior to injecting the sample containing the protein into the capillary. By selecting labels that preferentially react with certain functional groups such as amino or carboxyl groups, the charge-to-mass ratio of certain proteins can be altered. Such alterations can improve the resolution of proteins during electrophoresis as well as improve their detectability. (See Examples 1 and 2 below).

Capillary Gel Electrophoresis (CGE)

General

Capillary gel electrophoresis refers to separations of proteins accomplished by sieving through a gel matrix, resulting in the separation of proteins by size. In one format, proteins are denatured with sodium dodecyl sulfate (SDS) so that the mass-to-charge ratio is determined by this anionic surfactant rather than the intrinsic mass-to-charge ratio of the protein [50, 2]. This means that proteins can be separated solely on the basis of size without charge factoring into the degree of separation. The application of general SDS PAGE electrophoresis methods to capillary electrophoresis (CGE) is described, for example, by Hjertén, S., "Free zone electrophoresis," *Chromatogr. Rev.*, 9:122 (1967).

System and Solutions

The type of capillaries and their size are generally as described above for CZE. A variety of different buffers can be used, including commercially available buffers such as the "eCAP SDS" buffers manufactured by Beckman (see, also, 51, 30, 9 and 5). Various buffer additives can be utilized to increase resolution. Such additives, include, but are not limited to, small amounts of organic solvents, such as N,N-dimethylformamide, cyclohexyldiethylamine, dimethoxytetraethylene glycol and other polyols (e.g., ethylene glycol and polyethylene glycol) (see, e.g., [21] and [3]). The use of such solvents can improve the solubility of proteins in aqueous solution and enhance protein stability against thermal denaturation, [52] depress the electroosmotic flow in CZE and CGE [53], alter the electrical double-layer thickness at the capillary wall to inhibit protein binding interactions [47] and increase the viscosity of the running buffer which depresses the electroosmotic flow. Solvents utilized should be compatible with the polymer matrix inside the capillary.

Isotachophoresis (IPE) can be used in certain methods to increase resolution of proteins. For a general discussion of IPE, see, for example, B. J. Wanders and Everaerts, F. M., "Isotachophoresis in Capillary Electrophoresis," in *CRC Handbook of Capillary Electrophoresis: A Practical Approach*, chap. 5, pp. 111–127 (1994), which is incorporated by reference in its entirety. The velocity of a charged molecule moving through a capillary under a constant field strength depends on its relative mobility, which is a function of the mass/charge of the molecule, temperature, and viscosity of the medium through which it is moving. However, in the absence of an adequate concentration of highly mobile ions upstream of the sample ions, all the ions eventually have to migrate at the speed of the slowest ion once the electric field reaches a steady-state inside the capillary. This condition causes the anions to stack in order of their relative mobilities at the interface of the leading and terminating buffers.

Under SDS denaturing conditions, all the proteins present in the sample have nearly identical mass/charges. By using a higher mass/charge anion in the terminal buffer, one can force the proteins to move at a constant slow speed through the capillary. This has two effects. First, proteins "stack" at the terminal edge of the leading buffer increasing their effective concentration inside the capillary. Second, any separation between proteins is based on their size. Therefore, the use of a hybrid IPE-CGE method in which the IPE is used for sample "stacking" can improve the resolution possible in the subsequent CGE separation in some methods.

Various terminal buffer systems can be utilized in conjunction with IPE methods. In one system, ε-aminocaproic acid (EACA) is used as the terminal electrolyte because it has a high mass/charge at high pH (>6). Tris(hydroxyethyl) aminomethane (TRIS) citrate at 0.05M is used as the leading buffer at pH=4.8 and as an intermediate stacking buffer at pH=6.5. The sample proteins initially "stack" because EACalif. has a very low mobility in the pH 6.5 stacking buffer, but once the protein "stack" and EACA reach the lower pH leading buffer, the mobility of the EACalif. surpasses that of the proteins and separation commences (see, e.g., [57]). This system can be used to create a hybrid single column IPE-CPAGE system.

A 2 buffer system for IPE for the separation of proteins involves dissolving sample in 0.01M acetic acid, which is also used as the terminal electrolyte. The leading and background buffer was 0.02M triethylamine-acetic acid solution at pH 4.4. The sample in terminal buffer is sandwiched between the leading and background buffer. IPE continues until the background buffer overtakes the leading edge of the terminal buffer, at which point IPE stops and separation begins (see, e.g., [58]).

Another IPE approach that can be accomplished with any running buffer is to dissolve the sample in the running buffer but diluted to a lower ionic strength. This causes an increase in the electrical resistance in the capillary where the sample plug is loaded and correspondingly faster movement of the ions present in the sample matrix to running buffer boundary. The optimal ionic strength difference between the sample matrix and the running buffer is typically about 10-fold (see, e.g., [43]).

Elution

In general, the discussion of elution for CZE applies to CGE. Elution can be accomplished utilizing pressure and EOF. As with CIEF and CZE, controlling EOF can be important in certain methods to prevent electrophoretic medium containing protein from eluting before the proteins within the applied sample have had an opportunity to separate. The methods described supra for CIEF and CZE can be used to control EOF at desired levels. To prevent sample elution prior to complete separation, in certain analyses the EOF should be reduced to $<1 \times 10^{-4}$ cm$^2$/V-s (at pH 8.6 and 25 mM TRIS-phosphate buffer). EOF can be reduced to this range, for example, by controlling the pH of the buffer, by generation of a counteracting induced field, capillary coatings and a porous gel plug.

Combination with Detection Steps

In some instances, the proteins separated by the methods of the invention are subjected to further analysis by mass spectroscopy. In such instances, particular labels can be utilized to enhance separation of mass fragments into certain parts of the mass spectrum. Suitable labels in such methods are set forth more fully in U.S. patent application Ser. No. 09/513,395 (now U.S. Pat. No. 6,379,971) filed on Feb. 25, 2000. This application is incorporated herein by reference in its entirety.

Quantitation of detected signals can be performed according to established methods. Peak height and peak area are typically used to quantify the amount of each resolved protein in the final electrophoretic dimension. In some methods, the peak height, peak width at the half height, peak area, and elution time for each peak are recorded. Peak shape (determined as the height to width ratio) can be used as a measure of the quality of the separation method. The resolution potential of the method can be determined by correlating the MW of the protein with the elution time (see, e.g., [30] and [11]). By dividing the overall run time by the average peak width of each protein an estimate of the total number of proteins that can be resolved by the method (e.g., proteins separated by at least one peak width can be considered a "resolved" protein) can be obtained. The reproducibility of the MW estimate can be determined by two methods. In one method, the apparent MW determined for each protein in three replicate runs by establishing the standard curve from one run and using that curve to determine the MW based on elution time from each subsequent run are compared (see, e.g., [21]). In the second approach, the overall error of the method is determined from the standard deviation in the slope of the standard curve created using the data from all three replicate runs.

The labeling and direct detection approaches that can be used with certain methods of the invention can yield improved reproducibility in the quantification of relative protein expression levels compared to the staining and imaging methods utilized in conventional 2-D gels. Staining techniques frequently yield poorly quantitative results because varying amounts of stain are incorporated into each protein and the stained protein must be detected and resolved against the stained background of the gel or electroblotting substrate. Moreover, since the methods utilize combinations of electrophoretic methods, an electropherogram that is directly comparable to archived 2-D gel image data is still obtained. This means that the methods remain comparable to 2-D gel information as compared to other non-electrophoretic based separations (e.g., LC/MS/MS).

Exemplary Systems

The methods of the invention are amenable to a variety of different electrophoretic methods. The controlled elution techniques whereby defined fractions are separated spatially, physically or by time, and the labeling and detection methods can be utilized in a number of different electrophoretic techniques. As noted above, the number of electrophoretic methods linked in series is at least two, but can include multiple additional electrophoretic methods as well. In some instances, each electrophoretic method in the series is different; whereas, in other instances certain electrophoretic methods are repeated at different pH or separation matrix conditions.

Despite the general applicability of the methods, as noted above CIEF, CZE and CGE methods are specific examples of the type of electrophoretic methods that can be utilized according to the methods of the invention. In certain methods, only two methods are performed. Examples of such methods include a method in which CIEF is performed first followed by CGE. Labeling is typically performed after CIEF with detection subsequent to elution of protein from the CGE capillary. Protein eluting from the CIEF capillary can be detected using a UV/VIS spectrometer at 214 or 280 nm, for example. In another system, the first method is CZE and the final method is CGE. With this arrangement, labeling is typically performed prior to CZE to enhance resolution as described supra. Detection generally is not performed until the completion-of the final electrophoretic separation. A third useful approach involves initially conducting CIEF followed by CZE and CGE. Labeling for such a system is typically done after CIEF and before CZE. Labeling at this point in the overall method avoids alteration of CIEF patterns (see supra) and allows for greater resolution during CZE. Detection is generally conducted at the conclusion of CGE (i.e., with resolved protein within the capillary or after the proteins have eluted from the capillary). These are specific examples of systems that can be utilized; it should be understood that the invention is not limited to these particular systems. Other configurations and systems can be developed using the techniques and approaches described herein.

Samples

The methods of the invention can be used with a wide range of sample types. Essentially any protein-containing sample can be utilized with the methods described herein. The samples can contain a relatively small number of proteins or can contain a large number of proteins, such as all the proteins expressed within a cell or tissue sample, for example.

Samples can be obtained from any organism or can be mixtures of synthetically prepared proteins or combinations thereof. Thus, suitable samples can be obtained, for example, from microorganisms (e.g., viruses, bacteria and fungi), animals (e.g., cows, pigs, horses, sheep, dogs and cats), hominoids (e.g., humans, chimpanzees, and monkeys) and plants. The term "subject" as used to define the source of a sample includes all of the foregoing sources, for example. The term "patient" refers to both human and veterinary subjects. The samples can come from tissues or tissue homogenates or fluids of an organism and cells or cell cultures. Thus, for example, samples can be obtained from whole blood, serum, semen, saliva, tears, urine, fecal material, sweat, buccal, skin, spinal fluid, tissue biopsy or necropsy and hair. Samples can also be derived from ex vivo cell cultures, including the growth medium, recombinant cells and cell components. In comparative studies to identify potential drug or drug targets (see infra), one sample can be obtained from diseased cells and another sample from non-diseased cells, for example.

Sample preparation for the different electrophoretic techniques is set forth above. If the sample contains cellular debris or other non-protein material that might interfere with separation during electrophoresis, such materials can be removed using any of a variety of known separation techniques including, for example, forcibly exuding the sample through sieve material, filtration and centrifugation. Samples whose ionic strength is particularly high can be desalted using established techniques such as dialysis and dilution and reconcentration.

In some instances in which the sample contains salts or other interfering components, buffer exchange can be performed to improve IPE "stacking" and improve reproducibility in elution times and peak shapes for electrophoretic methods. One useful way to implement dialysis to remove interfering compounds is to collect fractions directly in the dialysis chamber of a spin dialysis tube (Gilson/Amicon). The sample can then be spin dialyzed and resuspended in a 10-fold dilution of the running buffer to be utilized in the next electrophoretic separation of the series. This procedure has the advantages that: (1) in the case of CIEF, larger volumes of buffers can be used during electroelution of each fraction without diluting the proteins in each fraction, (2) the same sample volume can be used for each fraction injected into the second dimension and (3) smaller more concentrated sample volumes can be used in the second dimension because the dialyzed proteins can be resuspended in almost any buffer volume after dialysis.

Variations

The methods of the invention need not end with the last electrophoretic method of the series. As illustrated in FIG. 1, resolved proteins can be further analyzed by non-electrophoretic methods. Examples of such methods include infrared spectroscopy, nuclear magnetic resonance spectroscopy, UV/VIS spectroscopy and complete or partial sequencing. Coupling the current electrophoretic-based method to various mass spectroscopy (MS) methods is one specific example of further analysis that can be conducted. A variety of mass spectral techniques can be utilized including several MS/MS methods and Electrospray-Time of Flight MS methods (see, e.g., [61], [62], [63], and [64]). Such methods can be used to determine at least a partial sequence for proteins resolved by the electrophoretic methods such as a protein sequence tag (for a discussion or protein sequence tags, see, e.g., [65] and [66]). Further discussion regarding combining the electrophoretic separations described herein with mass spectral analysis is set forth in U.S. provisional application 60/130,238 entitled "Rapid and Quantitative Protein Expression and Sequence Determination," filed Apr. 20, 1999, and to which this application claims benefit and which is incorporated by reference in its entirety. Other mass spectral methods that can be combined with the methods of the present invention are described in U.S. patent application Ser. No. 09/513,486 (now U.S. Pat. No. 6,537,432), filed on Feb. 25, 2000, both being incorporated by reference in their entirety.

Microfluidic Systems

In another variation, the capillaries are part of or formed within a substrate to form a part of a microfluidic device that can be used to conduct the analyses of the invention on a very small scale and with the need for only minimal quantities of sample. In these methods, physical fractions of samples typically are not collected. Instead, resolved proteins are separated spatially or by time. Methods for fabricating and moving samples within microfluidic channels or capillaries and a variety of different designs have been discussed including, for example, U.S. Pat. Nos. 5,858,188; 5,935,401; 6,007,690; 5,876,675; 6,001,231; and 5,976,336, all of which are incorporated by reference in their entirety.

Figure 3A:
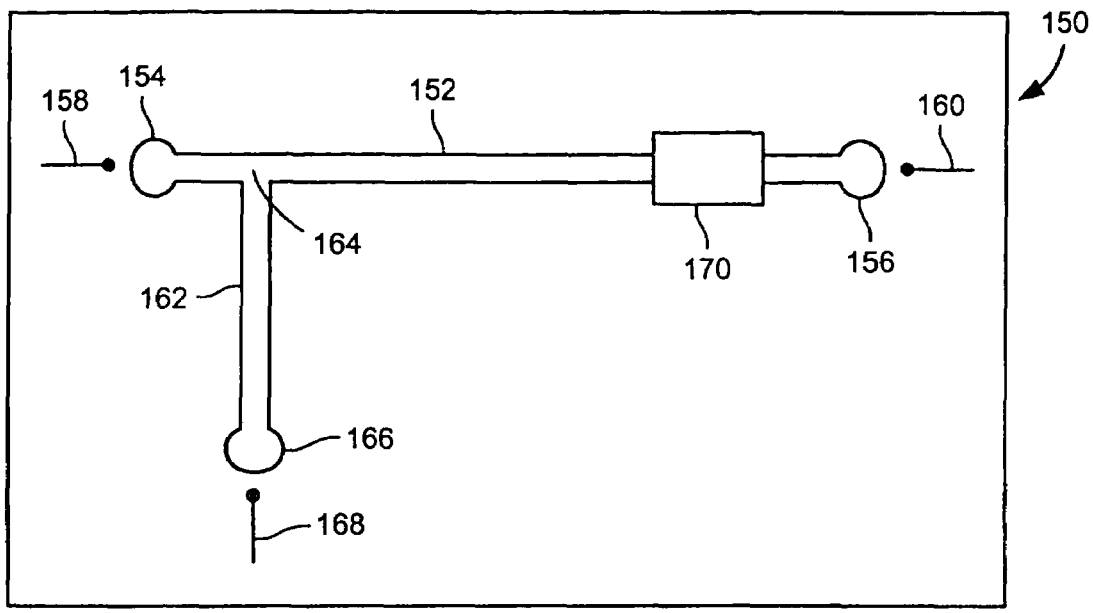
FIGS. 3A and 3B are top-views of certain elements of microfluidic devices that can be utilized to conduct certain electrophoretic methods of the invention.

An example of a general system 150 that can be used with the methods of the present invention is depicted in FIG. 3A. The capillaries or channels are typically formed or etched into a planar support or substrate. A separation capillary 152 extends from an anode reservoir 154 containing anolyte to a cathode reservoir 156. The anode reservoir 154 and the cathode reservoir 156 are in electrical contact with an anode and cathode 158, 160, respectively. A sample injection channel 162 runs generally perpendicular to the separation capillary 152 and one end intersects at an injection site 164 slightly downstream of the anode reservoir 154. The other end of the sample injection capillary 162 terminates at a sample reservoir 166, which is in electrical communication with a sample reservoir electrode 168. A detector 170 is positioned to be in fluid communication with electrophoretic medium passing through the separation capillary 152 and is positioned downstream of the sample injection site 164 and typically somewhat upstream of the cathode reservoir 156. In this particular configuration, fractions are withdrawn into the cathode reservoir. Movement of electrophoretic medium through the various channels is controlled by selectively applying a field via one or more of the electrodes 158, 160 168. Application of a field to the electrodes controls the magnitude of the EOF within the various capillaries and hence flow through them.

Figure 3B:
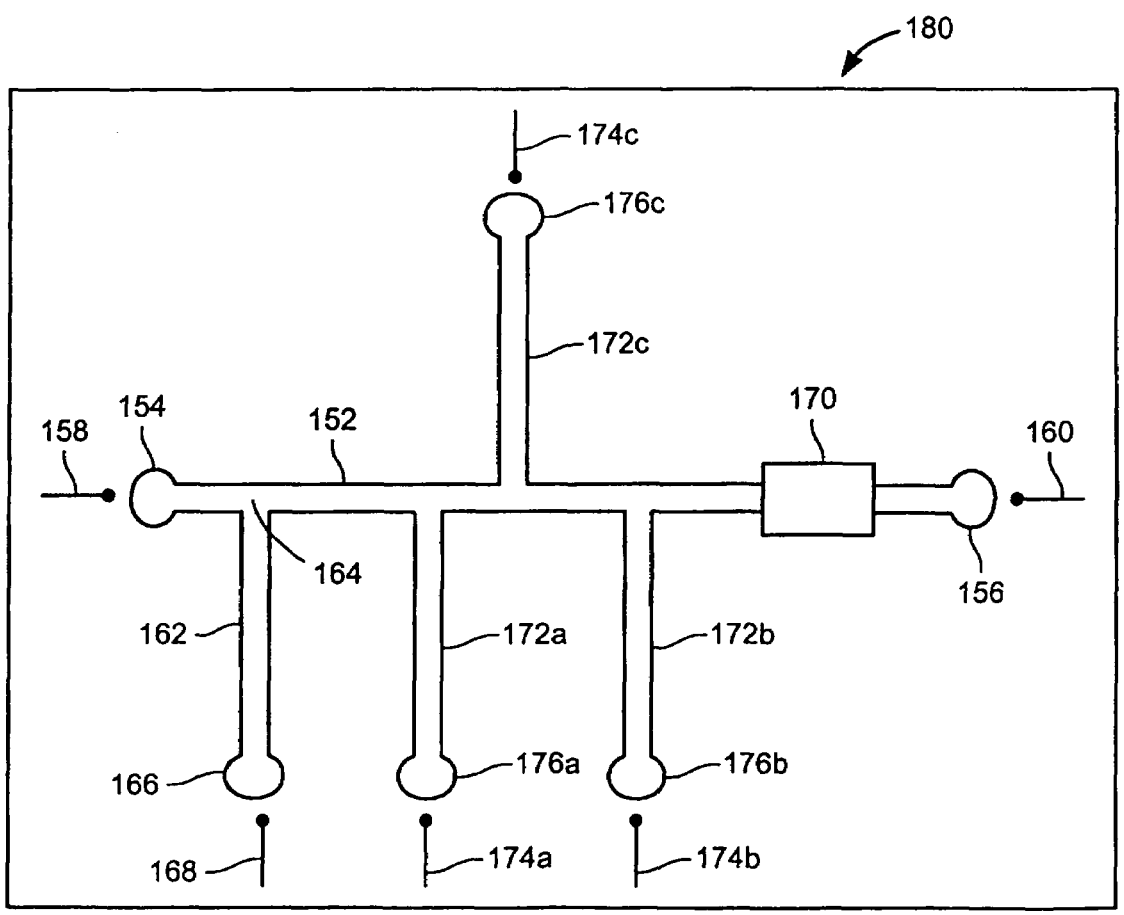

An example of another configuration is illustrated in FIG. 3B. This system 180 includes the elements described in the system shown in FIG. 3A. However, in this arrangement, spacially or temporally resolved fractions can be withdrawn at multiple different locations along the separation capillary 152 via exit capillaries 172a, 172b and 172c. Each of these capillaries includes a buffer reservoir 176a, 176b, 176c, respectively, and is in electrical communication with electrodes 174a, 174b, 174c, respectively. Movement of electrophoretic medium along separation capillary 152 and withdrawal of fractions therefrom into the exit capillaries 172a, 172b and 172c can be controlled by controlling which electrodes along the separation capillary 152 and which of the exit capillary electrodes are activated. Alternatively, or in addition, various microfluidic valves can be positioned at the exit capillaries 172a, 172b and 172c to control flow. Typically, additional detectors are positioned at the various exit capillaries 172a, 172b and 172c to detect protein in fractions withdrawn into these capillaries.

The configuration illustrated in FIG. 3B can be used in a number of different applications. One example of an application for which this type of system is appropriate is a situation in which the type of samples being examined have been well characterized. If for example, certain fractions of proteins of interest have been previously established to fractionate at a particular location in the separation capillary 152, then the exit capillaries 172a, 172b and 172c can be positioned at those locations to allow for selective removal of the protein fraction(s) of interest.

In still another configuration, multiple exit capillaries branch from the end of the separation capillary 152 near the cathode reservoir 156, each exit capillary for withdrawing and transporting separate fractions. In this configuration also, withdrawal of fractionated protein from the separation capillary can be controlled by regulating EOF within the various capillaries and/or by microfluidic valves.

Other components necessary for conducting an electrophoretic analysis can be etched into the support, including for example the reservoirs, detectors and valves discussed supra.

Substrates

The substrate upon which the capillary or micro-channel network of the analytical devices of the present invention are formed can be fabricated from a wide variety of materials, including silicon, glass, fused silica, crystalline quartz, fused quartz and various plastics, and the like. Other components of the device (e.g., detectors and microfluidic valves) can be fabricated from the same or different materials, depending on the particular use of the device, economic concerns, solvent compatibility, optical clarity, mechanical strength and other structural concerns. Generally, the substrate is manufactured of a non-conductive material to allow relatively high electric fields to be applied to electrokinetically transport the samples through the various channels.

In the case of polymeric substrates such as plastics, the substrate materials can be rigid, semi-rigid, or non-rigid, opaque, semi-opaque or transparent, depending upon the use for which the material is intended. Plastics which have low surface charge when subjected to the electric fields of the present invention and thus which are of particular utility include, for example, polymethylmethacrylate, polycarbonate, polyethylene terephthalate, polystyrene or styrene copolymers, polydimethylsiloxanes, polyurethane, polyvinylchloride, polysulfone, and the like.

Devices which include an optical or visual detector are generally fabricated, at least in part, from transparent materials to facilitate detection of components within the separation channel by the detector.

Channel Structure/Formation

The size and shape of the channels or capillaries formed in the substrate of the present devices can have essentially any shape, including, but not limited to, semi-circular, cylindrical, rectangular and trapezoidal. The depth of the channels can vary, but tends to be approximately 10 to 100 microns, and most typically is about 50 microns. The channels tend to be 20 to 200 microns wide.

Manufacturing of the channels and other elements formed in the surface of the substrate can be carried out by any number of microfabricating techniques that are known in the art. For example, lithographic techniques may be employed in fabricating glass or quartz substrates, for example, using established methods in the semiconductor manufacturing industries. Photolithographic masking, plasma or wet etching and other semiconductor processing technologies can be utilized to create microscale elements in and on substrate surfaces. Alternatively, micromachining methods, such as laser drilling, micromilling and the like, can be utilized. Manufacturing techniques for preparing channels and other elements in plastic have also been established. These techniques include injection molding techniques, stamp molding methods, using for example, rolling stamps to produce large sheets of microscale substrates, or polymer microcasting techniques, wherein the substrate is polymerized within a micromachined mold.

Further guidance regarding other designs and methods for using such microfluidic devices such as described above can be found, for example, in U.S. Pat. Nos. 5,858,188; 5,935,401; 6,007,690; 5,876,675; 6,001,231; and 5,976,336, all of which are incorporated by reference in their entirety.

Mass Spectrometric Detection and Sequencing

In a variation, the buffer system can be altered in the last separation step, through the use of volatile buffer salts, organic solvents, and ephemeral surfactants to make the eluent compatible with subsequent mass spectrometric analysis. A buffer salt consists of organic and inorganic species that may accept or reject a proton to create an ionic species. Volatile buffer salts consist of a subset of buffer salts that are substantially vaporized into the gas phase upon evaporation of water, where substantially vaporized is typically defined as greater than 50% mass volatility, more typically greater than 80% mass volatility, and most typically 90–100% mass volatility. Illustrative examples include salts selected from the groups of ammonium, alkyl- and aryl-ammonium, pyridinium, alkyl- and aryl-phosphonium, and alkyl- and aryl-sulfonium cations, and the groups of alkyl- and aryl-sulfonates, alkyl- and aryl-phosphonates, alkyl- or aryl-borates, alkyl- or aryl-carboxylates, halogenated carboxylates, carbonate, and bicarbonate anions. Illustrative non-typical examples include salts with at least one component selected from the group of sodium and potassium anions, or halide and sulfate anions.

An ephemeral surfactant consists of an anionic, cationic, neutral, or zwitterionic surfactant that are substantially vaporized into the gas phase or decompose to form species that substantially vaporize into the gas phase upon evaporation of water, where substantially vaporized is typically defined as greater than 50% mass volatility, more typically greater than 80% mass volatility, and most typically 90–100% mass volatility. Illustrative anionic examples include anmnonium dodecyl sulfate, alkyl- or aryl-ammonium dodecylsulfate, and alkylammonium perfluoroalkylcarboxylates. Illustrative cationic examples include alkylammonium carboxylate or alkylphosphonium carboxylate species where at least one alkyl chain is typically 5–30 carbons long and more typically 6–15 carbons long and most typically 10–14 carbons long.

Preliminary Separation By Non-Electrophoretic Technique

The methods can also include an initial separation by a non-electrophoretic technique prior to commencing the electrophoretic separations. Essentially any type of technique capable of separating proteins can be utilized. Suitable methods include, but are not limited to, fractionation in a sulfate gradient, HPLC, ion exchange chromatography and affinity chromatography. (Please list other techniques that you consider important).

Exemplary Utilities

The methods and apparatus of the invention can be utilized to detect, characterize and/or identify many proteins (e.g., hundreds or thousands of proteins in some methods) by controlling elution of fractionated proteins and utilizing various labeling and detection techniques. Consequently, the methods have multiple utilities including, but not limited to, various analytical applications (e.g., monitoring certain protein levels as a function of external stimuli, or detecting specific proteins in complex compositions for identification purposes), clinical applications (e.g., detecting and/or monitoring compositions of normal and diseased cells and tissues, diagnosing or monitoring disease, testing drug candidates for therapeutic efficacy and toxicity testing) and molecular biology and genetic research (e.g., characterizing or monitoring molecular expression levels of gene products and determining the effects of the addition, mutation, deletion or truncation of a particular gene). In general, the methods and apparatus have utility in proteome research.

More specifically, the invention can be used in the development of protein databases in which, for example, proteins expressed under particular conditions are isolated, quantified, and identified. Using the controlled elution and detection methods described herein, certain methods can be utilized to determine and catalog a variety of chemical and physical characteristics of the resolved proteins, including, but not limited to, pI, and/or apparent molecular weight and/or relative abundance of proteins within a sample. This information can be further cross referenced with a variety of information regarding the source of the sample and the method by which it was collected. Examples of such information include genus, species, age, race, sex, environmental exposure conditions, subject's health, tissue type, method of sample collection and method of sample preparation prior to electrophoresis.

The methods also have value in a variety of comparative studies that can be utilized to identify potential drug targets and/or candidates. For example, the methods can be utilized to identify proteins that are differentially expressed in diseased cells as compared to normal cells. Such differentially expressed proteins can serve as targets for drugs or serve as a potential therapeutic. In a related fashion, the methods can be used in toxicology studies to identify proteins that are differentially expressed in response to particular toxicants. Such differentially expressed proteins can serve as potential targets or as potential antidotes for particular toxic compounds or challenges. The detection and labeling techniques of the invention can facilitate such investigations because these techniques enable even low abundance proteins to be detected and because enhanced reproducibility makes it easier to identify real differences in expression between different samples.

Proteomic studies using certain methods of the invention can detect mutations that result in premature termination of the gene transcript or in amino acid substitutions in the resulting gene product. The methods can also detect post translational modification events associated with disease that are not readily detectable or possible to detect using functional genomics. For example, proteomic methods can detect differences in protein folding, glycosylation patterns, phosphorylation events, and degradation rates.

The results of comparative studies are transferable to a variety of diagnostic applications. For example, the "marker" or "fingerprint" proteins identified during comparative studies as being characteristic of a particular disease can be used to diagnosis individuals to determine if they have the disease correlated with the marker. These markers can also be used in medical screening tests. Once such proteins have been identified, it is not necessary to examine all fractions. Instead, only those fractions potentially containing the marker proteins need be examined. The reproducibility of the methods facilitates such analyses. For systems integrated onto a chip or support (see supra), capillaries can be positioned at the appropriate locations along the separation cavity to withdraw only the relevant fractions potentially containing the marker protein(s) of interest.

As an example of a diagnostic application, proteomic analysis can be utilized in identifying diagnostic markers (e.g., cell surface antigens or serum proteins) for immunodiagnostic assays. Purified samples of putative diagnostic proteins are recovered during proteomic analysis, and can be used to generate antibodies having specific binding affinity to the proteins. Such antibodies can be used to understand the link between the marker protein and the disease through immunological staining to localize the protein in diseased cells or to rapidly screen patients for the presence of the protein, showing its statistical link to the disease.

The methods of the invention have further utility in conducting structure activity studies. For instance, the methods can be used to determine the effect that certain chemical agents or combination of agents have on protein expression patterns. Alterations to the agent or combination can then be made and protein expression reassessed to determine what effect if any the alteration has on protein expression. Such studies can be useful, for example, in making derivatives of a lead compound identified during initial drug screening trials.

III. Mass Spectroscopy Fragmentation

An aspect of the present invention resides in the development of a new nonproteolytic mass spectrometric method for protein sequencing. This method is conducted by labeling the N- or C-terminus of an intact protein with a unique mass tag, fragmenting the intact labeled protein in the ionization zone of a mass spectrometer (in-source fragmentation) and determining the sequence from the mass ladder of the resulting labeled peptide series. Labeled peptides are differentiated from unlabeled peptides by their unique mass signature in the resulting mass spectrum. In some embodiments, this process is accomplished in less than I min for a purified labeled protein, yielding a 500 to 1000-fold more rapid method than current MS/MS protein sequencing techniques.

The labeled proteins are highly fragmented in the ionization zone of the MS. This leads to increased ionization efficiency and volatility of the resulting labeled peptide fragment ions, relative to the parent protein, thus improving the overall detection sensitivity. The sequence is constructed from the low molecular weight end of the mass spectrum, providing greater absolute mass accuracy and more facile sequencing, including resolution of Q and K residues, from the resulting labeled peptide fragments.

The selection of an appropriate label for this technique requires consideration of several criteria. First, the label should be robust enough to survive the fragmentation conditions of the MS. Second, the label should also create a unique mass/charge (m/z) signature that is distinguishable from any unlabeled peptides generated from internal scissions of the protein backbone. Third, the label may also carry a hard charge to ensure that fragmentation produces high-abundance ions that include even uncharged N- and C-terminal residues. Example 6 using glycogen phosphorylase, carrying a natural N-terminal acetylation label, shows the generality of the technique.

In one aspect, the present invention provides a method for sequencing a portion of a protein, comprising:

(a) contacting a protein with a C-terminus or N-terminus labeling moiety to covalently attach a label to the C— or N-terminus of the protein and form a labeled protein; and (b) analyzing the labeled protein using a mass spectrometric fragmentation method to determine the sequence of at least the two C-terminus or two N-terminus residues.

In this aspect of the invention the protein can be obtained from essentially any source. Preferably, the protein is isolated and purified to be free of interfering components. The isolated protein can be contacted with a C-terminus or N-terminus labeling moiety to covalently attach a label to the C— or N-terminus of the protein to form a labeled protein, suitable for analysis by mass spectrometric fragmentation methods.

Labeled Proteins

The labeling of proteins with various agents in an aqueous or mixed aqueous/organic solvent milieu is known in the art and a wide range of labeling reagents and techniques useful in practicing the present invention are readily available to those of skill in the art. See, for example, Means et al., CHEMICAL MODIFICATION OF PROTEINS, Holden-Day, San Francisco, 1971; Feeney et al., MODIFICATION OF PROTEINS: FOOD, NUTRITIONAL AND PHARMACOLOGICAL ASPECTS, Advances in Chemistry Series, Vol. 198, American Chemical Society, Washington, D.C., 1982; Feeney et al., FOOD PROTEINS: IMPROVEMENT THROUGH CHEMICAL AND ENZYMATIC MODIFICATION, Advances in Chemistry Series, Vol. 160, American Chemical Society, Washington, D.C., 1977; and Hermanson, BIOCONJUGATE TECHNIQUES, Academic Press, San Diego, 1996.

Labeling can be conducted and PSTs determined from either the N- or C-terminal end of the protein. About 59–90% of eukaryotic proteins are N-terminal acetylated and are thus refractory to N-terminus labeling. However, the natural N-acetyl group of such proteins can sometimes be used as a label for purposes of this invention, but only where one or more of the amino acids within 4 residues of the N-terminus is ionizable (e.g., is a lysine, arginine, histidine, aspartic acid, or glutamic acid residue) or can be derivatized to be ionizable (e.g., tyrosine, serine, and cysteine residues). Accordingly, strategies to label either the N- or C-termini are provided to afford the greatest degree of sequencing ability for any given protein. Once a label is selected, a deconvolution algorithm can be modified to search for masses that correspond to any modified residues.

As noted above, the following considerations are relevant to the selection of a labeling agent:

i) the mass of the label is preferably unique and preferably shifts the fragment masses to regions of the spectrum with low background;

ii) the label preferably contains fixed positive or negative charges to direct remote charge fragmentation at the N- or C-terminus;

iii) the label is preferably robust under the fragmentation conditions and does not undergo unfavorable fragmentation;

iv) the labeling chemistry is preferably efficient under a range of conditions, particularly denaturing conditions, thereby reproducibly and uniformly labeling the N- or C-terminus;

v) the labeled protein preferably remains soluble in the MS buffer system of choice; and vi) the label preferably increases the ionization efficiency of the protein, or at least does not suppress it;

vii) the label may contain a mixture of two or more isotopically distinct species to generate a unique mass spectrometric pattern at each labeled fragment position.

In view of the label selection criteria, preferred labeling moieties are those that have a detection enhancement component, an ion mass signature component and a C-terminus or N-terminus reactive functional group. The reactive group can be directly attached to either or both of the other two label components.

In another embodiment, the reactive functional group is separated from one or both of the detection enhancement component and the ion mass signature component by a linker. The linker is preferably designed such that it is chemically stable and inert, and such that it allows efficient separation of the reactive group and at least one of the other two components of the tag Within a preferred embodiment of the invention, the linker is composed of a hydrocarbon chain or, most preferably, of a hydrocarbon chain linked to an aryl or heteroaryl ring and preferably provides additional separation between the ionizable group and the isothiocyanate group.

As will be understood by one of ordinary skill in the art, a virtually limitless array of hydrocarbon chains and modified hydrocarbon chains may be utilized within the present invention. Preferred hydrocarbon chains which are attached to the phenyl ring may be found in the family of alkanes, with particularly preferred linkers ranging from 2 carbon atoms to about 20 carbon atoms in length. Within a preferred embodiment of the invention, the linker is a phenethyl group.

IV. Label Composition and Linkage Chemistry

The present invention more generally embodies a chemical labeling moiety, comprising:

(i) a detection enhancement component.

(ii) a component that exhibits a unique ion mass signature in a mass spectrometer and imparts that signature to peptide fragments attached to the labeling moiety, and (iii) a component that binds the chemical agent covalently to the protein at specific positions, most preferably to the N-terminal amine or C-terminal carboxyl terminus of a protein.

In a variation of the method, the labeling moiety is (iv) attached to all the proteins in a mixture containing a plurality of proteins prior to at least one electrophoretic separation step.

In a variation of the method, the labeling moiety (v) alters the intrinsic (or native) charge on a protein, altering its separation coordinate in an electrophoretic mode.

In a variation of the method, the mass and/or charge of the labeling moiety (vi) is altered through the addition or cleavage of one or more components after detection and quantification in the final electrophoresis step and before its use in the mass spectrometer for partial sequencing of a protein.

In one embodiment the labeling moiety is used to quantitate the relative or absolute amount of a majority of proteins present in a mixed sample after separation of the labeled proteins during electrophoresis. Fluorescent, UV or visible dyes, and radioactive detection enhancement components are typical in this embodiment because of their intrinsically higher limits of detection. Fluorescent constituents are most typical for capillary electrophoresis separations because of the ready availability for fluorescent detectors for these electrophoresis units. Radioactive constituents are most typical for other modes electrophoresis separations because of the ready availability of phosphor screens and photographic film detection techniques for electrophoretic gels. The most typical detection enhancement component for MS detection is a charged or readily ionizable component. In a variation of the embodiment, more than one detection enhancement component may be employed on a labeling moiety.

In another embodiment, the labeling moiety imparts a unique mass signature to the protein or fragmented peptides derived from the protein in a mass spectrometer, such that the unique mass signature can be used to determine a partial protein sequence extending from the label. In a variation of the method, the label is attached to the N-terminus or C-terminus of the protein, allowing the determination of an N- or C-terminal protein sequence. In a variation of the method, the unique mass signature of the label is created as a function of the sum of the masses of the detection enhancement component and the reactive component after reaction with the protein. In a variation of the method, the unique mass signature is imparted by the use of mixtures of one or more isotopically enriched variants of the chemical moiety. In a variation of the method, the unique mass signature is imparted by mixtures of substantially identical chemical moieties that differ from each other by a chemical group substitution. In another embodiment, the same component may be used for both quantitative detection and to exhibit a unique ion mass signature. An example of such a constituent would be a napthalenic constituent (such as in dansyl chloride), which is both fluorescent and ionized in the mass spectrometer, but is not limited to a napthalenic constituent.

Reactive Groups

A third component of the labeling moiety is a functional group which is reactive with the N-terminus amino group, the C-terminus amino group or another constituent of the N- or C-terminus amino acid. The reactive functional group can be located at any position on the tag. For example, the reactive group can be located on an aryl nucleus or on a chain, such as an alkyl chain, attached to an aryl nucleus. When the reactive group is attached to an alkyl, or substituted alkyl chain tethered to an aryl nucleus, the reactive group is preferably located at a terminal position of an alkyl chain. Reactive groups and classes of reactions useful in practicing the present invention are generally those that are well known in the art of bioconjugate chemistry. Currently favored classes of reactions are those which proceed under relatively mild conditions in an aqueous or mixed aqueous/organic solvent milieu. Particularly preferred chemistries that target the primary amino groups in proteins (including the N-terminus) include, for example: aryl fluorides, sulfonyl chlorides, cyanates, isothiocyanates, immidoesters, N-hydroxysuccinimidyl esters, O-acylisoureas, chlorocarbonates, carbonylazides, aldehydes, and alkylamides and activated alkenes. Preferred examples of chemical constituents that react with the carboxyl groups of proteins are benzyl halides and carbodiimide, particularly if stabilized using N-hydroxysuccinimide. Both of these carboxyl labeling approaches are expected to label carboxyl containing amino acid residues (e.g., aspartate and glutamate) along with that of the C-terminus. These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

The reactive functional groups can be chosen such that they do not participate in, or interfere with, the reactions necessary to assemble the tag. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991. Table 1 provides a non-limiting list of a number of labeling moieties useful in the labels of the present invention.

TABLE 1

| Label | Source | Linkage Formed |
| --- | --- | --- |
| Amine Labeling | | |
| 2,4,6-trinitrobenzenesulfonic acid | Aldrich | Aryl amine |
| Lissamine ™ rhodamine B sulfonyl chloride | Molecular Probes | Sulfonamide |
| 2',7'-dichlorofluoroscein-5-isothiocyanate | Molecular Probes | Thiourea |
| 4,4-difluoro-5,7-dimethyl-4-bora-3a,4a-diaza-s-indacene-3-propionic acid, sulfosuccinimidyl ester | Molecular Probes | Amide |
| Nahthalene-2,3-dicarboxylaldehyde | Molecular Probes | Isoindole |
| Carboxyl Labeling | | |
| 5-(bromomethyl)fluorescein | Molecular Probes | Ester |
| N-cyclohexyl-N'-(4-(dimethylamino)naphthyl)carbodiimide | Molecular Probes | N-Acylurea |
| 1-ethyl-3-(3-dimethylaminopropyl)-carbodiimide hydrochloride with N-hydroxysuccinimide and 5-aminofluorescein | Pierce Aldrich Molecular Probes | Amide |

One of skill in the art will understand that labeling techniques are readily available for a number of the labeling moieties. An example of an N-terminus labeling group (dansyl chloride) and a C-terminus labeling group (carbodiimide) are provided as illustrative of the invention, with references to a more complete description of their use. The focus on these two labeling moieties is for clarity of illustration and does not limit the scope of the invention. Dansyl chloride undergoes a nucleophilic attack by the amines in proteins at alkaline pH, producing an aromatic sulfonamide. Sulfonyl chlorides, however, depending on the pH, can also react with secondary amines. The aromatic constituent enables spectroscopic (e.g., fluorescence) detection of the reaction product. Dansyl chloride also reacts with the ε-amino group of lysine. The pK differences between α- and ε-amines can be exploited to modify one of these groups preferentially to the other. Carbodiimides react with carboxyl groups to form an O-acylisourea intermediate that is highly unstable in aqueous solution but can be stabilized through the addition of N-hydroxysuccinimide resulting in the formation of an acid stable intermediate that can be made to react with primary amines, producing an amide. The carboxyl terminus, glutamate and aspartate residues are all targets for carboduimides in proteins at acidic pH (4.5–5). Carbodiimide chemistry is useful for labeling the C-terminus of protein. When carbodiimide chemistry is utilized, it is generally preferred that an excess of amine is added to the protein solution to inhibit crosslinking reactions. In another exemplary embodiment, a protein amine is labeled in a two-step process; an amine-containing fluorescent molecule is tethered to the protein through an N-hydroxysuccinimide intermediate of the protein or of a spacer arm attached to the protein.

Synthesis

Once the reactive group, linker, and ionizable groups have been selected, the final compound is synthesized by one of ordinary skill in the art utilizing standard organic chemistry reactions. A preferred compound for use within the present invention is PETMA-PITC, or an analogous agent. This compound retains the excellent characteristics of phenylisothiocyanate in the coupling. Furthermore, the compound performs well as a label in analytical methods because the electron structure of the phenyl ring is sufficiently separated from the quaternary ammonium group by the ethyl linker, thus allowing the isothiocyanate to react undisturbed by the quaternary ammonium group. Preparation of PETMA-PITC, C5 PETMA-PITC and PITC-311 are described in Aebersold et al., U.S. Pat. No. 5,534,440, issued Jul. 9, 1996. With the selection of a suitable labeling moiety, conditions for attaching the label to the protein should ensure that the N- or C-terminus of the protein is uniformly labeled and that the labeled protein remains soluble in appropriate CE and MS buffer systems. Typically, labeling will be carried out under denaturing conditions (e.g., surfactants or 8M urea). Surfactants and urea both suppress MS ionization. In a variation of the method, techniques that provide rapid clean up and transfer of the labeled protein sample to a suitable MS buffer should also be employed. In another variation of the method, these denaturants will naturally be resolved from the labeled proteins during electrophoretic separation steps conducted post-labeling.

In some instances, salts (e.g., TRIS and SDS) and urea present in electrophoresis buffers can suppress ionization of the labeled proteins and can generate small mass/charge ions that potentially confuse sequence analysis. Accordingly, spin dialysis procedures can be employed to rapidly exchange buffer systems prior to MS analysis. Alternatively, desalting columns (e.g., the ZipTip™ tip sold by Millipore) can be used for sample clean up and buffer exchange. Desalted samples can be resuspended in 0.1M ammonium bicarbonate as described by Wilm and Mann with minimal addition of methanol, or in 0.01M ammonium acetate buffer (with 0.1% formic acid) with minimal addition of acetonitrile as described by Mark. The coupling rates of the compound may be tested to ensure that the compound is suitable for sequencing polypeptides. In general, the faster the coupling rate the more preferred the compound. Coupling rates of between 2 and 10 minutes at 50° C. to 70° C. are particularly preferred. Similarly, fast reaction rates are also preferred, because exposure to the reaction mixture over an extended period of time might hydrolyze the peptide bonds, or lead to inefficient and irreproducible side reactions with the polypeptide residues, which could complicate mass spectral deconvolution.

In another preferred embodiment, one or more of the components of a protein mixture is reversibly attached to a solid support prior to the label being attached to a polypeptide. Various materials may be used as solid supports, including, for example, numerous resins, membranes or papers. These supports may additionally be derivatized to incorporate a cleavable functionality. A number of cleavable groups that may be used for this purpose include disulfides (—S—S—), glycol (—CH[OH]—CH[OH]—), azo (—N=N—), sulfone (—S[=O]—), and ester (—COO—) linkages (see, Tae, *Methods in Enzymology,* 91:580 (1983)). Supports which are particularly preferred include membranes such as Sequelon TM (Milligen/Biosearch, Burlington, Mass.). Representative materials for the construction of these supports include, among others, polystyrene, porous glass, polyvinylidinefluoride and polyacrylamide. In particular, polystyrene supports include, among others: (1) a (2-aminoethyl) aminomethyl polystyrene (see, Laursen, *J. Am. Chem. Soc.* 88: 5344 (1966)); (2) a polystyrene similar to number (1) with an aryl amino group (see, Laursen, *Eur. J. Biochem.* 20: 89 (1971)); (3) amino polystyrene (see, Laursen et al., *FEBS Lett.* 21: 67 (1972)); and (4)triethylenetetramine polystyrene (see, Horn et al., *FEBS Lett.* 36:285 (1973)). Porous glass supports include: (1) 3-aminopropyl glass (see, Wachter et al., *FEBS Lett.* 35: 97 (1973)); and (2)N-(2-aminoethyl)-3-aminopropyl glass (see, Bridgen, *FEBS Lett.* 50: 159 (1975)). Reaction of these derivatized porous glass supports with p-phenylene diisothiocyanate leads to activated isothiocyanato glasses (see, Wachter et al., supra). Polyacrylamide-based supports are also useful, including a cross-linked β-alanylhexamethylenediamine polydimethylacrylamide (see, Atherton et al., *FEBS Lett.* 64: 173 (1976)), and an N-aminoethyl polyacrylamide (see, Cavadore et al., *FEBS Lett.* 66: 155 (1976)).

One of ordinary skill in the art will readily utilize appropriate chemistry to couple the polypeptide to the solid supports described above (see, generally Machleidt and Wachter, Methods in Enzymology: [29] New Supports in Solid-Phase Sequencing 263–277 (1974). Preferred supports and coupling methods include the use of aminophenyl glass fiber paper with EDC coupling (see, Aebersold et al., *Anal. Biochem.* 187: 56–65 (1990)); DITC glass filters (see, Aebersold et al., *Biochem.* 27: 6860–6867 (1988) and the membrane polyvinylidinefluoride (PVDF) (Immobilon P TM, Milligen/Biosearch, Burlington, Mass.), along with SequeNet TM chemistry (see, Pappin et al., CURRENT RESEARCH IN PROTEIN CHEMISTRY, Villafranca J. (ed.), pp. 191–202, Academic Press, San Diego, 1990)).

In the practice of the present invention, attachment of the polypeptide to the solid support may occur by either covalent or non-covalent interaction between the polypeptide and solid support. For non-covalent attachment of the polypeptide to the solid support, the solid support is chosen such that the polypeptide attaches to the solid support by non-covalent interactions. For example, a glass fiber solid support may be coated with polybrene, a polymeric quaternary ammonium salt (see, Tarr et al., *Anal. Biochem.,* 84:622 (1978)), to provide a solid support surface which will non-covalently attach the polypeptide. Other suitable adsorptive solid phases are commercially available. For example, polypeptides in solution may be immobilized on synthetic polymers such as polyvinylidine difluoride (PVDF, Immobilon, Millipore Corp., Bedford, Mass.) or PVDF coated with a cationic surface (Immobilon CD, Millipore Corp., Bedford, Mass.). These supports may be used with or without polybrene. Alternatively, polypeptide samples can be prepared for sequencing by extraction of the polypeptide directly from polyacrylamide by a process called electroblotting. The electroblotting process eliminates the isolation of polypeptide from other peptides which may be present in solution. Suitable electroblotting membranes include Immobilon and Immobilon CD (Millipore Corp., Bedford, Mass.).

More recently, automated methods have been developed that allow chemistries to be performed on polypeptides immobilized on solid supports by non-covalent, hydrophobic interaction. In this approach, the samples in aqueous buffers, which may contain salts and denaturants, are pressure-loaded onto columns containing a solid support. The bound polypeptide is then pressure-rinsed to remove interfering components, leaving the bound polypeptide ready for labeling (see, Hewlett-Packard Product Brochure 23-5091-5168E (November, 1992) and Horn, U.S. Pat. No. 5,918,273 (Jun. 29, 1999).

The bound polypeptide is reacted under conditions and for a time sufficient for coupling to occur between the terminal amino acids of the polypeptide and the labeling moiety. The physical properties of the support may be selected to optimize the reaction conditions for a specific labeling moiety. For example, the strongly polar nature of the PETMA-PITC dictates covalent attachment of the polypeptide. Preferably, coupling with the amino groups of the polypeptide occurs under basic conditions, for example, in the presence of an organic base such as trimethylamine, or N-ethylmorpholine. In a preferred embodiment, the label is allowed to react with the bound peptide in the presence of 5% N-ethylmorpholine in methanol:water (75:25 v/v). Because of the mode of attachment, excess of reagent, coupling base and reaction by-products can be removed by very polar washing solvents prior to removal and sequencing of the labeled polypeptide by mass spectrometry. Various reagents are suitable as washing solvents, including, for example, methanol, water, mixtures of methanol and water, or acetone.

Less polar reagents, such as PITC-311, may be reacted with polypeptides attached to a sold support preferably by hydrophobic, non-covalent interactions. In this case, less polar washes are preferred, such as heptane, ethylacetate, and chloroform. Following the washing cycle, the labeled polypeptide is dissociated from the solid support by elution with solvent containing 50% to 80% of aqueous methanol or acetonitrile. When the labeling reaction is conducted entirely in solution phase, the reaction mixture is preferably submitted to a purification cycle, such as dialysis, gel permeation chromatography, and the like.

In another aspect, the present invention provides a method for sequencing a portion of a protein in a protein mixture, the method comprising:
(a) contacting the protein mixture with a C-terminus or N-terminus labeling moiety to covalently attach a label to the C— or N-terminus of the protein and form a labeled protein mixture;
(b) separating individual labeled proteins in the protein mixture; and
(c) analyzing the labeled proteins from step (b) by a mass spectrometric method to determine the sequence of at least two C-terminus or two N-terminus residues.

In one group of embodiments, the method further comprises:
(d) identifying the protein by using the sequence of at least two C-terminus or two N-terminus residues in combination with a separation coordinate of the labeled protein and the protein terminus location of the sequence to search predicted protein sequences from a database of gene sequence data.

Detectable Moieties

In another preferred embodiment, the protein is labeled with a moiety that enhances its detectability in, for example, protein purification and separation processes (e.g., electrophoresis). The detectable moiety can be detected by, for example, spectroscopy (e.g., UV/Vis, fluorescence, electron spin resonance (ESR), nuclear magnetic resonance (NMR) and the like), detection of radioactive isotopes, etc. When the protein is detected by UV/Vis, it is generally desirable to attach a chromophoric label to the protein (e.g., phenyl, napthyl, etc.). Similarly, for detection by fluorescence spectroscopy, a fluorophore is preferably attached to the protein. For ESR, the detectable moiety can be a free radical, such as a moiety including a nitroxide group. When the protein is detected by an NMR method, the detectable moiety can be enriched with an NMR accessible nuclei, such as fluorine, 13C, and the like.

In a presently preferred embodiment, the detectable moiety is a fluorophore. Many reactive fluorescent labels are commercially available from, for example, the SIGMA chemical company (Saint Louis, Mo.), Molecular Probes (Eugene, Oreg.), R&D systems (Minneapolis; Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and PE-Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

There is a great deal of practical guidance available in the literature for selecting an appropriate fluorophore for a particular tag, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties, for choosing reporter-quencher pairs (see, for example, Perlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In addition to fluorophores that are attached directly to a protein, the fluorophores can also be attached by indirect means. In an exemplary embodiment, a ligand molecule (e.g., biotin) is preferably covalently bound to the protein. The ligand then binds to another molecule (e.g., streptavidin), which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Presently preferred fluorophores of use in conjunction with the methods of the invention, include, for example, including fluoresceins, and rhodamine dyes. Many suitable forms of these compounds are widely available commercially with substituents on their phenyl moieties, which can be used as the bonding functionality for attachment of the fluorophore to a protein. Another group of preferred fluorescent compounds are the naphthylamines, having an amino group in the alpha or beta position. Included among such naphthylamino compounds are 1-dimethylaminonaphthyl-5-sulfonate, -1-anilino-8-naphthalene sulfonate and 2-p-toluidinyl-6-naphthalene sulfonate. Other donors include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Useful fluorescent detectable moieties can be made to fluoresce by exciting them in any manner known in the art, including, for example, with light or electrochemical energy (see, for example, Kulmala et al, *Analytica Chimica Acta* 386: 1 (1999)). Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

The fewer the processing steps between any separation technique and MS sequencing method, the faster that proteins can be identified, and the lower the cost of proteomic research. Typical electrophoresis buffers (e.g., Hochstrasser et al. and O'Farrel) contain components (e.g., tris(hydroxymethyl)aminomethane buffers and sodium dodecyl sulfate, that supress the ionization of proteins in the mass spectrometer. These components may be replaced with other more volatile components (e.g., morpholinoalkylsulfonate buffers and ephemeral surfactants) that do not suppress ionization in the MS. In another embodiment, the samples are diluted with ammonium bicarbonate or ammonium acetate buffer to provide a volatile proton source for the mass spectrometer. In another embodiment, a buffer exchange is conducted through by chromatographic orutangential flow dialysis as the sample is transported from the outlet of the separation process to the inlet of the MS.

Unique Mass Signature

The ion mass signature component is the portion of the labeling moiety which preferably exhibits a unique ion mass signature in mass spectrometric analyses. The ion mass signature component preferably includes a moiety that does not efficiently ionize under conditions in which proteins ionize (e.g., aromatic carbon compounds) as well as molecules that readily ionize under protein ionizing conditions to generate multiply charged ionic species. Both types of chemical entities can be used to shift the ion/mass signature of the amino acids and peptides attached to the label (after fragmentation of the labeled protein) in the mass spectrum. As a result, the labeled amino acids and peptides are readily distinguished from unlabeled amino acids and peptides by their ion/mass pattern in the resulting mass spectrum. In a preferred embodiment, the ion mass signature component imparts a mass to a protein fragment produced during mass spectrometric fragmentation that does not match the residue or typical fragmentation masses for any of the 20 natural amino acids.

As will be understood by one of skill in the art, spurious mass spectral peaks can arise not only from the fragmentation of unlabeled amino acids and peptides but also from impurities in the sample and/or matrix. In order to further increase the uniqueness of the ion mass signature of the label and to be able to identify desired labeled fragment peaks amongst this "noise," it is preferable to shift the labeled fragments to regions of less spectral noise by optimizing the mass of the label. For example, it is preferred that the label mass generate an ion greater than 100 amu and less than 700 amu. This may be done by increasing the molecular weight of a low molecular weight label or by increasing the number of charges on a high molecular weight label.

An alternative method for providing a m-ore unique mass signature to a labeling moiety is to incorporate stable isotopes in the label (see, for example, Gygi et al., *Nature Biotechnol.* 17: 994–999 (1999)). For example, by incorporating eight deuterium atoms into a labeling moiety and labeling the protein with a 50:50 mixture of the deuterated and nondeuterated label, the resulting singly-charged fragments that include the label are easily identified as equally intense doublets; one at the mass corresponding to the species with the nondeuterated label and the other at the mass corresponding to the species with the deuterated label with a spacing of 8 amu. In a preferred embodiment, the mass difference is more than about 1 amu at the single charge state. In the most preferred embodiment the mass difference is from about 4 to about 10 amu at the single charge state.

Another method for providing a more unique mass signature to a labeling moiety is to incorporate a mixture of alkyl and/or aryl substitutions onto the label, such that the corresponding set of fragment peaks is easily recognizable in the mass spectrum. For example, the protein can be labeled with a mixture of a label that contains a trimethyl ammonium group and the same label that contains a dimethylethylammonium group in place of the trimethyl ammonium group. This labeling moiety produces two fragment ion peaks for each amino acid in the sequence that differ by 14 amu from each other. It will be apparent to those skilled in the art that many such combinations can be derived.

Labeling Procedure

In some instances, salts (e.g., TRIS and SDS) and urea present in electrophoresis buffers can suppress ionization of the labeled proteins and can generate small mass/charge ions that potentially confuse sequence analysis. Accordingly, spin dialysis procedures can be employed to rapidly exchange buffer systems prior to MS analysis. Alternatively, desalting columns (e.g., the ZipTip™ tip sold by Millipore) can be used for sample clean up and buffer exchange. Desalted samples can be resuspended in 0.1M ammonium bicarbonate as described by Wilm and Mann with minimal addition of methanol, or in 0.01M ammonium acetate buffer (with 0.1% formic acid) with minimal addition of acetonitrile as described by Mark.

The coupling rates of the compound may be tested to ensure that the compound is suitable for sequencing polypeptides. In general, the faster the coupling rate the more preferred the compound. Coupling rates of between 2 and 10 minutes at 50° C. to 70° C. are particularly preferred. Similarly, fast reaction rates are also preferred, because exposure to the reaction mixture over an extended period of time might hydrolyze the peptide bonds, or lead to inefficient and irreproducible side reactions with the polypeptide residues, which could complicate mass spectral deconvolution. In another preferred embodiment, one or more of the components of a protein mixture is reversibly attached to a solid support prior to the label being attached to a polypeptide. Various materials may be used as solid supports, including, for example, numerous resins, membranes or papers. These supports may additionally be derivatized to incorporate a cleavable functionality. A number of cleavable groups that may be used for this purpose include disulfides (—S—S—), glycol (—CH[OH]—CH[OH]—), azo (—N=N—), sulfone (—S[=O]—), and ester (—COO—) linkages (see, Tae, *Methods in Enzymology*, 91:580 (1983)). Supports which are particularly preferred include membranes such as Sequelon TM (Milligen/Biosearch, Burlington, Mass.). Representative materials for the construction of these supports include, among others, polystyrene, porous glass, polyvinylidinefluoride and polyacrylamide. In particular, polystyrene supports include, among others: (1) a (2-aminoethyl) aminomethyl polystyrene (see, Laursen, *J. Am. Chem. Soc.* 88: 5344 (1966)); (2) a polystyrene similar to number (1) with an aryl amino group (see, Laursen, *Eur. J. Biochem.* 20: 89 (1971)); (3) amino polystyrene (see, Laursen et al., *FEBS Lett.* 21: 67 (1972)); and (4)triethylenetetramine polystyrene (see, Hom et al., *FEBS Lett.* 36:285 (1973)). Porous glass supports include: (1) 3-aminopropyl glass (see, Wachter et al., *FEBS Lett.* 35: 97 (1973)); and (2)N-(2-aminoethyl)-3-aminopropyl glass (see, Bridgen, *FEBS Lett.* 50: 159 (1975)). Reaction of these derivatized porous glass supports with p-phenylene diisothiocyanate leads to activated isothiocyanato glasses (see, Wachter et al., supra). Polyacrylamide-based supports are also useful, including a cross-linked β-alanyl-hexamethylenediamine polydimethylacrylamide (see, Atherton et al., *FEBS Lett.* 64: 173 (1976)), and an N-aminoethyl polyacrylamide (see, Cavadore et al., *FEBS Lett.* 66: 155 (1976)).

One of ordinary skill in the art will readily utilize appropriate chemistry to couple the polypeptide to the solid supports described above (see, generally Machleidt and Wachter, Methods in Enzymology: [29] New Supports in Solid-Phase Sequencing 263–277 (1974). Preferred supports and coupling methods include the use of aminophenyl glass fiber paper with EDC coupling (see, Aebersold et al., *Anal. Biochem.* 187: 56–65 (1990)); DITC glass filters (see, Aebersold et al., *Biochem.* 27: 6860–6867 (1988) and the membrane polyvinylidinefluoride (PVDF) (Immobilon P T M, Milligen/Biosearch, Burlington, Mass.), along with SequeNet TM chemistry (see, Pappin et al., CURRENT RESEARCH IN PROTEIN CHEMISTRY, Villafranca J. (ed.), pp. 191–202, Academic Press, San Diego, 1990)).

In the practice of the present invention, attachment of the polypeptide to the solid support may occur by either covalent or non-covalent interaction between the polypeptide and solid support. For non-covalent attachment of the polypeptide to the solid support, the solid support is chosen such that the polypeptide attaches to the solid support by non-covalent interactions. For example, a glass fiber solid support may be coated with polybrene, a polymeric quaternary ammonium salt (see, Tarr et al., *Anal. Biochemn.*, 84:622 (1978)), to provide a solid support surface which will non-covalently attach the polypeptide. Other suitable adsorptive solid phases are commercially available. For example, polypeptides in solution may be immobilized on synthetic polymers such as polyvinylidine difluoride (PVDF, Immobilon, Millipore Corp., Bedford, Mass.) or PVDF coated with a cationic surface (Immobilon CD, Millipore Corp., Bedford, Mass.). These supports may be used with or without polybrene. Alternatively, polypeptide samples can be prepared for sequencing by extraction of the polypeptide directly from polyacrylamide by a process called electroblotting. The electroblotting process eliminates the isolation of polypeptide from other peptides which may be present in solution. Suitable electroblotting membranes include Immobilon and Immobilon CD (Millipore Corp., Bedford, Mass.).

More recently, automated methods have been developed that allow chemistries to be performed on polypeptides immobilized on solid supports by non-covalent, hydrophobic interaction. In this approach, the samples in aqueous buffers, which may contain salts and denaturants, are pressure-loaded onto columns containing a solid support. The bound polypeptide is then pressure-rinsed to remove interfering components, leaving the bound polypeptide ready for labeling (see, Hewlett-Packard Product Brochure 23-5091-5168E (November, 1992) and Horn, U.S. Pat. No. 5,918,273 (Jun. 29, 1999).

The bound polypeptide is reacted under conditions and for a time sufficient for coupling to occur between the terminal amino acids of the polypeptide and the labeling moiety. The physical properties of the support may be selected to optimize the reaction conditions for a specific labeling moiety. For example, the strongly polar nature of the PETMA-PITC dictates covalent attachment of the polypeptide. Preferably, coupling with the amino groups of the polypeptide occurs under basic conditions, for example, in the presence of an organic base such as trimethylamine, or N-ethylmorpholine. In a preferred embodiment, the label is allowed to react with the bound peptide in the presence of 5% N-ethylmorpholine in methanol:water (75:25 v/v). Because of the mode of attachment, excess of reagent, coupling base and reaction by-products can be removed by very polar washing solvents prior to removal and sequencing of the labeled polypeptide by mass spectrometry. Various reagents are suitable as washing solvents, including, for example, methanol, water, mixtures of methanol and-water, or acetone.

Less polar reagents, such as PITC-311, may be reacted with polypeptides attached to a sold support preferably by hydrophobic, non-covalent interactions. In this case, less polar washes are preferred, such as heptane, ethylacetate, and chloroform. Following the washing cycle, the labeled polypeptide is dissociated from the solid support by elution with solvent containing 50% to 80% of aqueous methanol or acetonitrile. When the labeling reaction is conducted entirely in solution phase, the reaction mixture is preferably submitted to a purification cycle, such as dialysis, gel permeation chromatography, and the like.

In another aspect, the present invention provides a method for sequencing a portion of a protein in a protein mixture, the method comprising:
(a) contacting the protein mixture with a C-terminus or N-terminus labeling moiety to covalently attach a label to the C— or N-terminus of the protein and form a labeled protein mixture;
(b) separating individual labeled proteins in the protein mixture; and
(c) analyzing the labeled proteins from step (b) by a mass spectrometric method to determine the sequence of at least two C-terminus or two N-terminus residues.

In one group of embodiments, the method further comprises:
(d) identifying the protein by using the sequence of at least two C-terminus or two N-terminus residues in combination with a separation coordinate of the labeled protein and the protein terminus location of the sequence to search predicted protein sequences from a database of gene sequence data.

Separation

In a preferred embodiment, the tagging procedure is performed on a mixture of proteins. Following the tagging procedure the mixture of proteins is submitted to a separation process, which preferably, allows the separation of the protein mixture into discrete fractions. Each fraction is preferably substantially enriched in only one labeled protein of the protein mixture.

The methods of the present invention are utilized in order to determine the sequence of a polypeptide. Within preferred embodiments of the invention, the polypeptide is "substantially pure," which means that the polypeptide is about 80% homogeneous, and preferably about 99% or greater homogeneous. Many methods well known to those of ordinary skill in the art may be utilized to purify the polypeptide prior to determining its amino acid sequence. Representative examples include HPLC, Reverse Phase-High Pressure Liquid Chromatography (RP-HPLC), gel electrophoresis, chromatography, or any of a number of peptide purification methods (see, generally the series of volumes entitled METHODS IN PROTEIN SEQUENCE ANALYSIS). Even more preferred is the use of capillary electrophoresis and particularly, multi-dimensional capillary electrophoresis, such as that described in U.S. patent application Ser. No. 09/513,486 (now U.S. Pat. No. 6,537,432), filed on Feb. 25, 2000.

Although substantially pure polypeptides are preferably utilized within the methods described herein, it is also possible to determine the sequence of polypeptide mixtures. Briefly, in one embodiment, an algorithm is utilized in order to determine all of the hypothetical sequences with a calculated mass equal to the observed mass of one of the peptides in the mixture. See, Johnson et al., *Protein Science* 1:1083–1091(1992). These sequences are then assigned figures of merit according to how well each of them accounts for the fragment ions in the tandem mass spectrum of the peptide utilizing such algorithms, the sequence of polypeptides within the mixture may be readily determined. As described above, the methods herein are particularly useful for identifying proteins from a healthy or diseased tissue sample. In one group of embodiments, the methods are applied to both a mixture of proteins from a healthy tissue sample and a mixture of proteins from a diseased tissue sample. Accordingly, the protein mixtures used in this aspect of the invention can be obtained from essentially any source. Methods of isolating proteins from tissue samples are well known.

Within the present invention, the polypeptide with a derivatized terminal amino acid is sequenced by a mass spectrometer. Various mass spectrometers may be used within the present invention. Representative examples include, triple quadrupole mass spectrometers, magnetic sector instruments (magnetic tandem mass spectrometer, JEOL, Peabody, Mass.); ion-spray mass spectrometers, Bruins et al., *Anal. Chem.* 59: 2642–2647 (1987); electrospray mass spectrometers, Fenn et al., *Science* 246: 64–71 (1989); laser desorption time-of-flight mass spectrometers, Karas et al., *Anal. Chem.* 60: 2299–2301(1988), and a Fourier Transform Ion Cyclotron Resonance Mass Spectrometer (Extrel Corp., Pittsburgh, Mass.). Within a preferred embodiment, an electrospray mass spectrometer (Mariner™ model, PE Biosystems, Foster City, Calif.) is utilized to fragment the derivatized terminal polypeptide, and a time-of-flight detector with better than 50 ppm mass accuracy is used to determine the sequence from the masses of the labeled fragments.

One of skill in the art will appreciate that the sequence information obtained using the methods of the invention can be combined with other characteristics of the protein under analysis to even further reduce the number possible identities of the protein. Thus, in a preferred embodiment, the method of the invention combines information from a protein sequence tag with one or more other protein characteristics to identify the protein. Data that is useful to supplement the sequence data includes, but is not limited to, amino acid composition, the number and identity of specific residues (e.g. cysteine), cleavage information, proteolytic (e.g., tryptic) and or chemolytic peptide mass, subcellular location, and separation coordinates (e.g., retention time, pI, 2-D electrophoresis coordinates, etc.). Other forms of data characteristic of a particular protein or class of proteins that can be combined with information from the PSTs of the invention to identify a protein will be apparent to those of skill in the art. As the body of data characteristic of a particular protein becomes more comprehensive, proteins under analysis can be identified using shorter protein sequence tags.

Thus, in a further preferred embodiment, information regarding one or more characteristics of a protein is combined with information from a PST of about 4 amino acids in length, more preferably about 3 amino acids in length, more preferably still, about 2 amino acids in length is used to identify the protein. The materials, methods and devices of the present invention are further illustrated by the examples which follow. These examples are offered to illustrate, but not to limit the claimed invention.

Thus, in a further preferred embodiment, information regarding one or more characteristics of a protein is combined with information from a PST of about 4 amino acids in length, more preferably about 3 amino acids in length, more preferably still, about 2 amino acids in length is used to identify the protein.

It is to be understood that the above description is intended to be illustrative and not restrictive. Many embodiments will be apparent to those of skill in the art upon reading the above description. The scope of the invention should, therefore, be determined not with reference to the ab description, but should instead be determined with reference to the appended claims, along with the scope of equivalents to which such claims are entitled. The disclosures of all articles and references, including patent applications and publications are incorporated herein by reference.

The following examples are offered to illustrate, but no to limit the claimed invention.

EXPERIMENTAL EXAMPLES

Example 1 cZE Separation of Unlabeled Proteins

Each of five proteins (see Table 2) were obtained from Sigma-Aldrich and were suspended at 5 mg/ml in an aqueous denaturing sample buffer consisting of 25 mM tris (hydroxymethyl)aminomethane phosphate (pH 4.0), 0.5% by weight IGEPAL CA-630 (obtained from Sigma-Aldrich, Cat # I3021), and 1% by weight tris(2-carboxyethylphosphine)hydrochloride (obtained from Pierce, Cat # 20490ZZ). The protein samples were denatured in this sample buffer by heating at 95° C. for 15 min. Each of the five denatured protein samples were diluted into a cZE sample buffer to create a final solution consisting of 25 mM tris(hydroxymethyl)aminomethane phosphate buffer (pH 4.0), 8 M Urea, and a final concentration of 0.2 mg/ml of each of the five proteins. Control samples were also prepared of each denatured protein separately at 0.5 mg/ml final concentration in the same sample buffer.

TABLE 2

| | Protein Standards | | |
|---|---|---|---|
| Protein | Cat # | pI | MW (kDa) |
| Hen egg white conalbumin | C 0755 | 6.0, 6.3, 6.6 | 76.0 |
| Bovine serum albumin | B 4287 | 5.4, 5.5, 5.6 | 66.2 |
| Carbonic Anhydrase II | T 6522 | 4.5 | 21.5 |
| Rabbit muscle GAPDH | G 2267 | 8.3, 8.5 | 36.0 |
| Bovine ribonuclease A | R 5503 | 9.6 | 13.7 |

The mixed protein sample and each of the control samples were run by cZE in a 60 cm×75 µm fused silica capillary (Beckman Coulter). An 800 µm detection window was located 50 cm from the cathodic end of the capillary. A 160 nl sample volume was pressure injected at the cathodic end and the separations conducted at 500 V/cm in a 25 mM TRIS-phosphate and 8 M urea running buffer at pH 4.0. Protein detection was accomplished by UV adsorption at 214 nm.

Figure 4:
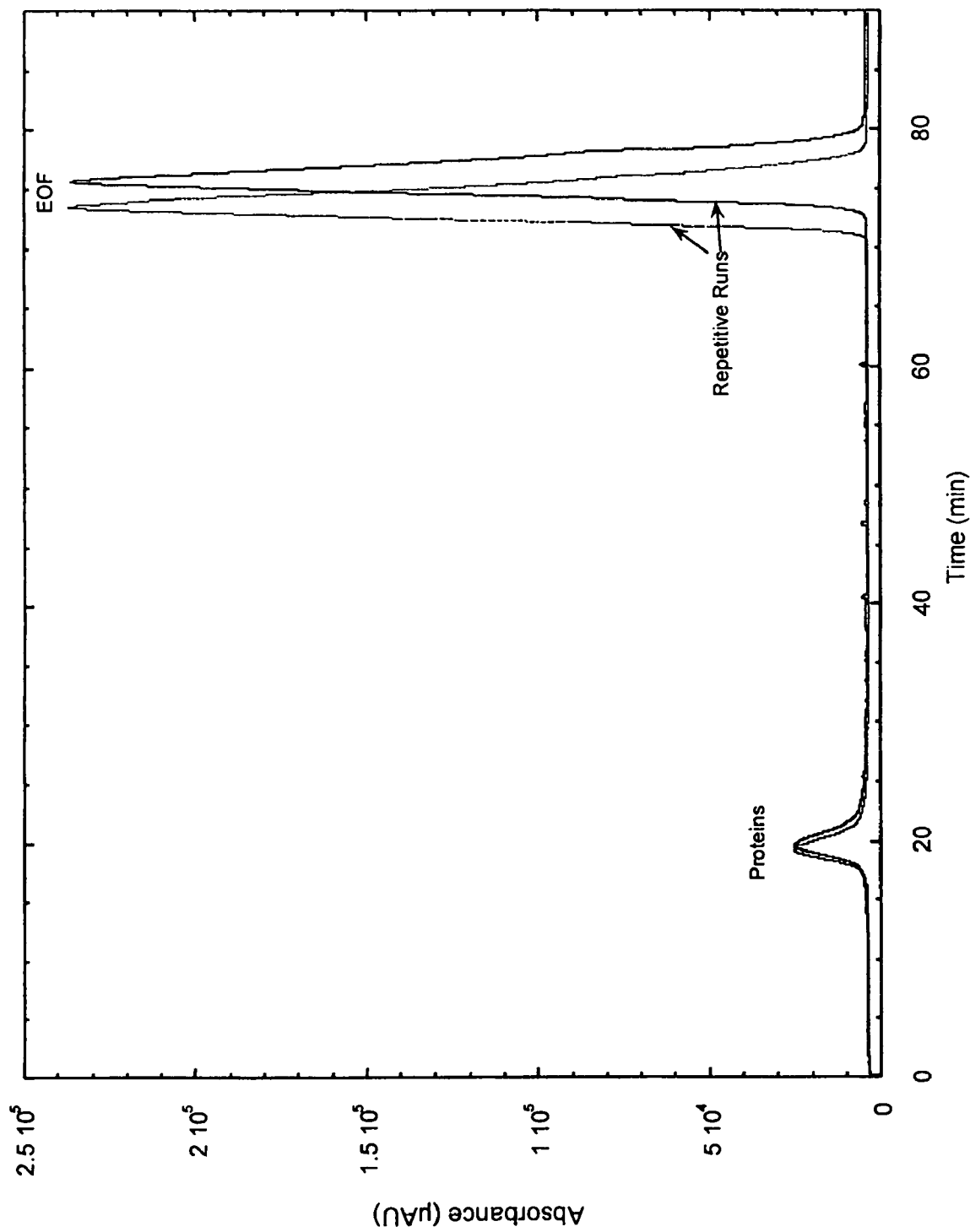
FIG. 4 is an electropherogram for a sample containing five unlabeled proteins (hen white conalbumin, bovine serum albumin, bovine carbonic anhydrase II, carbonic anhydrase II, rabbit muscle GAPDH, and bovine ribonuclease A) as obtained following electrophoresis by capillary zone electrophoresis. Absorbance was monitored at 214 nm. Under the conditions of this particular experiment (see Example 1) in which the proteins were unlabelled, the proteins were not resolved.
Figure 5:
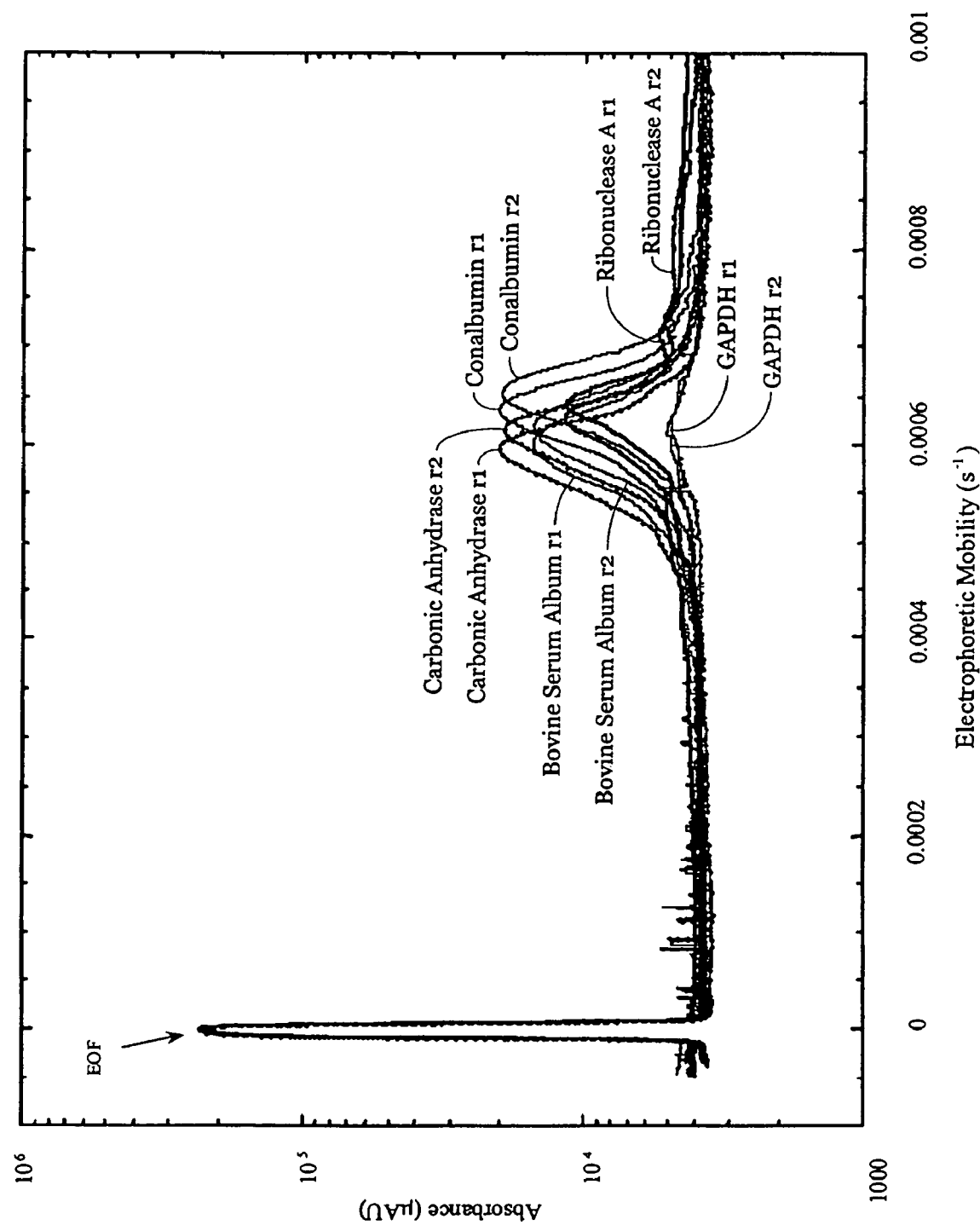
FIG. 5 is a plot of electrophoretic mobility for the five proteins listed in FIG. 4 under the same electrophoresis conditions as described in FIG. 4.
Figure 6:
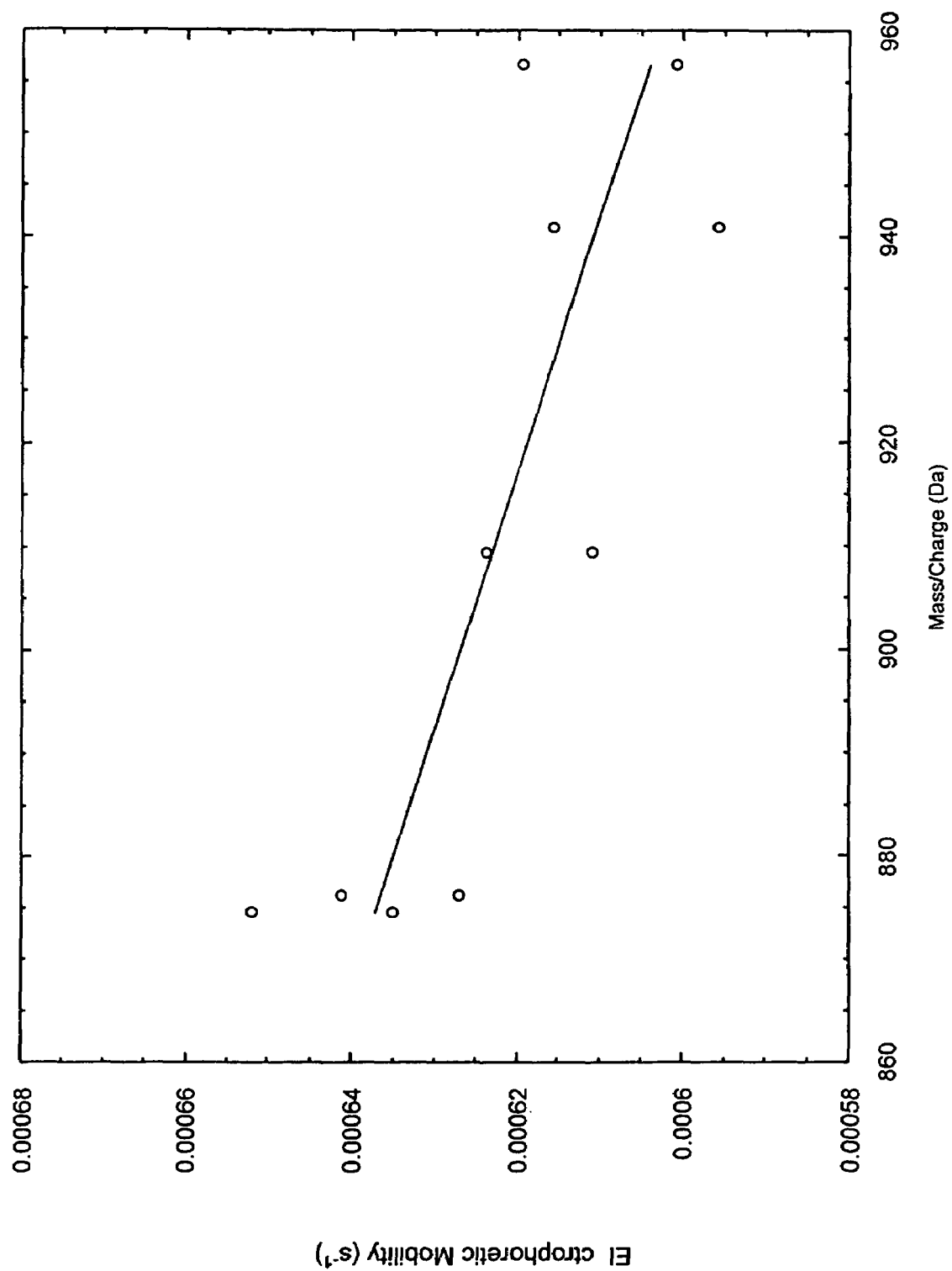
FIG. 6 is a plot showing the correlations between electrophoretic mobility and the predicted mass-to-charge ratio of the proteins at pH 4.0.

The individual unlabeled proteins were not resolved under these conditions (see FIG. 4). The electrophoretic mobility of each protein was determined from replicate runs of the individual protein controls (FIG. 5) and correlated with the predicted mass to charge ratio of the proteins at pH 4.0 (FIG. 6). The mass to charge ratio for each of the unlabeled proteins was determined from the published protein sequences obtained through Genbank in the manner described by Canter, C. R. and Schimmel, P. R., *Biophysical Chemistry*, W.H. Freeman and Co., New York, (1980), which is incorporated by reference in its entirety.

Example 2 cZE Separation of Labeled Proteins

Each of the five proteins described in Example 1 was suspended at 10 mg/ml in the same denaturing buffer described in Example 1 with the exception that an equal mass of sodium dodecyl sulfate was used in place of IGEPAL CA-630. The denatured protein samples were labeled with 4-sulfophenylisothiocyanate (SPITC) obtained from Sigma-Aldrich (Cat # 85,782-3) and used as supplied. Labeling was accomplished by adding 10 µl of triethylamine, 10 µl of 2 M acetic acid and 20 µl of a 10% by weight solution of SPITC in water to 100 µl of each denatured protein sample. The reaction mixture was heated at 50° C. for 24 h.

Figure 7:
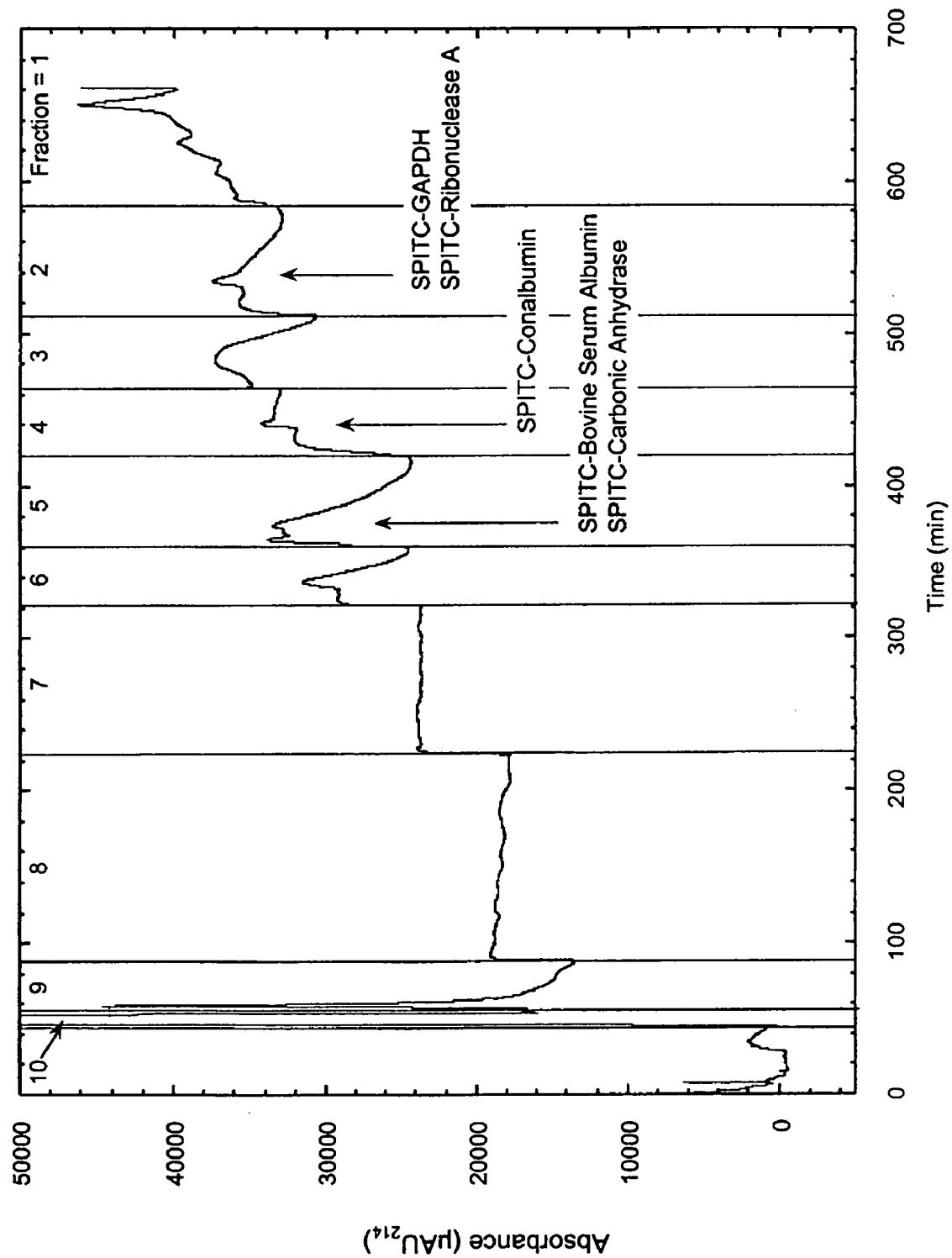
FIG. 7 is an electropherogram obtained during separation of a sample containing five sulfophenylisothiocyanate-labeled proteins (hen white conalbumin, bovine serum albumin, bovine carbonic anhydrase II, carbonic anhydrase II, rabbit muscle GAPDH, and bovine ribonuclease A) as obtained following electrophoresis by capillary zone electrophoresis. Absorbance was monitored at 214 nm. Under the conditions of this particular experiment (see Example 2) in which the proteins were labeled, the labeled proteins were partially resolved.

A quantity of 50 µl of each of the SPITC-labeled protein standards was mixed together and separated by cZE as described in Example 1, with the exception that the pH of the separation buffer was adjusted to 3.0. The individual SPITC-labeled proteins were resolved (FIG. 7). Thus, this example taken in view of the results for Example 1 in which unlabeled proteins were poorly resolved demonstrates the positive effect that labeling can have when done prior to a cZE separation. Fractions were collected by electroelution into separate vials containing the separation buffer at the times indicated. The identies of the SPITC-labeled proteins were determined by subsequent cGE analysis of the fractions.

Example 3

CIEF First Dimension Separation with Fraction Collection

Bovine Serum Albumin, Carbonic Anhydrase, and Conalbumin were used as supplied from Sigma-Aldrich (Table 2). Each protein was denatured as described in Example 1. A 10 µl aliquot of each denatured protein sample was added to 200 µl of the cIEF focusing buffer. The cIEF focusing buffer consisted of 0.4% by weight hydroxymethyl cellulose solution (Beckman-Coulter eCAP cIEF Gel Buffer, Cat # 477497) containing 1% by volume pH 3–10 Ampholytes (Fluka, Cat # 10043) and 1% by weight 3-[(3-cholamidopropyl) dimethlammonio]-1-propane sulfonate.

A poly(ethylene glycol)-coated 60 cm long 100 µm internal diameter fused silica capillary (Supelcowax 10, Supelco, Cat # 25025-U) was filled with the protein sample in the focusing buffer. The capillary contents were focused between 10 mM phosphoric acid and 20 mM NaOH reservoirs for 7.5 min at 500 V/cm and 25° C. A 0.5 psi pressure gradient was then applied between the anolyte and catholyte reservoirs to facilitate the elution of the focused proteins in the direction of the electroosmotic flow.

Figure 8:
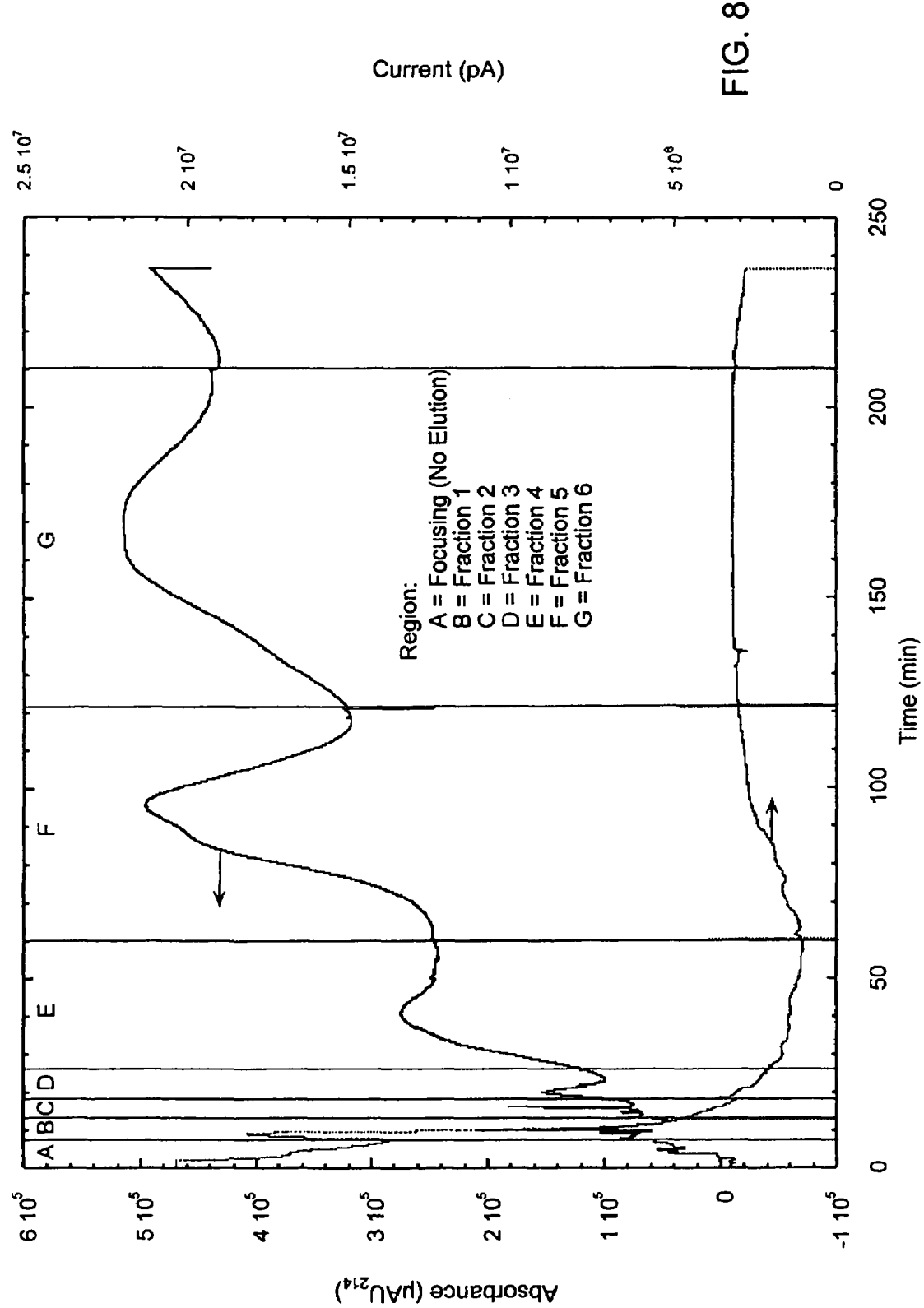
FIG. 8 is an electropherogram obtained during separation of a sample containing the proteins hen white conalbumin, bovine serum albumin, and bovine carbonic anhydrase II, by CIEF.

The protein peaks were detected by monitoring the ultraviolet absorption at 214 nm through an optical window in the capillary positioned 50 cm from the low pH end. The current through the capillary was also monitored (FIG. 8). Fractions (B–G) were collected into 50 µl of 20 mM NaOH contained in separate reservoir vials for the times depicted (FIG. 8). Only fractions F and G were found to contain protein (see Example 4). Fraction G was found to contain carbonic anhydrase and no conalbumin or bovine serum albumin. Conalbumin and bovine serum albumin were found to coelute in the peak observed in fraction F. This experiment illustrates the partial separation of a mixture of proteins in a single dimension. Further resolution was achieved in the second dimension (see Example 4).

Example 4

CGE Second Dimension Separation of CIEF Fractions

Each of the CIEF fractions (B–G) collected during the CIEF separation described in Example 3 were evaporated in a Savant Model SC210A Spin-Vap to a final volume of 5 µl to concentrate any protein present in the fraction. A quantity of 10 µl of SDS sample buffer was added to each protein concentrate. The SDS sample buffer consisted of 100 µl of eCAP SDS sample buffer (Beckman Coulter, Cat # 241525), 10 µl of eCAP Orange G Reference Marker (Beckman Coulter, Cat # 241524), and 90 µl of anhydrous glycerol.

Each sample was then run in cGE mode using a linear poly(acrylamide)-coated fused silica capillary 60 cm long with a 100 µm internal diameter. The eCAP SDS 14-200 Gel buffer (Beckman-Coulter Cat # 477416) was used for the separation and in both reservoirs. The separation was conducted at 20° C. and 500 V/cm for 50 min. Ultraviolet detection of the proteins was accomplished at 214 nm through an optical window positioned 50 cm from the sample injection end of the capillary. Molecular weight calibration was conducted in a separate run using eCAP MW Standards (Beckman-Coulter Cat # 477418) as described by the manufacturer. A 100 sec sample injection at 0.5 psi was used to load each sample into the capillary.

Figure 9:
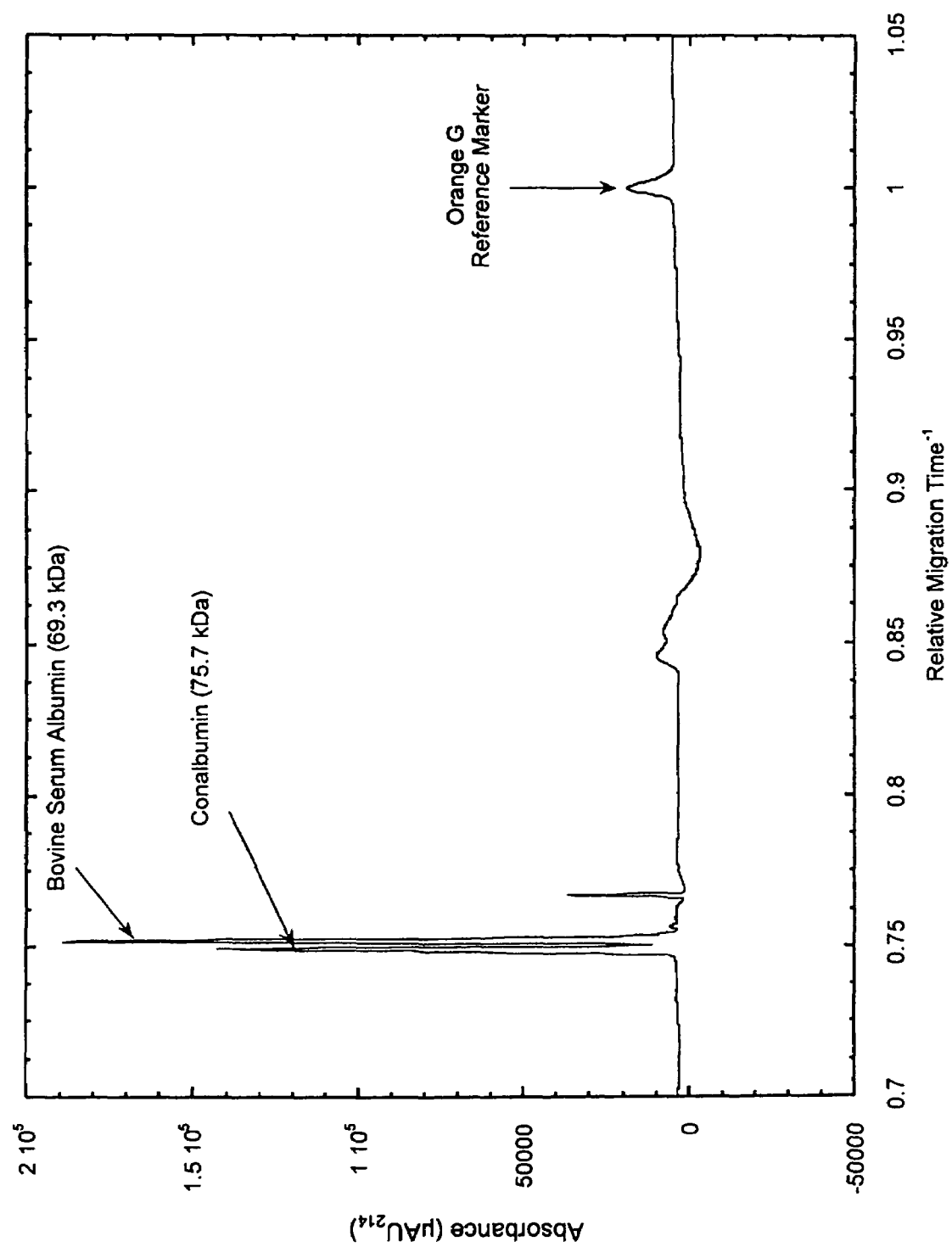
FIG. 9 is an electropherogram of a fraction (fraction F) obtained from the separation by CIEF shown in FIG. 7.
Figure 10:
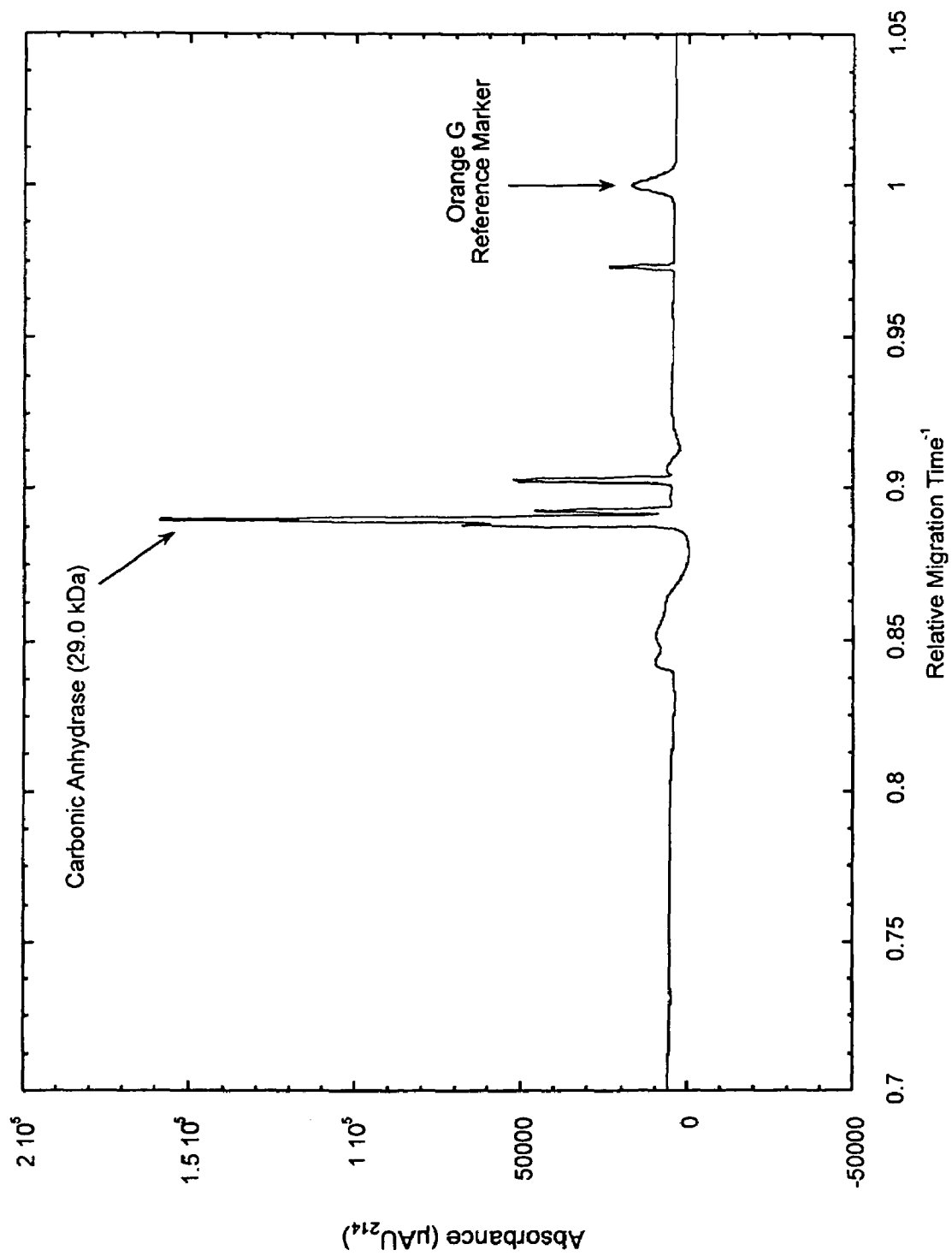
FIG. 10 is an electropherogram of a fraction (fraction G) obtained from the separation by CIEF shown in FIG. 7.
Figure 11:
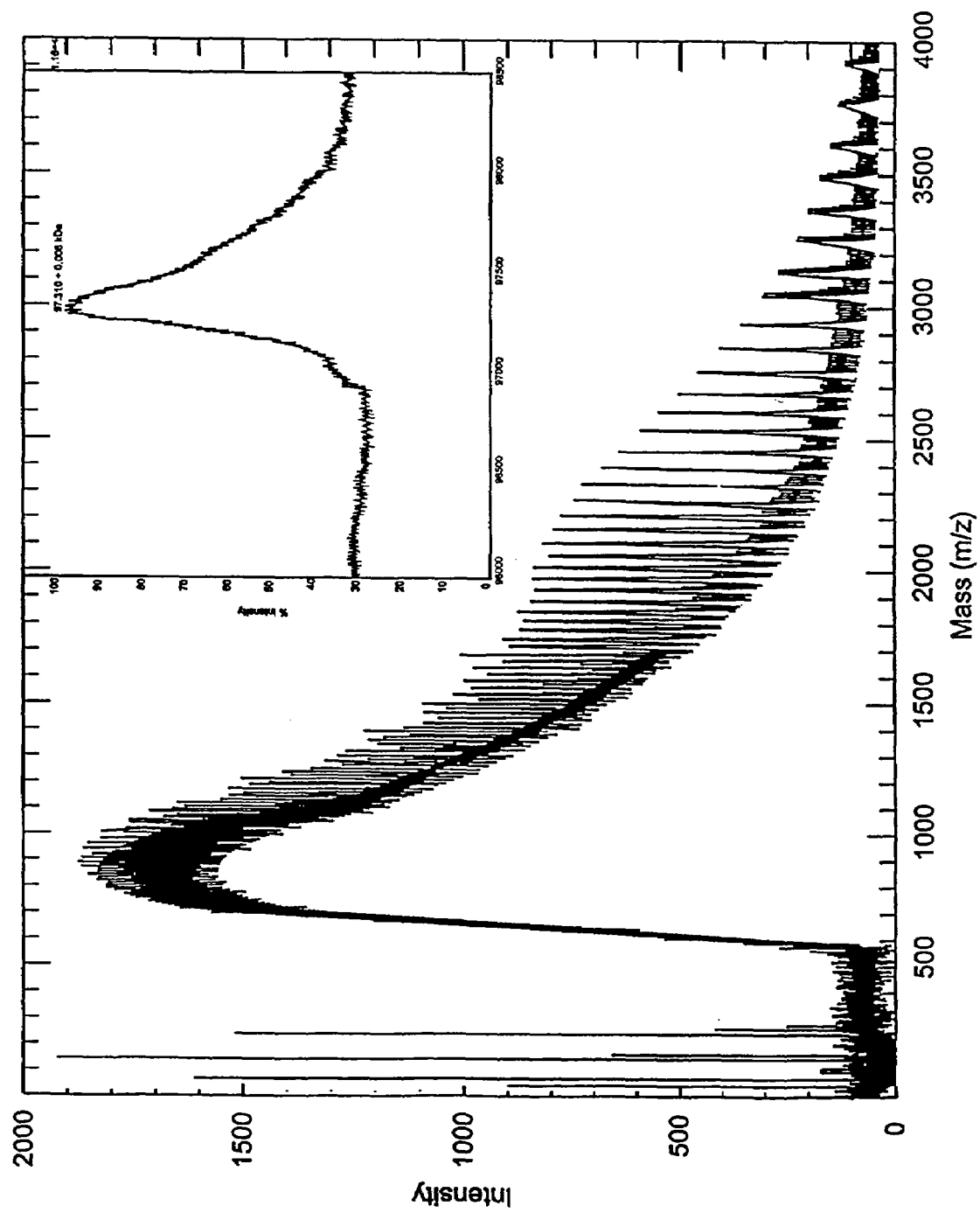
FIG. 11 provides the minimally fragmenting 12 V spectrum of glycogen phosphorylase A protein. A zero charge mass deconvolution of the multiply charged mass peaks observed between 700 and 4000 amu was prepared using the BioSpec Data Explorer™ software.

The resulting electropherograms showed no detectable protein in any cIEF fraction except fractions F (FIG. 9) and G (FIG. 10). The molecular weight of the two proteins seen in fraction F (FIG. 9) correspond to that of bovine serum albumin and conalbumin (Table 2). The molecular weight of the protein seen in fraction G (FIG. 10) corresponded to that of carbonic anhydrase (Table 1). It is observed that the second cGE dimension was necessary to fully resolve bovine serum albumin from conalbumin, which were not resolved by a single cIEF mode (Example 3).

Example 5

Use of Methods in Proteomics Analysis for Distinguishing Between Healthy and Cancerous Tissue This example illustrates the use of the present invention for distinguishing between healthy and cancerous tissue. The present invention can be used to directly analyze the protein expression pattern of healthy and cancerous and metastasized tissues to elucidate patterns of gene expression and translate such relations to the various aspects of onset, staging and metastases in cancers, such as prostrate, breast, colon and skin.

The methods of the invention can significantly decrease the time necessary to conduct functional genomics analysis of the mechanism of disease and can lead to the identification of new therapeutic targets, diagnostic markers, and drug products (i.e., where a specific cellular protein may itself act as a therapeutic agent). By using proteomic analysis the number of genes that must be investigated is reduced 10-fold (from the 50,000 to 150,000 human genes to the 2,000–10,000 genes actually being expressed to form proteins in the target tissue). Through quantitative comparison of the protein expression pattern of healthy and diseased tissue, the number of candidate genes that may play roles in the progression of the disease is farther reduced about 100-fold. Finally, through the subsequent generation of protein sequence tags (PTSs; i.e., a partial amino acid sequence) each of the proteins that show differential expression can be uniquely identified in a manner that allows them to be tracked back to the genome for complete sequencing (e.g., mutation detection).

Initially, tissue samples are obtained from diseased subjects and control subjects (e.g., individuals not known to have the particular cancer being studied). The tissue samples from each individual are homogenized according to known methods. Depending upon the sample, the resulting homogenate is filtered or centrifuged to remove cellular debris. Samples are taken from the homogenate and the proteins therein denatured by adjusting the samples to contain urea (6–8 M), detergent (e.g., 1% by weight sodium dodecyl sulfate) and 1% by weight dithiothreitol. Samples are heated at 95° C. for 15 minutes to speed denaturation.

Samples (5 µl) are then electrophoresed by CIEF on a column (75 micron inside diameter by 60 cm long). Anolyte is initially 10 mM phosphoric acid and the catholyte is initially 20 mM sodium hydroxide. Separations are conducted at 500 V/cm. Fractions of resolved proteins are eluted by increasing the sodium chloride concentration of the catholyte solution from 10 mM to 100 mM in 96 incremental units. Fractions are collected by sequentially inserting the high pH end of the capillary into 200 µl of each salt concentration in catholyte solution contained in the wells of a 96 well plate. The separation current is allowed to reequilibrate before the capillary end is moved to the next fraction.

Prior to labeling, fractions are concentrated using a rotary evaporator. Protein in the collected fractions is labeled by reacting the proteins with fluorescein isothiocyanate as described in Example 2 for sulfophenylisothiocyanate.

Fractions containing the labeled proteins are separately electrophoresed by CZE. The labeled proteins are diluted into a CZE sample buffer to form a final solution consisting of 25 mM tris(hydroxymethyl)aminomethane phosphate buffer (pH 4.0), 8 M urea, and a final concentration of about 1 mg/ml of protein. The mixed protein sample and each of the control samples are run in CZE mode in a 60 cm×75 µm fused silica capillary (Becklman Coulter). An 800 µm window is located 50 cm from the cathodic end of the capillary. A 160 nl sample volume is pressure injected at the cathodic end and the separations conducted at 500 V/cm in a 25 mM TRIS-phosphate and 8 M urea running buffer at pH 4.0. Proteins are eluted by the residual EOF in the capillary. Fractions are again collected on the basis of elution time in the wells of a 96 well microtiter plate as the capillary is progressively advanced from one well to the next. Each well contains 200 µl of the cZE separation buffer. This process is repeated with samples from the other fractions collected during CIEF.

Samples from CZE fractions are further resolved by CGE. Fractions from CZE are separately concentrated by rotary evaporation to a final liquid volume of about 5 µl. The protein sample is isolated from crystalized urea by refrigerated (4° C.) centrifugation. Ten microliters of SDS sample buffer is added to each vial of protein concentrate. The SDS sample buffer consists of 100 µl of eCAP SDS sample buffer (Beckman Coulter, Cat # 241525), 10 µl of eCAP Orange G Reference Marker (Beckman Coulter, Cat # 241524), and 90 µl of anhydrous glycerol.

Each sample is run in cGE mode using a linear poly(acrylamide)-coated fused silica capillary 60 cm long with a 100 µm internal diameter. Commercially available eCAP SDS 14-200 Gel buffer (Beckman-Coulter Cat # 477416) is used for the separation and included in both reservoirs. The separation is conducted at 20° C. and 500 V/cm for 50 min.

Molecular weight calibration is conducted in a separate run using eCAP MW Standards (Beckman-Coulter Cat # 477418) as described by the manufacturer. A 100 sec sample injection at 0.5 psi is used to load each sample into the capillary. Resolved proteins are detected by fluoroscein fluorescence with a 466 nm laser induced fluorescence detector.

Example 6

This example illustrates the use of inverted mass ladder sequencing to determine the sequence of glycogen phosphorylase.

Glycogen phosphorylase A (EC 2.4.1.1) is a member of a group of proteins that are acetylated at the amino-terminus (see, Persson, et al., *Eur. J. Biochem.* 152:523–527 (1985). This acetyl group can be attached to the N-terminus via natural biochemical means, as is the case in glycogen phosphorylase. N-terminal acetylation can also be accomplished through published protocols (see, Lomant, et al., J. Mol. Biol., 104:243–261 (1976)) using N-hydroxysuccimidyl- or sulfo-N-hydroxysuccimidyl-acetate, which are commercially available from Pierce Chemical Co., Rockford, Ill. This acetyl group provides a unique mass signature for inverted mass ladder sequence determination.

Acetylated glycogen phosphorylase A was purchased from Sigma-Aldrich Chemical Co. (Catalog # P1261). The protein was dissolved in 4 mM ammonium acetate buffer (pH=5.0) at 0.72 mg/mL. This sample (500 µL) was purified of residual nonvolatile ions and low molecular weight protein and peptide impurities by dialysis using a Microcon (Millipore Corporation) spin dialysis tube with a 50,000 MW cutoff membrane. The sample was dialyzed 10 times against the 4 mM ammonium acetate buffer following Microcon product instructions. The retentate was recovered in 460 µL of the ammonium acetate buffer, yielding a final protein concentration of about 0.8 mg/mL.

The recovered retentate was subjected to in-source fragmentation in an electrospray-time-of-flight mass spectrometer—a Mariner™ (PE Biosystems, Inc.) equipped with the commercial Microspray ion source. The mass spectrometer settings were optimized and the instrument was calibrated immediately prior to injecting the glycogen phosphorylase sample according to the published instrument protocols. The sample was fed continuously into the microspray source at a rate of 0.4 µL/min. The nozzle potential was increased from the minimum setting of 12 V to a maximum of 350 V in 25 V increments with 5 minutes instrument equilibration time alotted before collecting spectra at each nozzle potential. A total of thirty 3-second spectra were accumulated for analysis at each nozzle potential.

Figure 12:
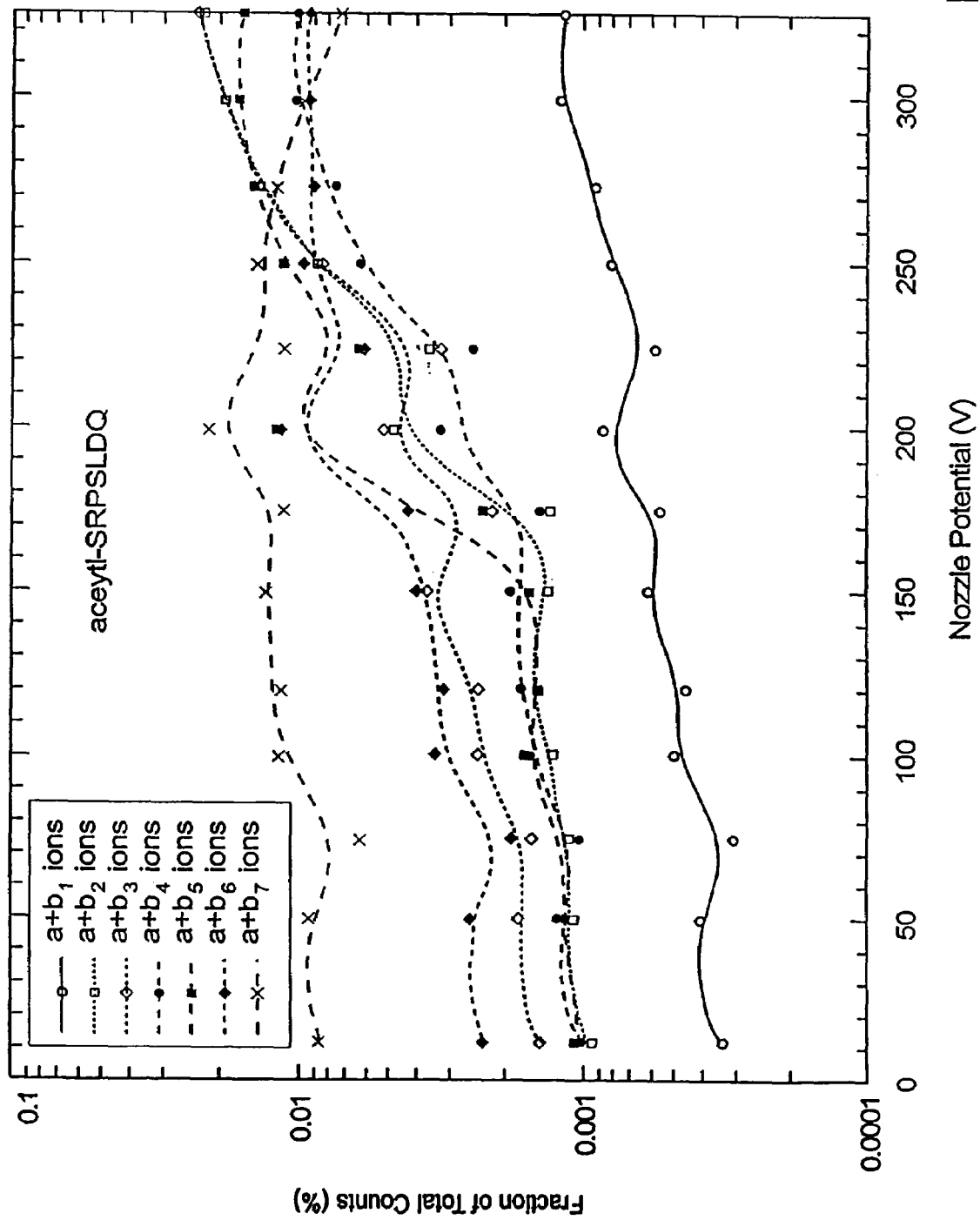
FIG. 12 illustrates the increase in relative abundance for peaks corresponding to the acetylated peptide masses, with increasing nozzle potential. Acetyl-SRPSLDQ=SEQ ID NO:6.
Figure 13:
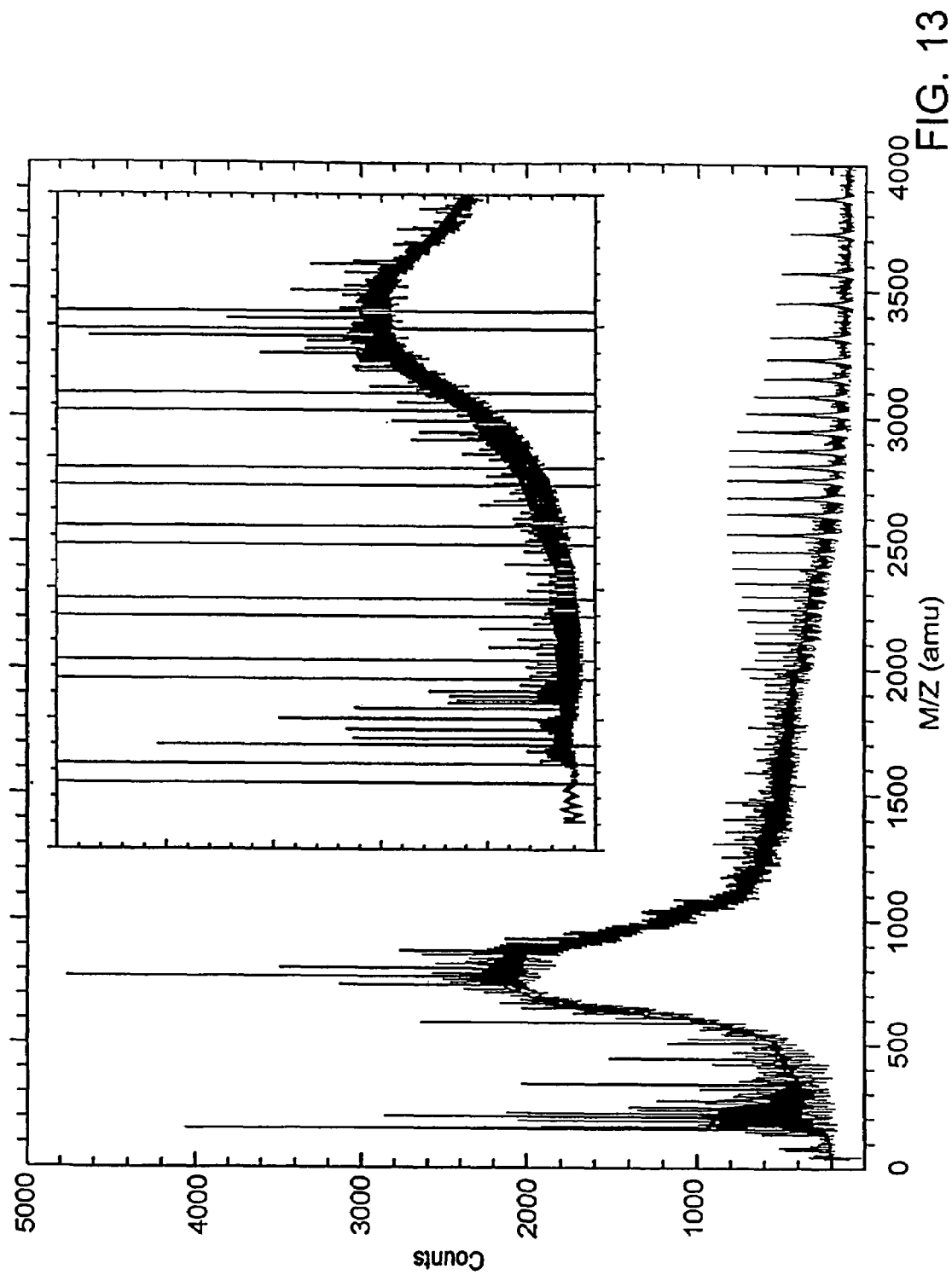
FIG. 13 provides an example of a substantially fragmented mass spectra, corresponding to 250 V nozzle potential for glycogen phosphorylase A.

The identity and purity of the parent glycogen phosphorylase A protein was determined at the minimally fragmenting 12 V spectrum (FIG. 1) by conducting a zero charge mass deconvolution of the multiply charged mass peaks observed between 700 and 4000 amu using the BioSpec Data Explorer™ software (Version 3.0) supplied by the vendor. The N-terminal sequence of glycogen phosphorylase was determined by inspecting the resulting mass spectra to determine the relative abundance of the possible acetylated peptides at each nozzle potential. Peaks corresponding to the acetylated peptide masses were clearly observed to increase in relative abundance with increasing nozzle potential (FIG. 12). FIG. 12 shows the cumulative relative abundance of both the a- and b-ions for each peptide mass in the sequence. An example of a substantially-fragmented mass spectra, corresponding to 250V nozzle potential of 250 V is shown in FIG. 13. Those mass fragments showing increased abundance at nozzle potentials above 200V correspond to the published amino-terminal sequence for glycogen phosphorylase, acetyl-SRPLSD (SEQ ID NO:11) (see Persson, et al., *ibid.*).

The lack of a ionizable residue on either the amino-terminal serine or the acetate label prevented direct detection of the first amino acid in the sequence. However, the identity of this amino acid is readily deduced from the cumulative mass of the second peptide fragment (corresponding to acetyl-SR), which creates the first detectable positively charged ion from the R-residue. The sequence of the peptide mass ladder became ambiguous beyond the sixth amino acid residue at all nozzle potentials tested.

Example 7

This example illustrates the use of inverted mass ladder sequencing to determine the sequence of bradykinin labeled with phenylisothiocyanate.

Bradykinin, a 9 amino acid peptide, was purchased from Sigma-Aldrich (Cat # B3259) and used as supplied. Bradykinin (5 mmoles) was solubilized in 100 µL of coupling buffer consisting of 10 µL of triethylamine (neat), 10 µL of 2 M acetic acid, 5 µL of sequencing grade phenylisothiocyanate (PITC) purchased from Pierce (Cat # 26422), and 2 mL of 50% aqueous methanol. The coupling-mixture was incubated for 10 min at 55° C. The reaction mixture was cooled to room temperature and extracted twice with 150 µL of a 2:1 (v/v) heptane/ethyl acetate solution. The extracted sample was lyophilized and resuspended to 2 µM PITC-bradykinin in a 50% aqueous acetonitrile solution containing 1% by volume acetic acid.

The PITC-labeled Bradykinin was subjected to in-source fragmentation in an electrospray-time-of-flight mass spectrometer—a Mariner™ (PE Biosystems, Inc.) equipped with the standard commercial pneumatic electrospray ion source. The mass spectrometer settings were optimized and the instrument was calibrated immediately prior to injecting the PITC-Bradykinin sample according to the published instrument protocols. The sample was fed continuously into the electrospray source at a rate of 5 µL/min. The nozzle potential was increased from the minimum setting of 12 V to a maximum of 350 V in 25 V increments with 1 minute of instrument equilibration time alotted before collecting spectra at each nozzle potential. A total of thirty 3-second spectra were accumulated for analysis at each nozzle potential.

Figure 14:
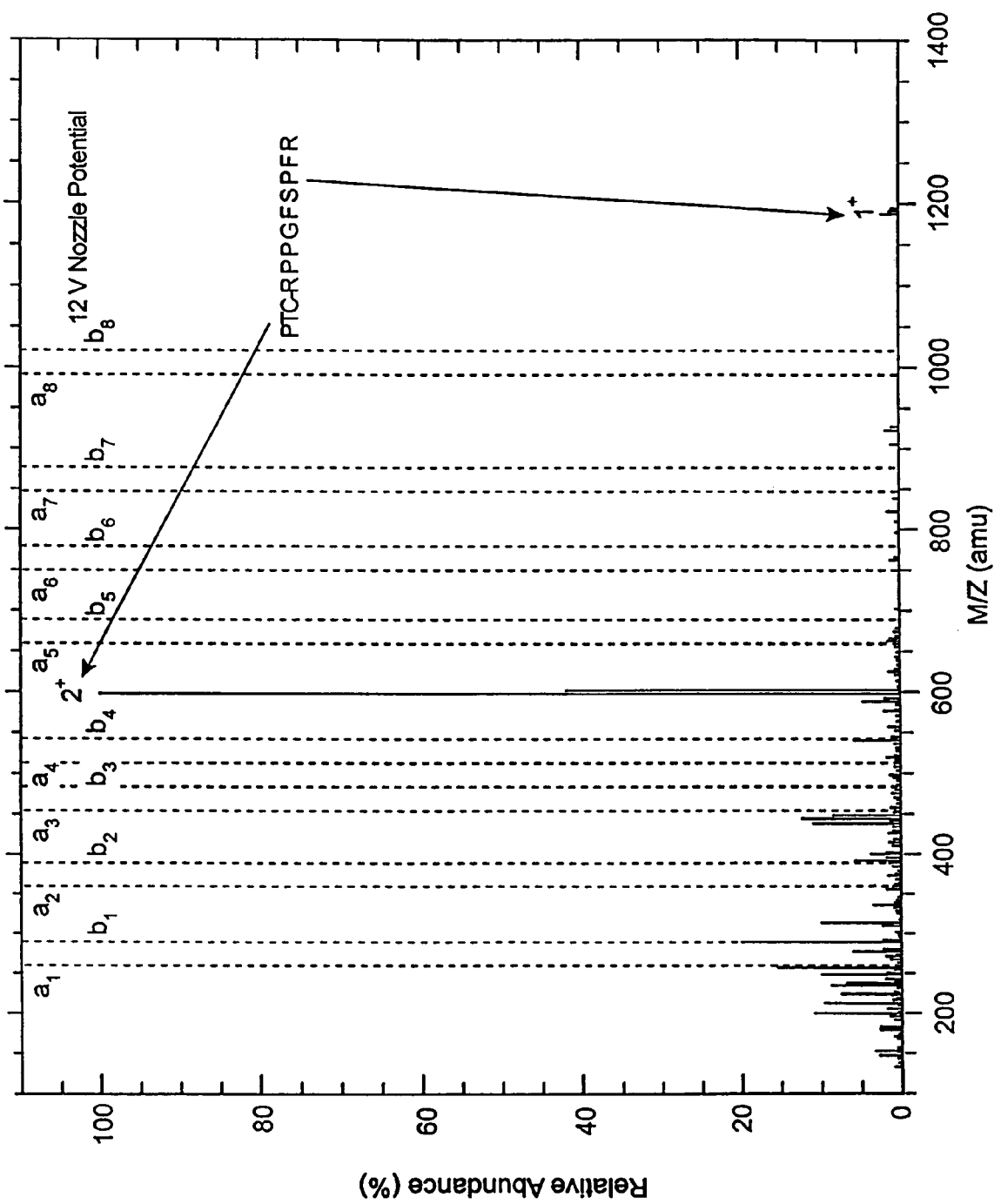
FIG. 14 provides the minimally fragmenting 12 V spectrum of PITC-Bradykinin peptide (SEQ ID NO:7). A zero charge mass deconvolution of the multiply charged mass peaks observed between 700 and 4000 amu was prepared using the BioSpec Data Explorer™ software.
Figure 15:
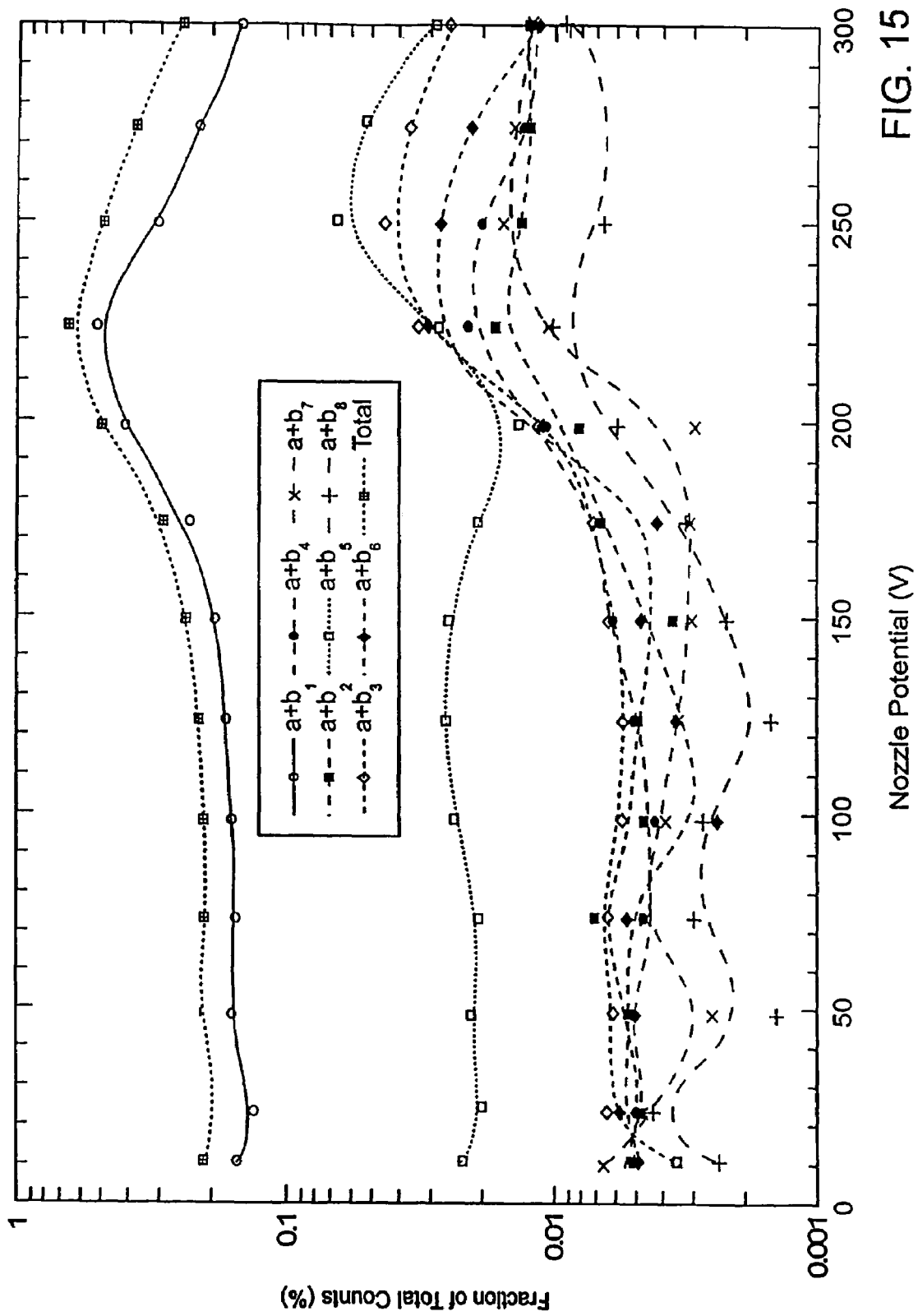
FIG. 15 illustrates the increase in relative abundance for peaks corresponding to the PITC-labeled peptide masses, with increasing nozzle potential.
Figure 16:
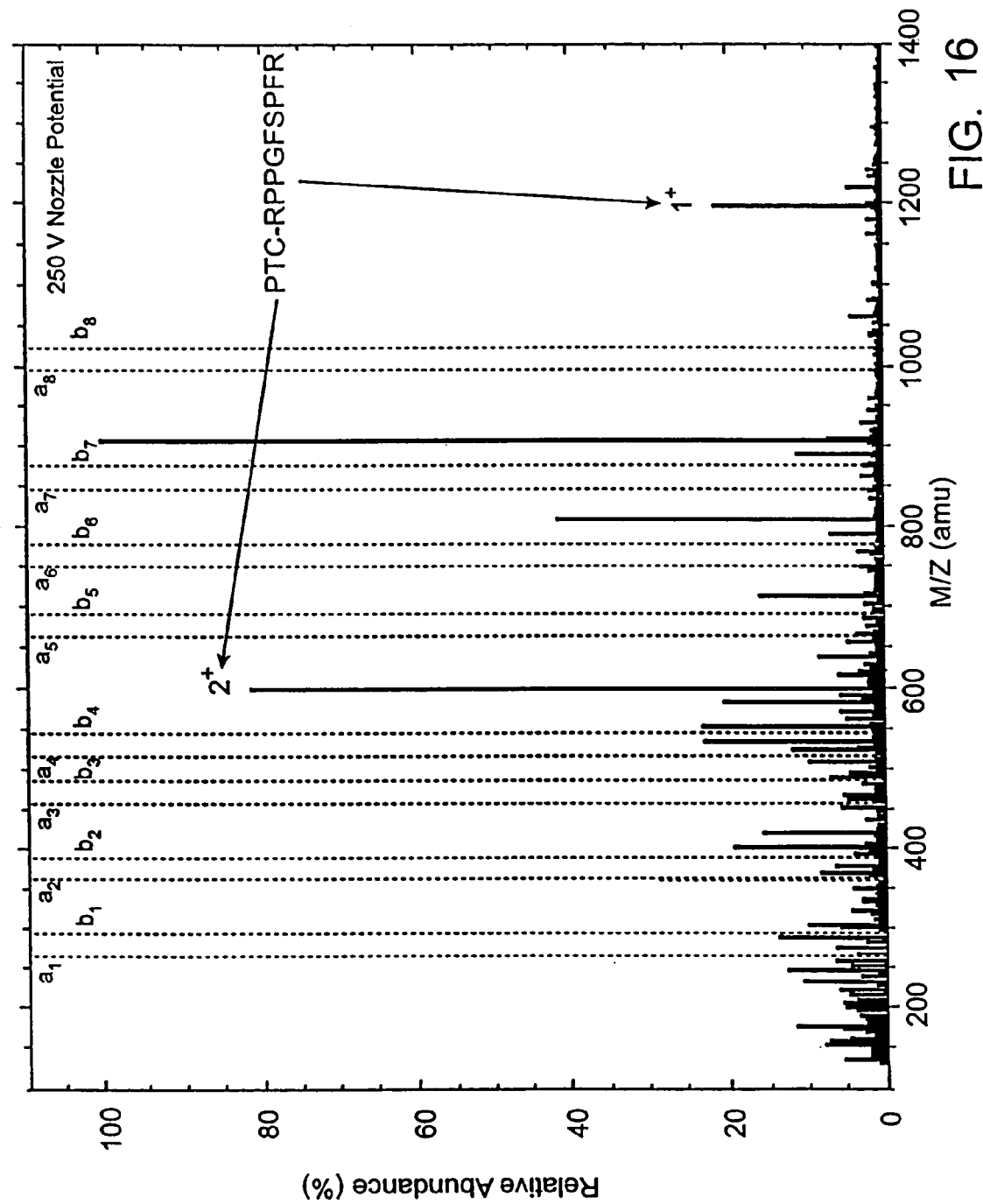
FIG. 16 provides an example of a substantially fragmented mass spectra, corresponding to 250 V nozzle potential for PITC-labeled Bradykinin (SEQ ID NO:7).

The identity and purity of the parent PITC-Bradykinin peptide was determined at the minimally fragmenting 12 V spectrum (FIG. 14) based on the calculated mass for the expected reaction product. The concentration of residual unlabeled Bradykinin was determined by standard addition to be less than 5%. The N-terminal sequence of Bradykinin was determined by inspecting the resulting mass spectra to determine the relative abundance of the possible PITC-labeled peptide fragments at each nozzle potential. Peaks corresponding to the PITC-labeled peptide masses were clearly observed to increase in relative abundance with increasing nozzle potential (FIG. 5). FIG. 5 shows the cumulative relative abundance of the sum of the a- and b-ions for each peptide mass in the sequence. An example of a substantially-fragmented mass spectra, corresponding to a nozzle potential of 250 V is shown in FIG. 16. Those mass fragments showing increased abundance at nozzle potentials above 200V correspond to the published amino-terminal sequence for Bradykinin (see Sigma Product Catalog, Biochemicals and Reagents for Life Science Research, 1999).

Some of the PITC-Bradykinin fragments are seen to overlap the peaks of other ions produced by the sample matrix. The $b_1$-ion (PITC-R) overlapped the first monoisotopic peak of an ion identified as being produced from the sample matrix (in the absence of labeled Bradykinin). The abundance of this matrix ion was found to remain invariant with nozzle potential. Similarly, the $a_2$-ion peak (PITC-RP) was found to overlap the second isotope peak of another ion produced by the matrix. In this case the matrix ion was found to disappear with increasing nozzle potential. The expected relative abundance of the first through third isotope species and inspection of both the a- and b-ion positions were used to determine and deconvolute these overlaps in the mass spectra as previously described (see, Hines, et al., Am. Soc. Mass. Spec. 3:326–336 (1992)).

Example 8

This example illustrates the use of inverted mass ladder sequencing to determine the sequence of bradykinin labeled with iminobiotin.

Bradykinin was purchased from Sigma-Aldrich (Cat # B3259) and used as supplied. The N-hydroxysuccimidyl (NHS) ester of iminobiotin was purchased from Pierce (Cat # 21117ZZ) and used as supplied. Bradykinin (5 nmoles) was dissolved in 100 μL of 1 M pyridinium acetate buffer (pH 8.0). The NHS-iminobiotin was dissolved in DMSO to a final concentration of 6.25 mg/mL with 7 μL of this DMSO solution added to the reaction mixture. The reaction mixture was incubated for 2 h at 4° C. The sample was lyophilized and resuspended to final iminobiotin (IMB)-labeled Bradykinin concentration of 2 μM in a 50% aqueous acetonitrile solution containing 10/% by volume acetic acid.

The iminobiotin (IMB)-labeled Bradykinin was subjected to in-source fragmentation in an electrospray-time-of-flight mass spectrometer—a Mariner™ (PE Biosystems, Inc.) equipped with the standard commercial pneumatic electrospray ion source. The mass spectrometer settings were optimized and the instrument was calibrated immediately prior to injecting the PITC-Bradykinin sample according to the published instrument protocols. The sample was fed continuously into the electrospray source at a rate of 5 μl/min. The nozzle potential was increased from a minimum setting of 75 V to a maximum of 400 V in 25 V increments with 1 minute of instrument equilibration time alotted before collecting spectra at each nozzle potential. A total of thirty 3-second spectra were accumulated for analysis at each nozzle potential.

Figure 17:
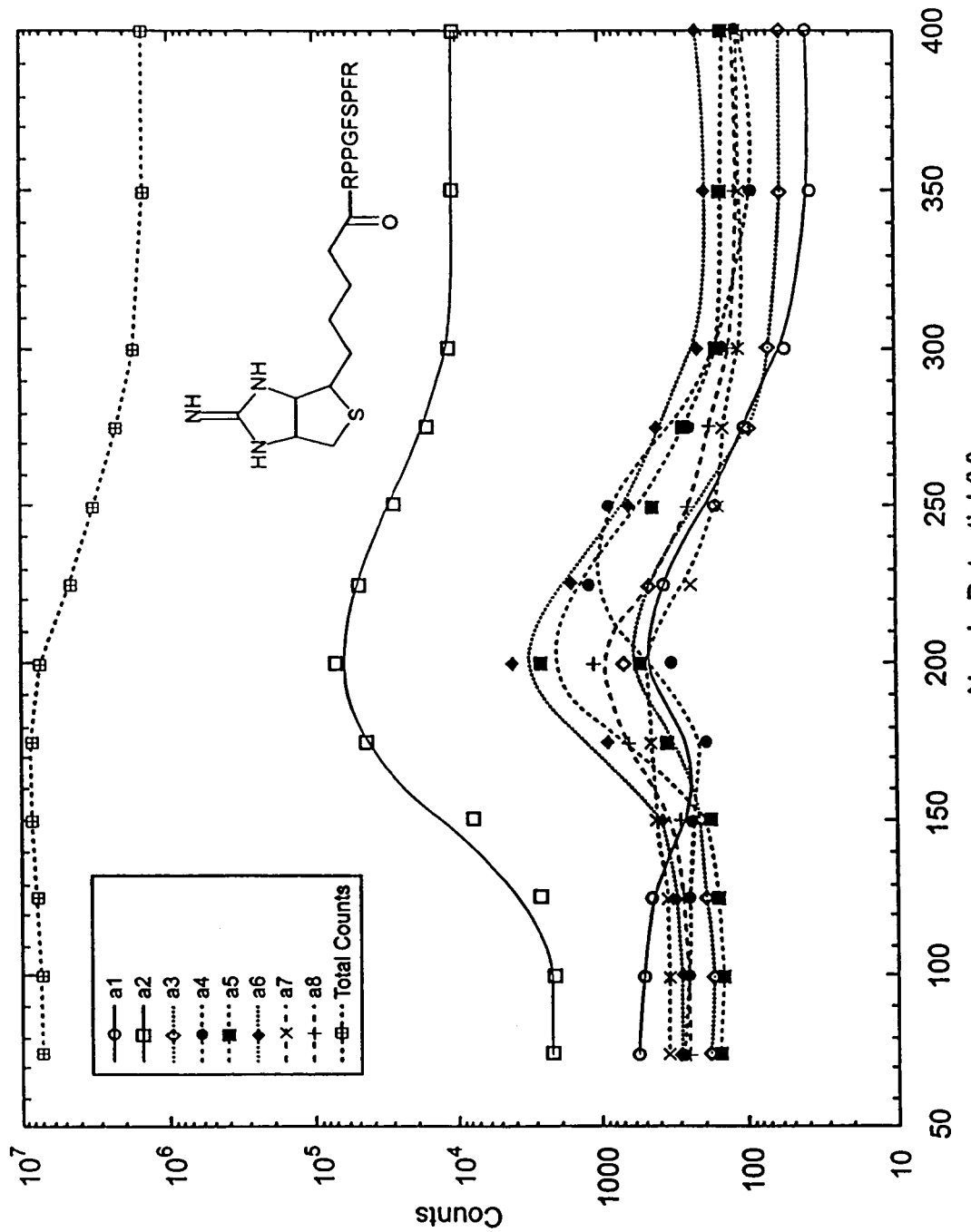
FIGS. 17 and 18 illustrate the peak counts corresponding to the a-ions (FIG. 17) and b-ions (FIG. 18) generated from the 1MB-labeled peptide fragment (SEQ ID NO:8). masses were clearly observed to increase in relative abundance with increasing nozzle potential with a maximum fragmentation abundance noted at about 200V.
Figure 18:
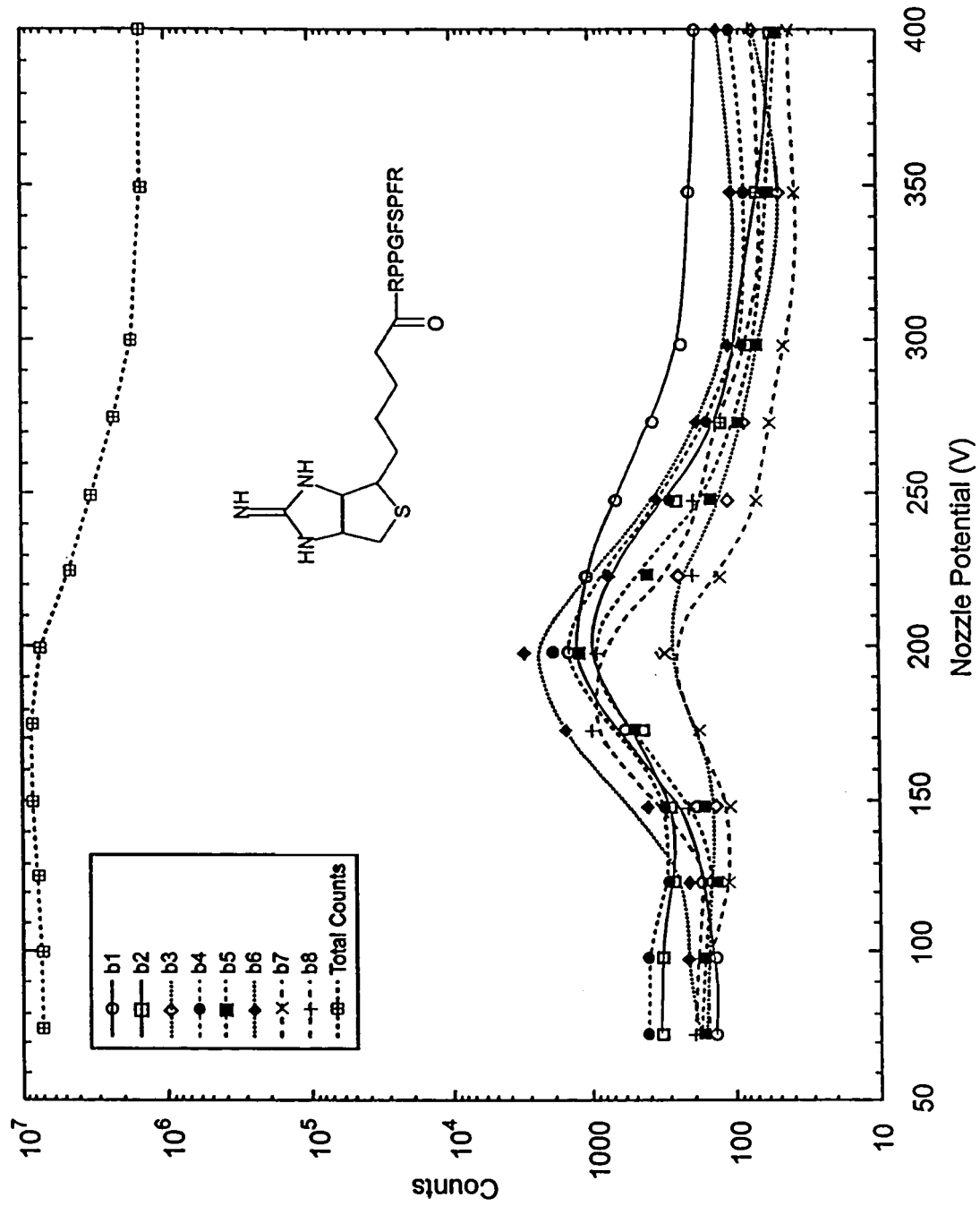

The identity and purity of the parent IMB-Bradykinin peptide was determined at the minimally fragmenting 75 V spectrum based on the calculated mass for the expected reaction product. The concentration of residual unlabeled Bradykinin was determined by standard addition to be less than 5%. The N-terminal sequence of Bradykinin was determined by inspecting the resulting mass spectra to determine the relative abundance of the possible IU-labeled peptide fragments at each nozzle potential. Peak counts corresponding to the a-ions (FIG. 17) and b-ions (FIG. 18) generated from the IMB-labeled peptide fragment masses were clearly observed to increase in relative abundance with increasing nozzle potential with a maximum fragmentation abundance noted at about 200V. The decrease in fragment ion abundance above 200V is attributed to an overall decline in detection or ionization efficiency of all iminobiotin species and parallels the observed decline in total counts (FIGS. 17 and 18). Those mass fragments showing an increased abundance at the 200V nozzle potential correspond to the published amino-terminal sequence for Bradykinin.

Example 9

This example illustrates the application of inverted mass ladder sequencing using a 4-sulfophenylisothiocyanate-labeled apomyoglobin.

Sequencing grade apomyoglobin was purchased from Sigma-Aldrich (Cat #A8673) and used as supplied. Apomyoglobin (10 nmoles) was dissolved in 100 μL of reaction buffer consisting of: 10 μL of triethylamine, 10 mL of 2 M acetic acid, 2 mL of 8 M urea, and 10 μL of a 10 mg/mL aqueous 4-sulfophenylisothiocyanate (SPITC) solution. SPITC was purchased from Fluka (Cat # 86180) and used as supplied. The reaction mixture was incubated for 1 h at 55° C. Urea and excess reagents were removed from the reaction mixture by spin dialysis against 6 washes with deionized water. Spin dialysis was conducted in a model YM10 Microcon (Millipore Cat# 42407) tube following package directions. The dialyzed sample was lyophilized and resuspended in 500 μL of 50% aqueous acetonitrile containing 0.1% by volume triethylamine.

Figure 19:
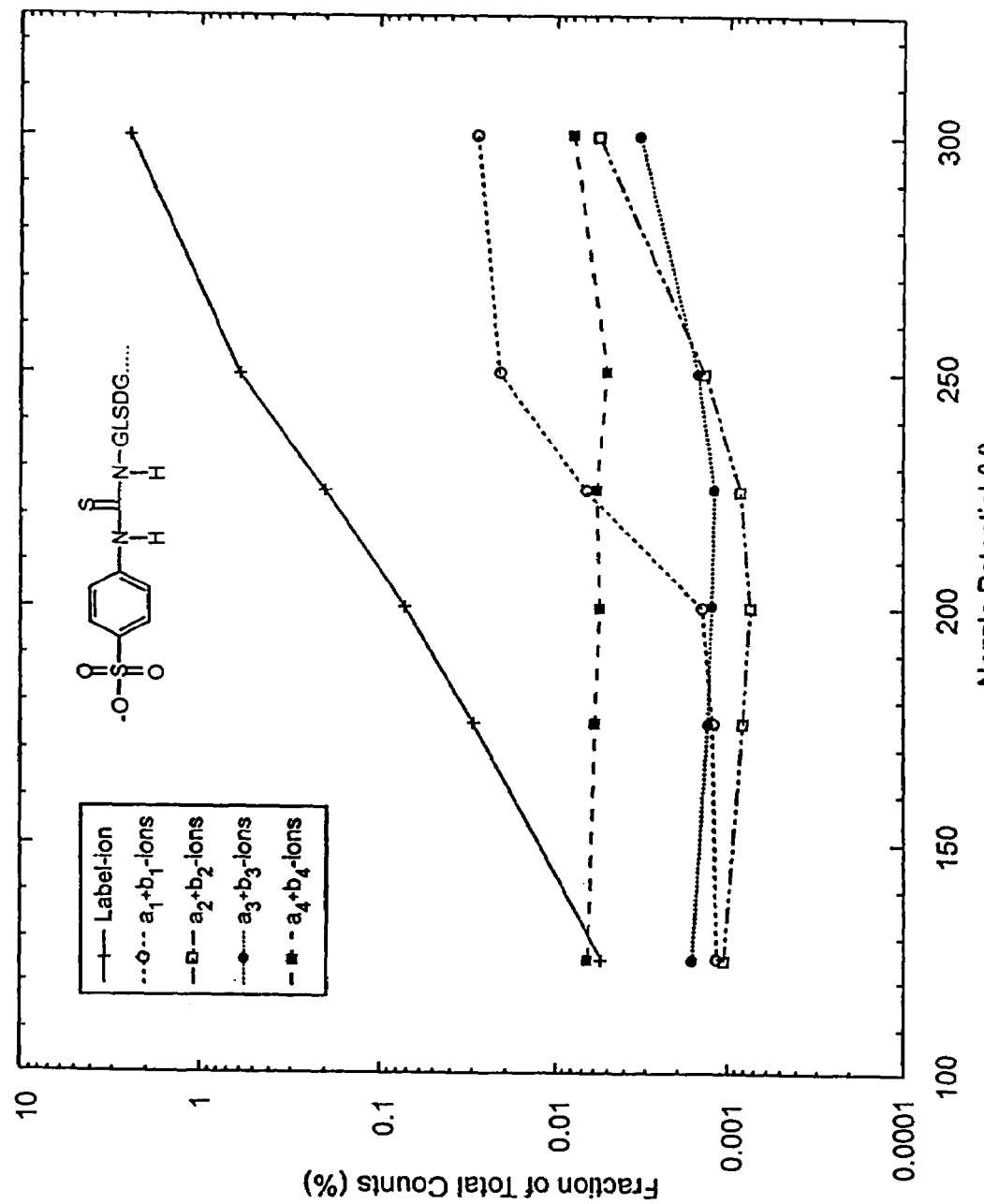
FIG. 19 shows the mass spectrum from SPITC-labeled apomyoglobin (SEQ ID NO:9) obtained in the negative ion mode. The nozzle potential was increased from a minimum setting of 125 V to a maximum of 300V in 25–50 V increments with 1 minute of instrument equilibration time allotted before collecting spectra at each nozzle potential. A total of thirty 3-second spectra were accumulated for analysis at each nozzle potential.

The SPITC-labeled apomyoglobin sample was subjected to in-source fragmentation in an electrospray-time-of-flight mass spectrometer—a Mariner™ (PE Biosystems, Inc.) equipped with the standard commercial pneumatic electrospray ion source. The mass spectrometer was operated in negative ion mode. The mass spectrometer settings were optimized and the instrument was calibrated immediately prior to injecting the sample according to the published instrument protocols. The sample was fed continuously into the electrospray source at a rate of 3 μl/min. The nozzle potential was increased from a minimum setting of 125 V to a maximum of 300V in 25–50 V increments (as shown in FIG. 19) with 1 minute of instrument equilibration time alotted before collecting spectra at each nozzle potential. A total of thirty 3-second spectra were accumulated for analysis at each nozzle potential.

Figure 20:
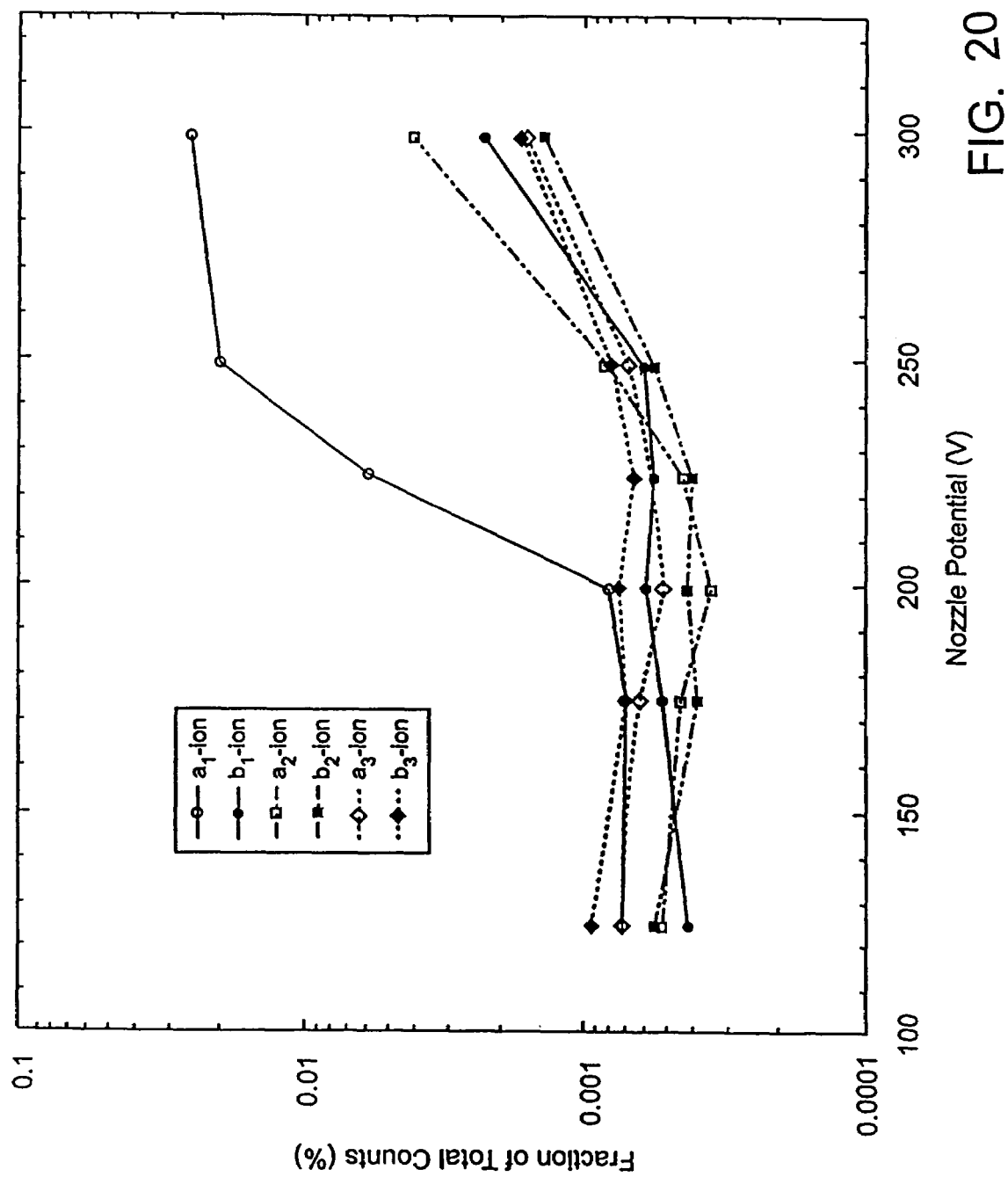
FIG. 20 shows the increase in relative abundance for the $b_1$, $a_2$, $b_2$, $a_3$, and $b_3$ ions which occurs above nozzle potentials of 250V.

Significant amounts of the SPITC label were found to detach from the protein and fragment ions at higher nozzle potentials (FIG. 19), inhibiting the sensitivity of this label for sequence determination. However, peaks corresponding to the fragment masses of the first 3 amino acid residues of the apomyoglobin protein (sequence from Genbank) were found to increase in abundance at higher nozzle potentials. The labeled $a_1$-ion fragment appears at nozzle potentials above 200V. The $b_1$, $a_2$, $b_2$, $a_3$, and $b_3$ ions all appear to increase in relative abundance only above nozzle potentials of 250V (FIG. 20).

Example 10

This example illustrates the use of inverted mass ladder sequencing to determine the sequence of bradykinin labeled at the carboxy-terminus (C-terminus) with (2-aminoethyl) trimethylammonium chloride hydrochloride (2-AETA) via 1-ethyl-3-(3-dimethylaminopropyl)-carbodiimide hydrochloride (EDC).

Bradykinin (Cat # B3259), 2-AETA (Cat # 284556), and 2-[N-Morpholino]ethanesulfonic acid (MES) (Cat # M5287) were purchased from Sigma-Aldrich and used as supplied. EDC was purchased from Pierce (Cat # 22980) and used as supplied. Bradykinin (0.67 μmol) was dissolved in 0.25 mL 0.1 M MES buffer (pH 5.0). This solution was added to 8.0 μmol 2-AETA, and the solution was mixed until the solid was dissolved. This solution was then added to 37.5 μmol EDC and thoroughly mixed until the EDC was dissolved. The sample was incubated at ambient temperature overnight.

A sample was prepared for mass spectrometry by diluting the reaction mixture in a 50% aqueous acetonitrile solution containing 1% by volume acetic acid such that the final concentration of 2-AETA-labeled bradykinin was 10 μM. The 2-AETA-labeled bradykinin was subjected to in-source fragmentation in an electrospray-time-of-flight mass spectrometer—a Mariner™ (PE Biosystems, Inc.) equipped with the standard commercial pneumatic electrospray ion source. The mass spectrometer settings were optimized and the instrument was calibrated immediately prior to injecting the 2-AETA-labeled bradykinin sample according to the manufacturer's instrument protocols. The sample was infused continuously into the electrospray source at a rate of 5 μL/min. The nozzle potential was increased from a minimum setting of 50 V to a maximum of 300 V in 50 V increments with 1 minute of instrument equilibration time alotted before collecting spectra at each nozzle potential. Data in the range of 50–2000 mass-to-charge units were captured in each spectrum, and a total of sixty 3-second spectra were accumulated for analysis at each nozzle potential.

Figure 21:
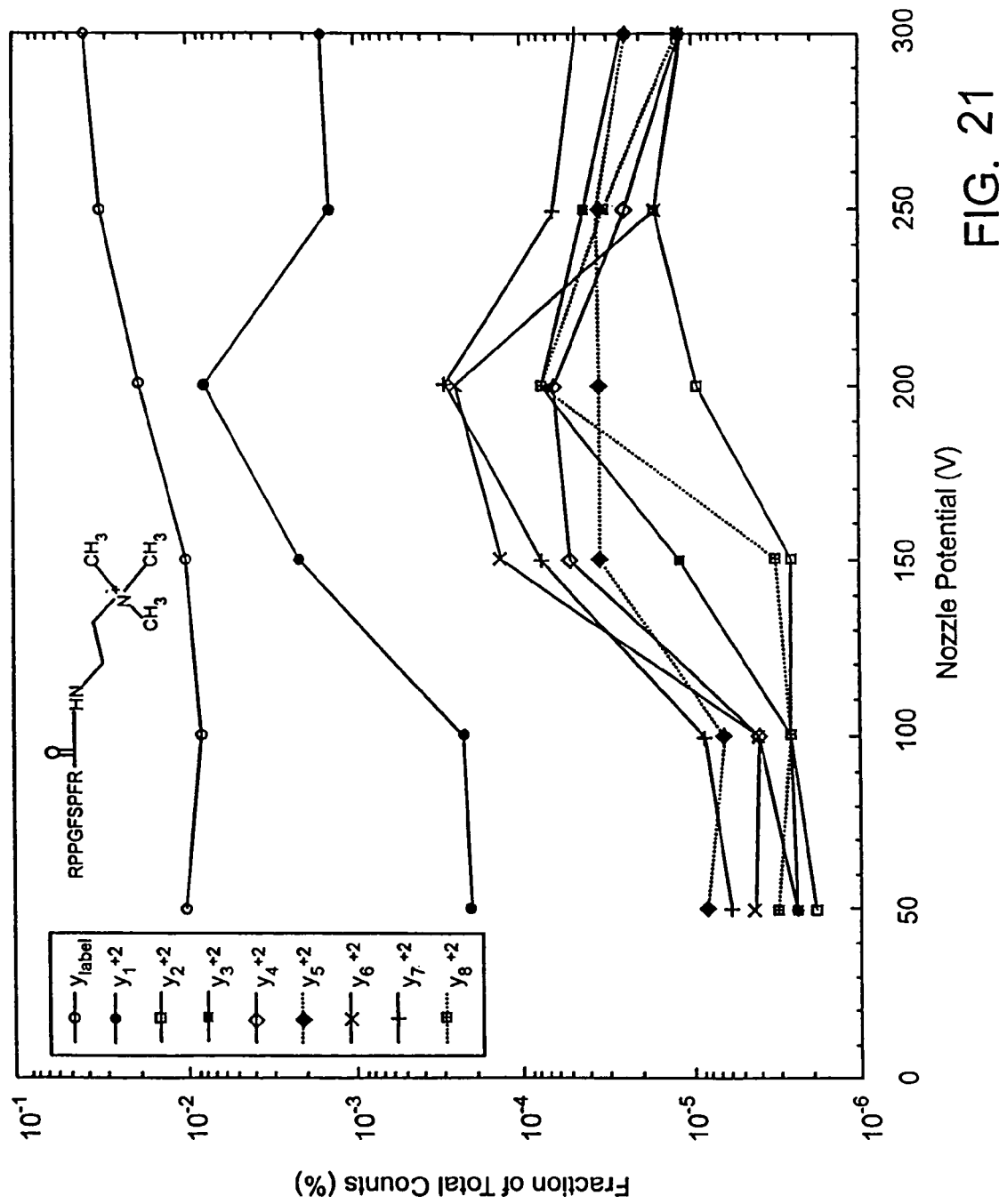
FIG. 21 shows the increase in relative abundance for the doubly charged $y_{1-7}$ ions generated from the C-terminal (2-aminoethyl)trimethylammonium-labeled Bradykinin peptide (SEQ ID NO:10) obtained in positive ion mode. The nozzle potential was increased from a minimum of 50 V to a maximum of 300 V in 50 V increments with 1 minute of instrument equilibration time allotted before collecting spectra at each nozzle potential. A total of sixty 3-second spectra were accumulated for analysis at each nozzle potential.
Figure 22:
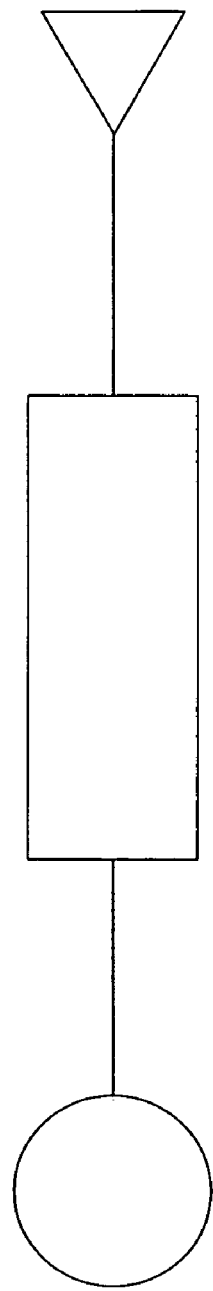
FIG. 22 is a schematic of the covalent chemical label described by the current invention.
Figure 23:
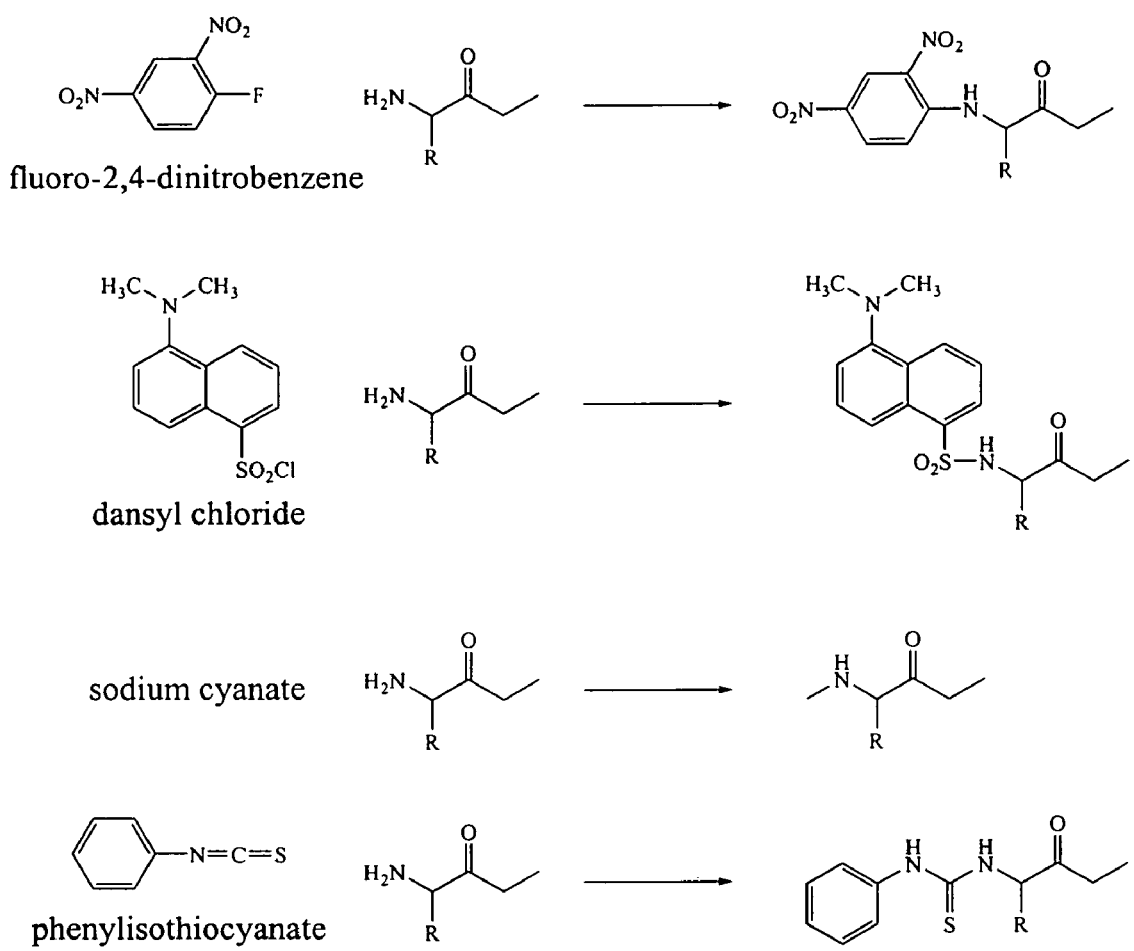
FIG. 23 depicts examples of covalent chemical labels encompassed by the current invention.
Figure 24:
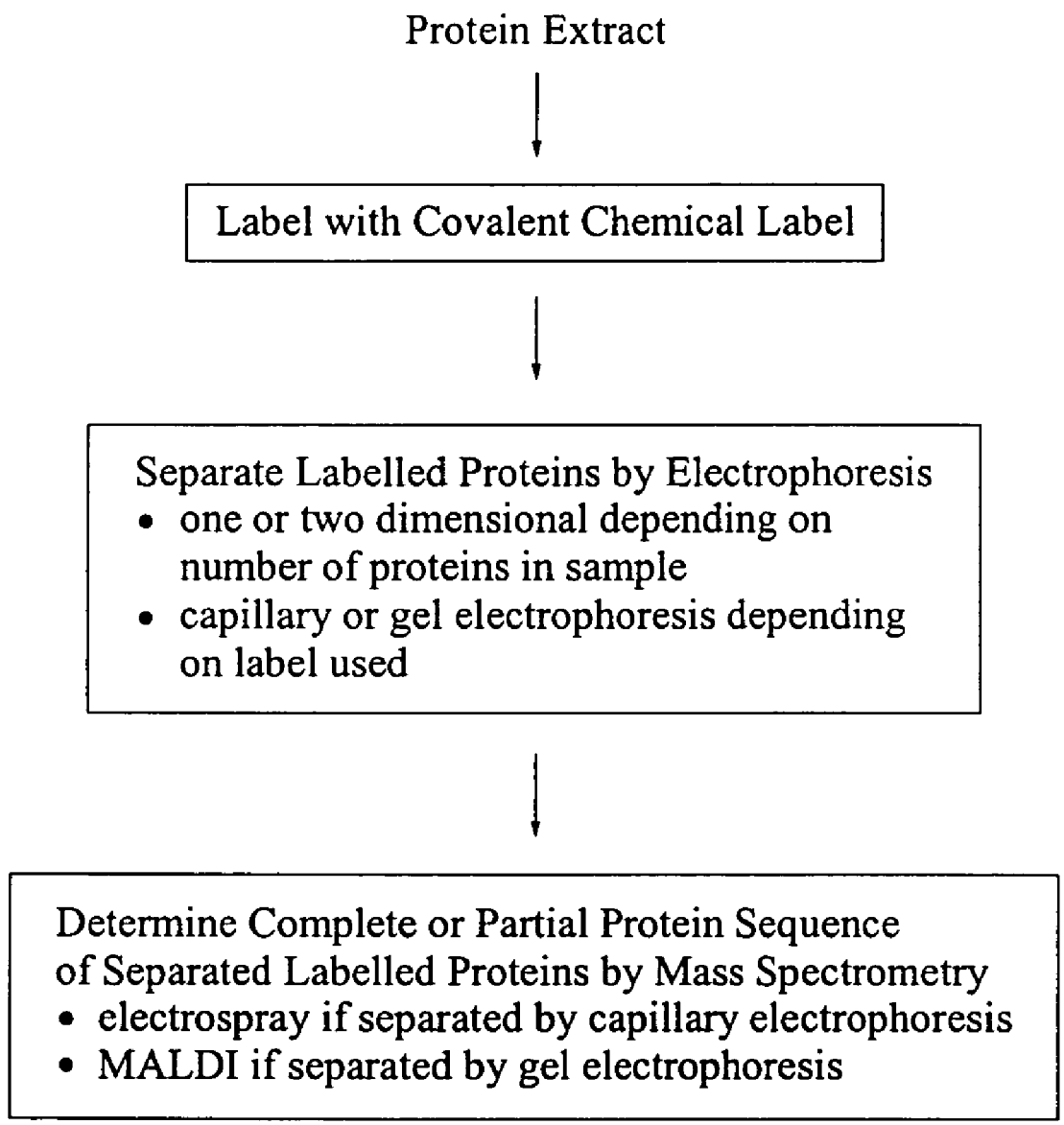
FIG. 24 is a schematic diagram depicting the process steps of an embodiment of the current invention.
Figure 25:
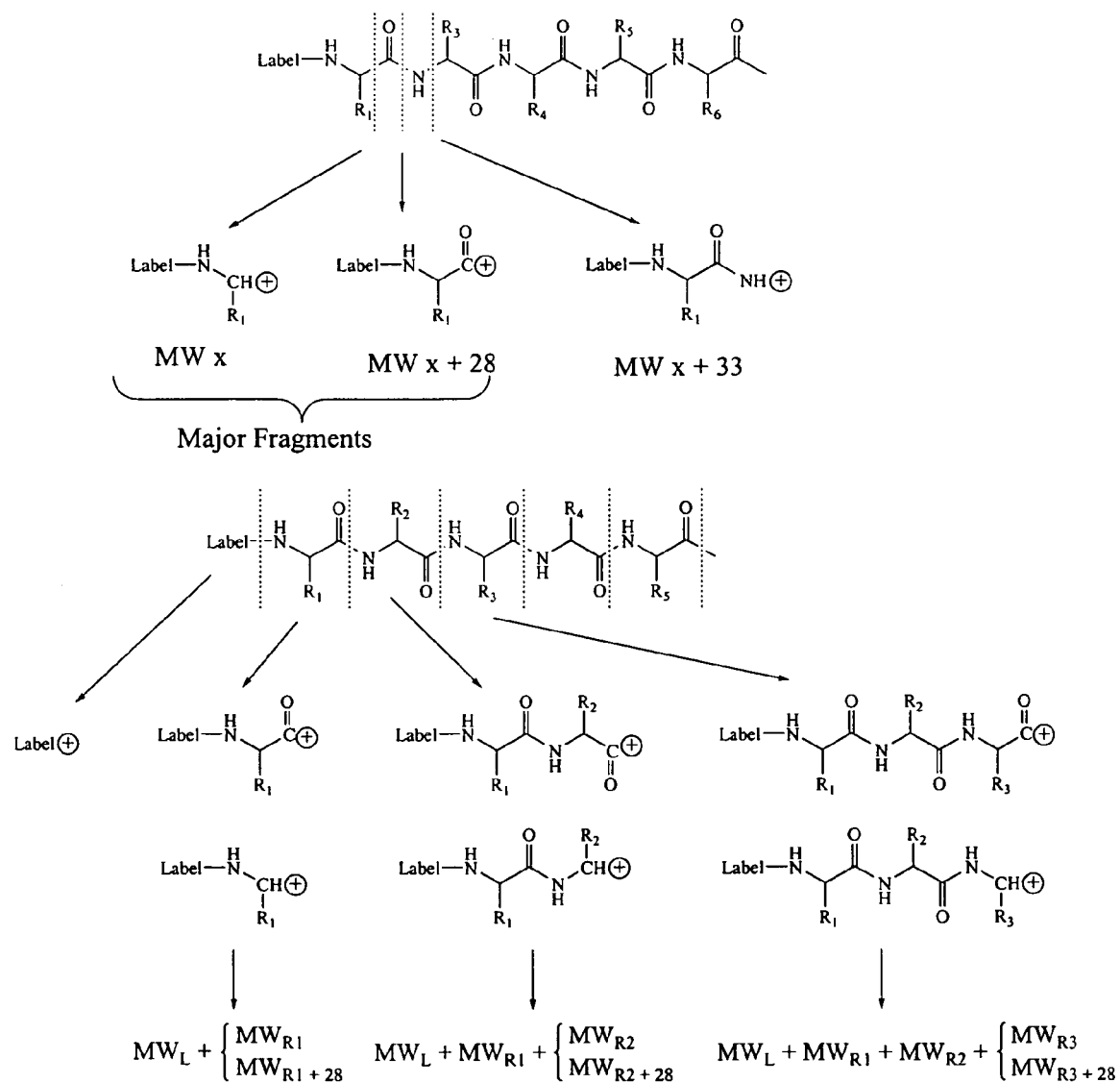
FIG. 25 is a schematic of the protein mass spectrometric fragmentation pattern expected and how to reconstitute the protein sequence from the mass spectrometric fragmentation pattern using the invention.
Figure 26:
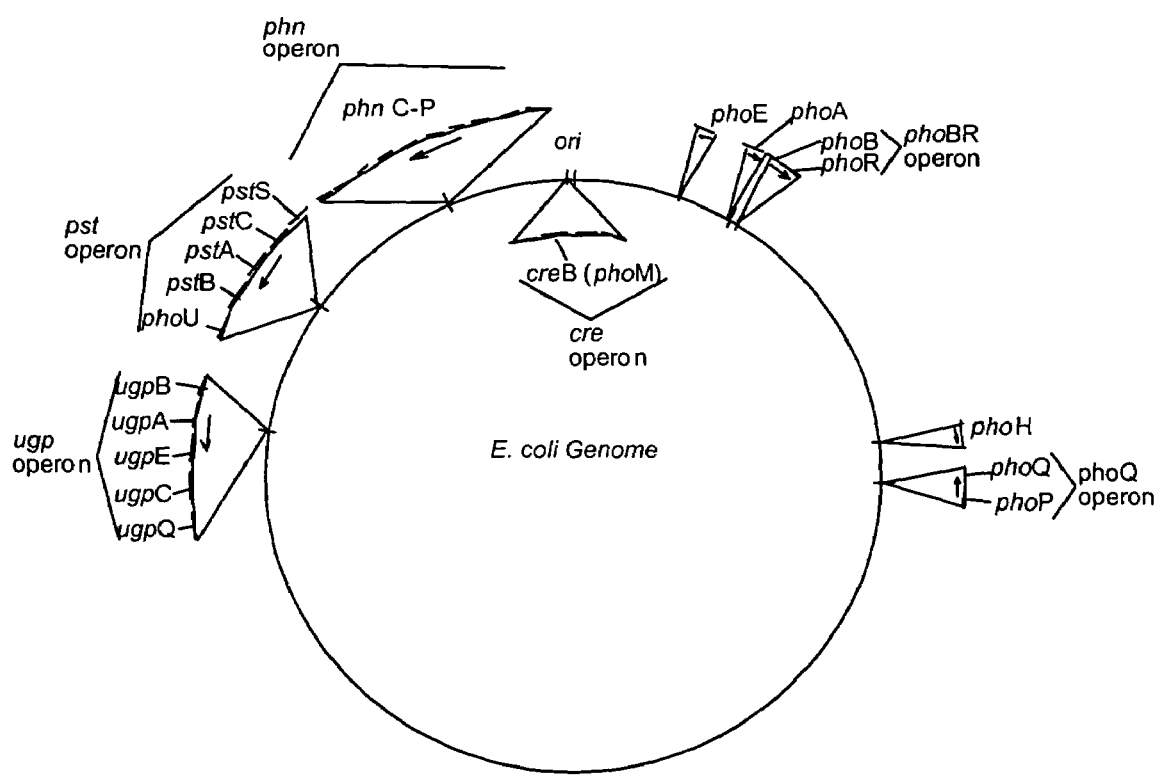
FIG. 26 is a gene loci map of the pho regulon in Escherichia coli. Operons under pho regulatory control are denoted on the outside of the genome. The photo gene (part of the cre operon, which contains four genes) is denoted inside the genome.
Figure 27:
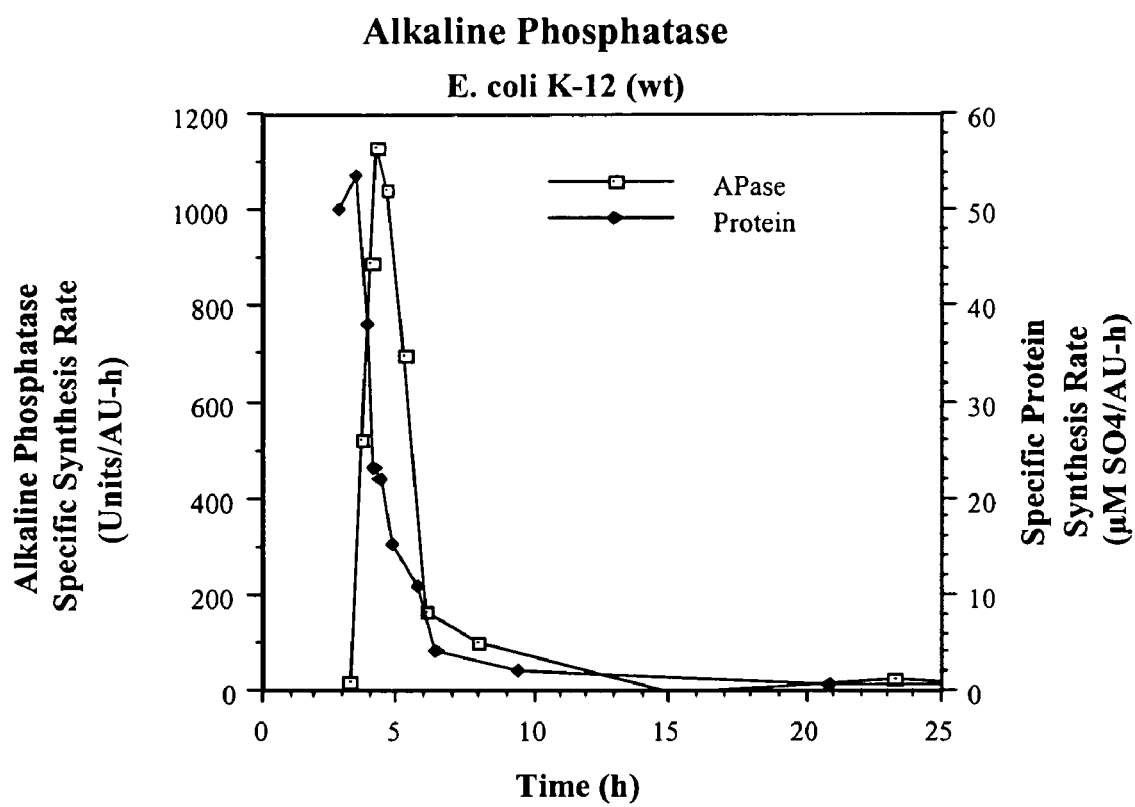
FIG. 27 shows alkaline phosphatase (PhoA) and total protein synthesis rates shown by *E. coli* before and during phosphate starvation. The onset of phosphate starvation occurs just after three hours.
Figure 28:
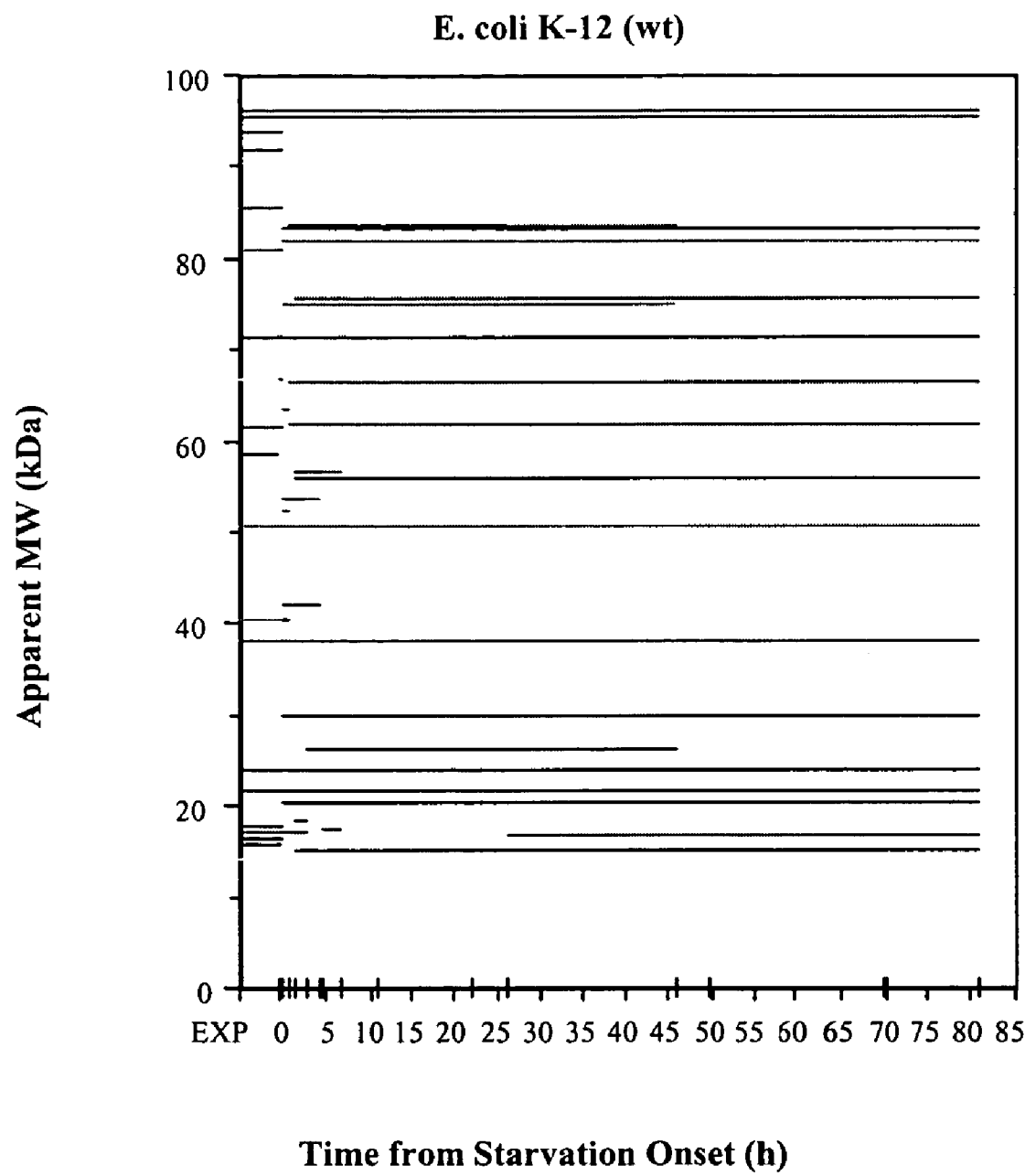
FIG. 28 shows the temporal expression of 53 proteins differentially expressed between exponential growth (EXP) and during phosphate starvation in *E. coli*.
Figure 29:
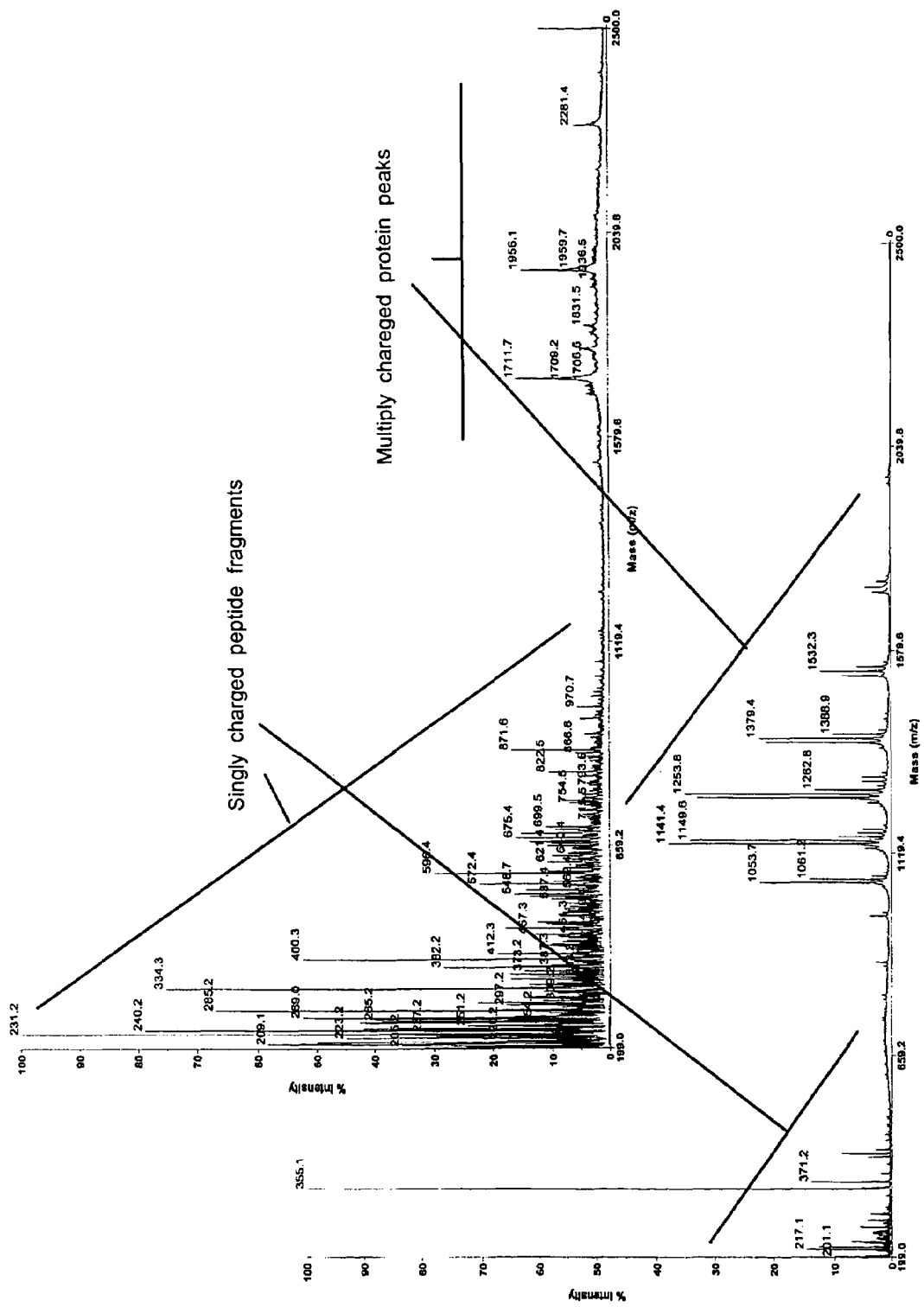
FIG. 29 shows variation in the efficiency of MS induced fragmentation of bovine ribonuclease A in the ionization zone of an ESI-TOF instrument as a function of 20 the nozzle voltage (270 V in the top and 150 V in the bottom spectra, respectively).

The identity of the parent 2-AETA-labeled bradykinin was determined at the minimally fragmenting 50-V spectrum based on the calculated mass for the expected reaction product. The C-terminal sequence of bradykinin was determined by inspecting the resulting mass spectra to determine the relative abundance of the possible 2-AETA-labeled peptide fragments at each nozzle potential. Peak counts corresponding to the entire possible series of $y^{+2}$ ions (FIG. 21) generated from the 2-AETA-labeled peptide fragment masses were clearly observed to increase in relative abundance with increasing nozzle potential with a maximum fragmentation abundance in the region of 150–200 V. With this label, which carries a fixed positive charge, no singly-charged y ions were observed since the C-terminal residue of bradykinin is arginine. Those mass fragments showing an increased abundance in the range of 150–200 V nozzle potential correspond to the published C-terminal sequence for bradykinin.

Example 11

This example illustrates the utility of inverted mass ladder sequencing for the identification of the protein glycogen phosphorylase a by searching a genomics database for matching protein sequence tags (PST) and limiting that search based on the position of the PST in the protein sequence.

The deduced N-terminal amino acid sequence of glycogen phosphorylase A from Example 1 (i.e., SRPLSD (SEO ID NO:2)) was used to search the SWIS-PROT and TrEMBEL protein sequence databases using the published ExPASy TagIdent tool (see, http://www.expasy.ch/tools/tagident.html). This tool enables searching known protein sequences contained within the database for any that contain matching sequences to a 1–6 contiguous amino acid PST. The search can be limited by the position of the PST in the protein (i.e., N-terminal or C-terminal) and the use of the electrophoretic coordinates isoelectric point and/or apparent molecular weight.

The search was limited to the 490 rabbit protein sequences contained within the database at the time. The number of matching proteins ("hits") were found to decrease with increasing PST length (Table 2). The number of hits at any given PST length could be further reduced by limiting the search further to N-terminal matches (Table 2). The number of hits at any given PST length are also reduced (Table 2) by including the apparent MW of the protein (100+/−20 kDa), determined from a capillary gel electrophoretic separation.

TABLE 2

Glycogen Phosphorylase Identification from a Genomic Database using an N-terminal IMLS PST

| PST | Number of hits based on PST | Number of N-terminal hits | Number of N-terminal hits limited by MW |
|---|---|---|---|
| S | 478 | 22 | 1 |
| SR | 299 | 1 | 1 |
| SRP | 1 | 1 | 1 |

Example 12

This example illustrates the utility of inverted mass ladder sequencing for the identification of the human peptide Bradykinin by searching a genomics database for matching protein sequence tags (PST) and limiting that search based on the position of the PST in the protein sequence and separation coordinates.

The deduced N-terminal amino acid sequence of bradykinin determined from Examples 2 and 3 (i.e., RPPGFS (SEQ ID NO:5)) was used to search the SWIS-PROT and TrEMBEL protein sequence databases as described in Example 6.

The search was limited to the 7171 human protein sequences contained within the database at the time. The number of matching proteins ("hits") were found to decrease with increasing PST length (Table 3). The number of hits at any given PST length could be further reduced by limiting the search further to N-terminal matches (Table 3). The number of hits at any given PST length were also reduced (Table 3) by including the apparent MW of the peptide (1000+/−200 Da), determined from the zero charge mass of the parent peptide in an ESI-TOF MS.

TABLE 3

Human Bradykinin Identification from a Genomic Database using an N-terminal IMLS PST

| PST | Number of hits based on PST | Number of N-terminal hits | Number of N-terminal hits limited by MW |
|---|---|---|---|
| RP | 4114 | 13 | 1 |
| RPP | 638 | 4 | 1 |
| RPPG | 66 | 1 | 1 |
| RPPGF | 5 | 1 | 1 |
| RPPGFS | 3 | 1 | 1 |

Example 13

This example illustrates the utility of inverted mass ladder sequencing for the identification of the horse apomyoglobin protein by searching a genomics database for matching protein sequence tags (PST) and limiting that search based on the position of the PST in the protein sequence and separation coordinates of the protein.

The deduced N-terminal amino acid sequence of apomyoglobin was determined from Example 4 (i.e., GLS) was used to search the SWIS-PROT and TrEMBEL protein sequence databases as described in Example 6.

The search was limited to the 241 horse protein sequences contained within the database at the time. The number of matching proteins ("hits") were found to decrease with increasing PST length (Table 4). The number of hits at any given PST length could be further reduced by limiting the search further to N-terminal matches (Table 4). The number of hits at any given PST length were also reduced (Table 4) by including the apparent MW of the protein (17+/−3.4 kDa), determined from the zero charge mass of the parent protein in an ESI-TOF MS, and the isoelectric point of the protein (pI=7+/−0.5) determined by capillary isoelectric focusing.

TABLE 4

Horse Apomyoglobin Identification from a Genomic Database using an N-terminal IMLS PST

| PST | Number of hits based on PST | Number of N-terminal hits | Number of N-terminal hits limited by MW | Number of N-terminal hits Limited by pI and MW |
|---|---|---|---|---|
| G | 235 | 10 | 5 | 1 |
| GL | 148 | 2 | 1 | 1 |
| GLS | 29 | 1 | 1 | 1 |

Example 14

Appropriate label chemistries for both maximum fluorescent detectability and suitability for mass spectrometer sequence analysis are determined by labeling purified proteins of known concentrations and sequences with alternative label chemistries and testing them in both CE and mass spectrometer analyses. At least three different proteins, or synthetically prepared peptides, are selected for evaluation in this task. Two proteins exhibit cross reactivity to the N- or C-terminal label chemistries used and one does not. Up to 30 alternative labels that have theoretically suitable constituents are commercially available. Samples of each protein are prepared and analyzed for their CE detectability and electrospray mass spectrometer signatures. A second round of up to five optimized alternative label chemistries are synthesized and analyzed based on the results obtained from the commercially-available labels. The best label is then selected for use in the remaining tasks.

Example 15

2-D CE Method

While CIEF, CZE, and CPAGE techniques have been developed and described previously, no previous reference has been made to the coupling these techniques to create a two dimensional CE method. This example shows that CIEF can be combined with CPAGE or CZE to reproducibly and quantitatively resolve complex mixtures of individual proteins. Mixtures of purified proteins of known concentrations and sequences are prepared as in Example 12. These protein mixtures are labeled with the label from Example 12 and run first through the CIEF method with fraction collection. The collected CIEF fractions are subsequently run through CPAGE or CZE methods to further resolve the proteins. At least 25 replicate experiments in which the concentrations of the individual proteins in the mixture are varied up to 1000 fold relative to one another are run to establish the coefficient of variation of the 2-D CE method. Finally, at least five replicate experiments are conducted with different protein loadings to determine the effect of column loading on the elution times and apparent isoelectric points.

Example 16

The mass spectrometer fragmentation pattern and efficiency of proteins can be significantly effected by the buffer solution in which the protein resides during the ionization step. Typical CE buffers are not the same buffers normally used for protein sequencing by MS. Fractions of the individual proteins eluted from the second dimension of the CE are collected and used to optimize the mass spectrometer method for the elution buffers used. Both electrospray and MALDI MS techniques are compared. The samples are evaluated for detection sensitivity, fragmentation efficiency, and maximum length of the protein sequence that can be discerned. The best MS method and conditions are selected and used for all further work.

Example 17

Use of the CE Plus MS Methods

In this example, the CE and MS methods from Examples 13 and 14 above are combined into a representative proteomics system. This system can be constructed of commercially available components. The suitability of the system for e.g., stress gene analysis (see below) is demonstrated by performing a proteomics analysis of a known stress gene response, such as the pho response of *E. coli*. To verify the performance of the system *E. coli* cultures are prepared from appropriate American Type Culture Collection stocks and subjected to phosphate starvation. The cellular proteins are extracted from exponentially growing culture samples and compared to phosphate starved samples using the system. The results obtained from the system are be compared to those described in the literature. See, e.g., L. V. Schneider, "Metabolic uncoupling in *Escherichia coli* during phosphate-limited growth," Ph.D. Thesis, Princeton University (1997). The protein expression pattern resulting from the 2-D CE method is converted into an image that is directly compared to classic 2-D gel electrophoresis results. Since the gene sequences on all the pho genes are published, it is possible to compare the accuracy of the protein sequence tags determined from this analysis to the known sequences.

Example 18

Use of Proteomics for Distinguishing Between Healthy and Cancerous Tissue

This example illustrates the use of the present invention for distinguishing between healthy and cancerous tissue. In particular, the present invention may be used to directly analyze the protein expression pattern of healthy and cancerous prostate and metastasized tissues to elucidate patterns of gene expression and translation that relate to the various aspects of onset, staging and metastases in prostate cancer. Such a proteomics investigation greatly speeds the genomic and functional genomics analyses of the mechanism of disease and quickly leads to the identification of new therapeutic targets, diagnostic markers, and drug products (i.e., where a specific cellular protein may itself act as a therapeutic agent). By using proteomic analysis the number of genes that must be investigated is reduced 10-fold (from the 50,000 to 35 100,00 human genes to the 2,000–5,000 actually being expressed in the target tissue). Through quantitative comparison of the protein expression pattern of healthy and diseased tissue, the number of candidate genes that may play roles in the progression of the disease is further reduced about 100-fold. Finally, through the generation of protein sequence tags (PSTs) these proteins can be uniquely identified in a manner that allows them to be tracked back to the genome for complete sequencing (e.g., mutation detection).

The method also allows for cDNA capture for more exhaustive molecular biological investigation of the mechanistic role in the disease (e.g., knock-in and knock-out studies in model organisms). It is at the protein level that virtually all cellular metabolism and cell signaling occurs. Proteomics is used to detect genetic mutations that result either in premature termination of the gene transcript or in amino acid substitutions in the resulting gene product. These appear as molecular weight changes or isoelectric point changes in the resulting protein. Because direct changes in the gene product are observed, inconsequential genetic variations (e.g., polymorphisms) are ignored. In this way, proteomic analysis can quickly identify genetic mutations that give rise to cancerous cells. Changes in the expression level of individual proteins can be caused by changes in gene expression. These changes can be tracked by functional genomics methods, but can also be caused by changes in translational efficiency and degradation, which can only be identified using proteomic analysis. The levels of certain proteins may also be a cause of cancer. For example, variations in G-proteins (membrane receptors), which are responsible for translating extracellular signals (such as hormone levels) into cellular responses might lead to cancer, if the cell interprets the corresponding signal change as a call to proliferate. Changes in metabolic proteins may cause an increase in cellular metabolism that leads to growth and cancer. Through proteomics, protein levels between healthy and tumor cells are directly compared, irrespective of the reason for the level changes. Another possible cause of cancer is the failure of post-translational protein modification, which could cause loss of a key signal transduction system leading to uncontrolled cell proliferation. Again, this only occurs after translation and can not be detected by genomic or functional genomic analyses. Natural defensin proteins, which fight tumor growth, may also be rendered nonfunctional with a failure in post-translational modification or increases in degradation rates. Proteomic analysis helps reveal the absence of natural defensins that may be used as drugs or gene therapy agents against disease. In these ways, proteomic analysis is an adjunct to genomic and functional genomic analyses of disease and speeds the identification of both the route causes of the disease and targets for drug discovery.

Proteomic analysis also allows for the identification of diagnostic markers (e.g., cell surface antigens or serum proteins) for immunodiagnostic assays. Purified samples of putative diagnostic proteins are recovered during proteomic analysis, allowing antibodies to be raised. These antibodies are used to further research the link between the diagnostic protein and the disease through immunohistological staining to localize the protein in the cell or to rapidly screen patient populations for the presence of the protein, showing its statistical link to the disease. It also provides an improved screening test.

In the United States, the incidence rate of prostate cancer is 23 per 100,000 among all males younger than 65 and 884 per 100,000 among men older than 65. In addition to older age, other risk factors for this cancer include a suspected familial association, high saturated fat intake (Omega-3 fatty acids are thought to reduce risk), history of venereal disease, multiple sex partners, vasectomy, and exposure to nitrate fertilizers (farmers/farm workers) and ferrochromium. Like all cancers, these risk factors suggest multiple causative factors may be involved. For example, the familial association suggests genetic predilection, probably related to genetic mutations. The relationship to dietary factors suggests metabolic roots or chemically induced genetic damage. The relationship to venereal disease and multiple sex partners suggests infectious agents (e.g., viral causes) or infection-compromised loss of natural tumor defenses. All of these putative disease mechanisms can be addressed through proteomic analysis. Early prostate cancer is usually asymptomatic and can only be detected by routine screening. The screening modality most often used is digital rectal examination. However, results of recent prostate screening studies have indicated that digital rectal examinations lack adequate sensitivity with approximately two-thirds of patients with malignant tumors having palpable indurations. Prostate-specific antigen (PSA) level screening is a sensitive measure of early-stage prostate cancer, but is considered to have poor specificity because elevated levels exist in patients with benign prostatic hyperplasia (BHP), prostatitis, or physical injury to the prostate. The recently developed tumor-associated antigen (TAA) marker assay appears to be a promising adjunct to PSA screening. Nevertheless, the widespread use of PSA as a screening tool is still controversial, in part because early detection of prostate cancer has not been proven in prospective, well-controlled studies to lead to improved patient outcomes in terms of mortality and morbidity. A more definitive screening test is sorely needed.

Prostate cancer is generally characterized by 4 clinical stages with few clinical management options. Early stage (Stage A) can be monitored for growth with no treatment; treated with radiation therapy, or removed (radical prostatectomy). Stage B prostate cancer (definitive but confined cancer) is automatically treated by radiation therapy or removal within the first 8 months of diagnosis. Stage C prostate cancer (spreading but still confined to the organ) is instantly treated with combined removal and radiation therapy or with palliative radiation therapy combined with hormonal therapy. Stage D pro-state cancer (metastasized) requires the most radical therapy including transurethral resection of the prostate, combined radiation therapy, palliative radiation therapy and hormonal therapy. Bone scans are also conducted at Stage D. Successful clinical outcomes diminish substantially with each stage of the disease. Aside from improvements in early detection, diagnostics that allow improved clinical management by guiding the choice of therapy or improving the oncologist's ability to properly stage the progress of the cancer could also improve clinical outcomes. While a number of anticancer drugs are in clinical trials for prostate cancer, the only recourse today is to remove or kill the tumor tissue. Identifying the mechanism(s) of prostate cancer and its metastasis should speed the development of better drug therapies.

Thus, proteomic analysis of healthy and cancerous prostate tissues and prostate cancer metastases are conducted. Proteomic database are built based on this analysis and the expression levels of all prostate proteins are quantified by their isoelectric point, molecular weight. Relative expression levels are determined directly from the native tissue samples. Isotopically labeled samples for quantitative analysis of protein expression levels are not required. Therefore, normal biopsy or autopsy samples can be used for all analyses performed. Protein sequence tags are determined for all proteins that show altered expression patterns between healthy and cancerous prostate tissue. Model proteins are used to evaluate the relative efficiency of alternative protein sequencing technologies. 2-D capillary electrophoresis (CE) of healthy tissue samples is used to develop conditions for the 2-D CE of prostate tissue samples. By using healthy tissue samples in this development, we simultaneously generate a baseline proteomics database. Replicate experiments are performed with prostate tissue samples taken from up to different people to assess natural variations in protein expression. At least 2 replicate experiments are performed with each tissue sample to assess the experimental variation in protein expression levels. Stage D prostate cancer exhibits the greatest variation in protein expression from healthy tissue. Therefore, 2-D CE conditions developed above are applied to up to 5 excised Stage D prostate tumor samples. Best results are expected with samples taken from individuals of similar age and ethnic backgrounds as the healthy tissue samples. PSTs for each protein that either appears or disappears in the 2-D CE pattern developed above are developed upon comparison of the 2-D electrophoresis patterns of healthy tissues. We assume that only 10 proteins will be completely absent in one of the two expression patterns, indicating a change in gene 5 sequence, expression, or post-translational modification. These proteins are believed to be the most likely to be related to the onset or metastasis of prostate cancer. PST determinations will be extended to proteins that exhibit expression levels significantly outside (i.e., 3 standard deviations) the natural variation determined in for normal tissues. We assume that some proteins will exhibit significant expression level changes. These proteins are the next most likely to be related to prostate cancer. A prostate cancer proteomic database is developed with the information generated from above. This database includes the isoelectric point, molecular weight, relative expression level and protein sequence tag (if determined) for each protein identified.

The experiment described above also provides a basic set of data on the underlying common mechanisms of prostate cancer. This data can be used to trace familial cancers, investigate proteomic variations associated with the cancer stages and metastases in other tissues, and investigate the function of tumor suspect targets that may be related to developmental proteins associated with puberty. Additionally, proteins associated with the attachment of metastases in other body tissues may be discovered and plasma protein markers of prostate cancer or its various stages may be identified. Furthermore, proteomic effects of various drug therapies from preclinical or clinical trials can be screened to help determine the mechanism of action and efficacy of the drug.

Example 19

Use of Proteomics for Analysis of Stress Gene Expression

With proteomics, stress gene expression can be used to fingerprint the chemical or biological agents known to cause a response in tissue-based biosensors. The superior sensitivity of tissue-based detection systems is due to the biochemical amplification cascades inherent in biological sensing. This receptor-based biochemical amplification approach, which is inherent in all biological sensing (from bacteria to man), holds the potential to leap-frog the two major limitations of conventional chemical detection systems: threshold sensitivity and the fingerprinting of threats. Known threats can be identified by matching the biochemical signature produced by the tissue upon exposure to the threat agent to a library of known biochemical signatures. One class of biochemical amplification systems is the stress gene system. The advantage of using stress gene signatures in fingerprinting is that novel and unknown threats can be identified based on the type of toxic effect they have on the tissue.

This example demonstrates a new proteomics method for rapidly identifying (to the gene sequence level) and quantifying stress gene expression. Stress gene fingerprints are identified for chemical agents and biological agents known to trigger the tissue-based biosensor. A library of stress gene fingerprints can created for every chemical and biological threat and the library used to rapidly fingerprint threats in the field once a tissue-based sensor is triggered. The proteomics technique is universally applicable to any tissue or cell type.

The foregoing process is repeated with multiple samples from diseased and control subjects, as well as replicate runs with samples from the same subjects. The results are then examined to identify proteins whose relative abundance varies between diseased and control subjects. Such proteins are potential markers for the particular disease and/or a drug target or potential drug.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

References

1. Kilár, F., "Isoelectric focusing in capillaries," in: CRC Handbook of Capillary Electrophoresis: A Practical Approach, Chp. 4, pgs. 95–109 (CRC Press, Boca Raton, Fla., 1994).
2. Palmieri, R. and J. A. Nolan, "Protein capillary electrophoresis: Theoretical and experimental considerations for methods development," in: CRC Handbook of Capillary Electrophoresis: A Practical Approach, Chp. 13, pgs. 325–368 (CRC Press, Boca Raton, 1994).
3. Wanders, B. J. and F. M. Everaerts, "Isotachophoresis in capillary electrophoresis," in: CRC Handbook of Capillary Electrophoresis: A Practical Approach, Chp. 5, pgs. 111–127 (CRC Press, Boca Raton, Fla., 1994).
4. Anderson, L. and J. Seilhamer, "A Comparison of Selected mRNA and Protein Abundances in Human Liver," *Electrophoresis,* 18:533 (1997).
5. Hochstrasser, D. F., et al., *Anal Biochem.,* 173:424(1988).
6. O'Farrell, P. H., *J Biol. Chem.,* 250:4007 (1975).
7. Anderson, N. G. and N. L. Anderson, "Twenty years of two-dimensional electrophoresis: Past, present and future," *Electrophoresis,* 17:443 (1996).
8. Lopez, M. F., "2D Electrophoresis of Target Protein Groups and the Initiation of a Neurological Disease Database," paper presented at the IBC Proteomics conference, Coronado, Calif. (Jun. 11–12, 1998).
9. Gottlieb, M. and M. Chavko, *Anal. Biochem.,* 165:33 (1987).

10. Bio-Rad, "Detection of Proteins in SDS-PAGE: A comparison of gel staining methods," EG Bulletin 1820, Rev B (Bio-Rad Laboratories, Hercules, Calif., 1996).
11. Schneider, L., "Metabolic uncoupling in *Escherichia coli* during phosphate limited growth," PhD Thesis, Department of Chemical Engineering, (Princeton University, Princeton, N.J., 1997).
12. Merril, C. R., *Methods in Enzymology*, 182:477 (1990).
13. Wilson, C. M., *Methods in Enzymology*, 91:236 (1983).
14. Lee, C., A. Levin and D. Branton, *Anal. Biochem.*, 166:308 (1987).
15. Dzandu, J. K., J. F. Johnson and G. E. Wise, *Anal. Biochem.*, 174:157 (1988).
16. Steinberg, Jones, Haugland and Singer, *Anal. Biochem.*, 239:223 (1996).
17. Merril, C. R., N. Arold, D. Taube and W. Ehrhardt, *Electrophoresis*, 9:255 (1981).
18. Garfin, D. E., *Methods in Enzymology*, 182:425 (1990).
19. Laermrli, U. K., *Nature*, 227:680 (1970).
20. Corthals, G. L., M. P. Molloy, B. R. Herbert, K. L. Williams, and A. A. Gooley, "Prefractionation of protein samples prior to two-dimensional electrophoresis," *Electrophoresis*, 18:317 (1997).
21. Lopez, M. F., and W. F. Patton, "Reproducibility of polypeptide spot positions in two-dimensional electrophoresis of ribosomal and nuclear proteins," *Electrophoresis*, 18:338 (1997).
22. McKee, A., "The Yeast Proteome," paper presented at the IBC Proteomics conference, Coronado, Calif. (Jun. 11–12, 1998).
23. Anderson, L., "Pharmaceutical Proteomics: Targets, mechanisms and function," paper presented at the IBC Proteomics conference, Coronado, Calif. (Jun. 11–12, 1998).
24. Parekh, R. B., "Use of Proteomics in pre-clinical pharmaceutical research," paper presented at the IBC Proteomics conference, Coronado, Calif. (Jun. 11–12, 1998).
25. BioRad Molecular Imager FX and PDQuest 2-D analysis software seminar, presented at the IBC Proteomics conference, Coronado, Calif. (Jun. 11–12, 1998).
26. Patton, W. F., "Defining protein targets for drug discovery using Proteomics," paper presented at the IBC Proteomics conference, Coronado, Calif. (Jun. 11–12, 1998).
27. Ramsby, M., G. Makowski, and E. Khairallah, "Differential detergent fractionation of isolated hepatocytes: Biochemical, immunochemical, and two-dimensional gel electrophoresis characterization of cytoskeletal and non-cytoskeletal compartments," *Electrophoresis*, 15:265 (1994).
28. Blomber, A., L. Biomberg, J. Norbeck, S. J. Fey, P. Mose-Larsen, M. Larsen, P. Roepstorff, H. Degand, M. Boutry, A. Posch and A. Görg, *Electrophoresis*, 16:1935 (1995).
29. Corbett, J. M., M. J. Dunn, A. Posch and A. Görg, *Electrophoresis*, 15:1205 (1994).
30. Beckman Instruments, "eCAP SDS 200: Fast, reproducible, quantitative protein 30 analysis," BR2511B (Beckman Instruments, Fullerton, Calif., 1993).
31. Anderson, N. L. et al., "An updated two-dimensional gel database of rat liver proteins useful in gene regulation and drug effects studies," *Electrophoresis*, 16:1997 (1995).
32. Franzén, F., S. Linder, A.A. Alaiya, E. Eriksson, K. Fujioka, A.-C. Bergman, H. Jörnvall, G. Auer, "Analysis of polypeptide expression in benign and malignant human breast lesions," *Electrophoresis*, 18:582 (1997).
33. Guttmnan, A., J. A. Nolan and N. Cooke, "Capillary sodium dodecyl sulfate gel electrophoresis of proteins, *J. Chromatogr.*, 632:171 (1993).
34. Clauser, K. R., "Managing high-throughput data acquisition and analysis in LC/MS/MS-based Proteomics," paper presented at the IBC Proteomics conference, Coronado, Calif. (Jun, 11–12, 1998).
35. P/ACE™ Laser-induced fluorescence Detectors, BR-8118A (13eckman Instruments, Fullerton, Calif., 1995).
36. Wilm, M. and Mann, M., "Analytical properties of the nanoelectrospray ion source," *Anal. Chem.*, 68:1–8 (1996).
37. Steiner, S., "Proteome methods to profile mechanisms of toxicity," paper presented at the IBC Proteomics conference, Coronado, Calif. (Jun. 11–12, 1998).
38. Arnott, D., "Protein differential display and mass spectrometry in the study of congestive heart failure," paper presented at the IBC Proteomics conference, Coronado, Calif. (Jun. 11–12, 1998).
39. Witzmann, F. A., C. D. Flutz, and J. F. Wyman, "Two-dimensional electrophoresis of precision-cut testis slices: Toxicologic application," *Electrophoresis*, 18:642 (1997).
40. Hjertén, S., J.-L. Liao and K. Yao, "Theoretical and experimental study of high-performance electrophoretic mobilization of isoelectrically focused protein zones, *J. Chromatogr.*, 387:127 (1987).
41. Kim, K. W., *J. Chromatogr.*, 559:401 (1991).
42. Satow, T. et al., "The effecto of salts on the separation of bioactive peptides by capillary electrophoresis," *J. High Resolut. Chromatogr.*, 14:276 (1991).
43. Shihabi, Z. K. and L. L. Garcia, "Effects of sample matrix on separation by capillary electrophoresis," in: CRC Handbook of Capillary Electrophoresis: A Practical Approach, Chp. 20, pgs. 537–548 (CRC Press, Boca Raton, Fla., 1994).
44. Garfin, D. E., *Methods in Enzymology*, 182:425 (1990).
45. Jorgenson, J. W. and K. D. Lukacs, "Zone electrophoresis in open-tubular glass capillaries: preliminary data on performance," *J. High Resolut. Chromnatogr. Commun.*, 4:230 (1981).
46. Jorgenson, J. W., and K. D. Lukacs, "Zone electrophoresis in open tubular capillaries," *Anal. Chem.*, 53:1298 (1981).
47. Mc Cormick, R. M., "Capillary zone electrophoresis of peptides," in: CRC Handbook of Capillary Electrophoresis: A Practical Approach, Chp. 12, pgs. 287–323 (CRC Press, Boca Raton, Fla., 1994).
48. Aebersold, R., "Proteome analysis: Biological assay or data archive?," paper presented at the IBC Proteomics conference, Coronado, Calif. (Jun. 11–12, 1998).
49. Cobb, K. A. and M. Novotny, "High-sensitivity peptide mapping by capillary zone electrophoresis and microcoluin liquid chromatography, using immobilized trypsin for protein digestion, *Anal. Chem.*, 61:2226 (1989).
50. Cantor, C. R. and P. R. Schimmel, Biophysical Chemistry (W.H. Freeman & Co., N.Y., 1980).
51. Hjertén, S., "Free zone electrophoresis," *Chromatogr. Rev.*, 9:122 (1967).
52. Martinek, K., Goldmacher, V. S., Klibanov, A. M., and Berezin, I. V., "Denaturing agents (urea, acrylamide) protect enzymes against irreverisble thermoinactivation: A study with native and immobilized alpha-chymotrypsin and trypsin," *FEBS Lett.*, 51:152–155 (1975).
53. Altria, K. D. and C. F. Simpson, "Measurement of electroendosmosis in high-voltage capillary electrophoresis," *Anal. Proc.*, 23:453 (1986).

54. Camilleri, P. and G. N. Okafo, "Replacement of H2O by D2O in capillary zone electrophoresis can increase resolution of peptides and proteins, " *J. Chem. Soc. Chem. Commun.*, 3:196 (1991).
55. Camilleri, P., G. N. Okafo, C. Southan, and R. Brown, "Analytical and micropreparative capillary electrophoresis of the peptides from calcitonin," *Anal. Biochem.*, 198:36 (1991).
56. Okafo, G. N. and P. Camilleri, "Capillary electrophoretic separation in both H2O and [2H]2O-based electrolytes can provide more information on tryptic digests, *J. Chromatogr.*, 547:551 (1991).
57. Schwer, C. and F. Lottspeich, "Analytical and micropreparative separation of peptides by capillary zone electrophoresis using discontinuous buffer systems," J. Chromatogr., 623:345 (1992).
58. Foret, F., E. Szoko and B. L. Karger, "On-column transient and coupled column isotachophoretic preconcentration of protein samples in capillary zone electrophoresis," *J. Chromatogr.*, 608:3 (1992).
59. Lowry, O., N. Rosebrough, A. Farr and R. Randall, *J. Biol. Chem.*, 193:265–275 (1951).
60. Anderson, N. L., "Pharmaceutical Proteomics: Targets, mechanism, and finction," paper presented at the IBC Proteomics conference, Coronado, Calif. (Jun. 11–12, 1998).
61. Meng, C. K., M. Mann and J. B. Fenn, *Z. Phy. D: Atoms, Mol. Clusters*, 10:361–368 (1988).
62. Karas, M. and F. Hillenkamp, *Anal. Chem.* 60:2299 (1988).
63. Hillenkamp, F., M. Jaras, R. C. Beavis and B. T. Chait, *Anal. Chem.* 63:1193A (1991).
64. Beavis, R. C. and B. T. Chait, "Matrix-assisted laser desorption mass spectrometry of proteins," preprint, http://www.proteometrics.com/methods/contents.htm (1994).
65. Clauser, K. R., S. C. Hall, D. M. Smith, J. W. Webb, L. E. Andrews, H. M. Tran, L. B. Epstein, and A. L. Burlingame, *Proc. Natl. Acad. Sci (USA)*, 92:5072–5076 (1995).
66. Li, G., M. Walthan, N. L. Anderson, E. Unworth, A. Treston and J. N. Weinstein, "Rapid mass spectrometric identification of proteins from two-dimensional polyacrylamide gels after in gel proteolytic digestion," *Electrophoresis*, 18:391–402 (1997).
67. Stevens, F. J., "Method of electric field flow fractionation wherein the polarity of the electric field is periodically reversed," U.S. Pat. No. 5,133,844, (Jul. 28, 1992).
68. Gupta N. R., Nadim A., Haj-Hariri H., Borhan A., "Stability of the Shape of a Viscous Drop under Buoyancy-Driven Translation in a Hele-Shaw Cell, " *J Colloid Interface Sci*, 222(1):107–116 (2000).
69. Sanger, F., *Biochem. J.*, 39:507 (1945).
70. Creighton, T. E., *Proteins: Structures and Molecular Principles* (W.-H. Freeman, N.Y., 1984).
71. Niederwieser, A., "Thin-layer chromatography of amino acids and derivatives," in: *Methods in Enzymology*, 25:60–99 (1972).
72. Hirs, C. H. W., M. Halmann and J. H. Kycia, "Dinitrophenylation and inactivation of bovine pancreatic ribonuclease A," *Arch. Biochem. Biophys.*, 111:209–222 (1965).
73. Gray, W. R., "End-group analysis using dansyl chloride," in: *Methods in Enzymology*, 25:121–137 (1972).
74. Stark, G. R., "Use of cyanate for determining NH2-terminal residues in protein," in: *Methods in Enzymology*, 25:103–120 (1972).
75. Niall, H. D., "Automated Edman degradation: the protein sequenator," in: *Methods in Enzymology*, 27:942–1011 (1973).
76. Galella, G. and D. B. Smith, "The cross-linking of tubulin with imntnidoesters," *Can. J. Biochem.*, 60:71–80 (1982).
77. Lomant, A. J. and G. Fairbanks, "Chemical probes of extended biological structures: synthesis and properties of the cleavable protein crosslinking reagent 35S.dithiobis (succinirnidyl propionate), *J. Mol. Biol.*, 104:243–261 (1976).
78. Solomons, T. W. G, Organic Chemistry. (John Wiley & Sons, NY, 1976).
79. Novotny et al., *Anal. Chem.*, 63:408 (1991).
80. Novotny et al., *J. Chromatography*, 499:579 (1990).
81. Merrifield, B., *Science*, 232:341–347 (1986).
82. Horton, H. R. and D. E. Koshland, Jr., *Methods in Enzymology*, 25:468 (1972).
83. Yamada, H., Imoto, T., Fujita, K., Okazaki, K. and M. Motomura, "Selective modification of aspartic acid-101 in lysozyme by carbodiimide reaction," *Biochem.*, 20:4836–4842.
84. Grabarek, Z. and J. Gergely, "Zero-length crosslinking procedure with the use of active esters," *Anal. Biochem.* 185:131–135 (1990).

What is claimed is:

1. A method of generating from a sample a high-resolution protein expression fingerprint dataset containing a plurality of polypeptide sequence tags, comprising:
   (i) obtaining a protein-containing extract from said sample, wherein said sample comprises a plurality of intact proteins;
   (ii) electrophoresing said extract in a multidimensional capillary electrophoresis device having an electroosmotic flow of less than $1 \times 10^{-4}$ cm$^2$/V-s to separate and elute intact protein species to resolve said intact protein species based on at least one first biophysical parameter which discriminates protein species;
   (iii) obtaining, by mass spectrographic fragmentation of a plurality of eluted intact protein species, a plurality of polypeptide sequence tags; and
   (iv) generating a high-resolution protein expression fingerprint dataset containing said plurality of polypeptide sequence tags.

2. The method of claim 1, wherein the method further comprises, prior to step (iii):
   (iia) electrophoresing eluted intact protein species eluted from said multidimensional capillary electrophoresis device in a second capillary electrophoresis device, or plurality thereof in parallel, to separate and elute intact protein species thereby resolving said protein species based on at least one second biophysical parameter which discriminates protein species.

3. The method of claim 1, further comprising quantitating said plurality of eluted intact protein species, thereby including the relative abundance of said plurality of eluted intact protein species in said high-resolution protein expression fingerprint dataset.

4. The method of claim 1, further comprising storing said high-resolution protein expression fingerprint dataset in computer-retrievable form.

5. The method of claim 1, wherein said plurality of eluted intact protein species is at least 100 eluted intact protein species.

6. The method of claim 5, further comprising quantitating said at least 100 eluted intact protein species, thereby including the relative abundance of said at least 100 eluted intact protein species in said high-resolution protein expression fingerprint dataset.

7. The method of claim 1, further comprising determining the separation coordinates of said plurality of eluted intact protein species, thereby including the separation coordinates of said plurality of eluted intact protein species in said high-resolution protein expression fingerprint dataset.

8. The method of claim 1, wherein said sample is a tissue sample known to be free of pathological disorders.

9. The method of claim 1, wherein said sample is a tissue sample known to contain at least one pathological disorder.

* * * * *

UNITED STATES PATENT AND TRADEMARK OFFICE
CERTIFICATE OF CORRECTION

PATENT NO.         : 7,211,376 B2
APPLICATION NO. : 10/721047
DATED                  : November 21, 2003
INVENTOR(S)       : Schneider et al.

It is certified that error appears in the above-identified patent and that said Letters Patent is hereby corrected as shown below:

In col. 10, line 14, replace "carlalso" with --can also--.

In col. 16, line 14, replace "bya" with --by a--.

In col. 17, line 32, replace "electropherograin" with --electropherogram--.

In col. 18, line 9, replace "1MB" with --IBM--.

In col. 19, line 10, replace the hyphen before the open parenthesis with a space.

In col. 19, line 39, there seems to be missing text in the sentence beginning "The of the amino acids....".

In col. 19, line 49, replace "-disubstituted" with --disubstituted-- (the word without the hyphen).

In col. 25, line 62, replace "in-he" with --in the--.

In col. 25, line 62, replace "farther" with --further--.

In col. 27, line 39, replace "spacially" with --spatially--.

In col. 27, line 43, replace "spacially" with --spatially--.

In col. 28, line 2, replace "invention-includes" with --invention includes-- (remove hyphen).

In col. 30, line 43, replace "spacially" with --spatially--.

In col. 32, line 36, replace "ampholyte-gradient" with --ampholyte gradient-- (remove hyphen).

In col. 33, line 16, replace "("BRIJ"721)" with --("BRIJ" 721)--.

In col. 35, line 67, replace "the." with --the--.

In col. 38, line 43, remove the space after "21".

UNITED STATES PATENT AND TRADEMARK OFFICE
CERTIFICATE OF CORRECTION

PATENT NO.         : 7,211,376 B2
APPLICATION NO. : 10/721047
DATED                 : November 21, 2003
INVENTOR(S)       : Schneider et al.

It is certified that error appears in the above-identified patent and that said Letters Patent is hereby corrected as shown below:

In col. 39, line 22, replace "EACalif" with --EACA--.

In col. 39, line 24, replace "EACalif" with --EACA--.

In col. 41, line 3, remove the hyphen after "completion".

In col. 45, line 1, replace "anmnonium" with --ammonium--.

In col. 46, line 62, replace "I min" with --1 min--.

In col. 48, line 32, insert a period after "tag".

In col. 51, line 10, replace "carboduimides" with --carbodiimides--.

In col. 52, line 25, insert a space after "(4)".

In col. 56, lines 3, replace "orutan-" with --or tan--.

In col. 56, line 40, replace "m-ore" with --more--.

In col. 57, line 46, replace "Hom" with --Horn--.

In col. 58, lines 1-2, remove the space between "T" and "M".

In col. 58, line 62, replace the hyphen after "and" with a space.

In col. 61, line 2, replace "ab" with --above--.

In col. 62, line 27, replace "identies" with --identities--.

In col. 64, line 40, replace "Becklman" with --Beckman--.

In col. 67, line 35, replace "10/%" with --1%--.

In col. 69, line 54, replace "SEO" with --SEQ--.

In col. 69, line 57, replace "TagIdent" with --TagIdent--.

UNITED STATES PATENT AND TRADEMARK OFFICE
CERTIFICATE OF CORRECTION

PATENT NO. : 7,211,376 B2
APPLICATION NO. : 10/721047
DATED : November 21, 2003
INVENTOR(S) : Schneider et al.

It is certified that error appears in the above-identified patent and that said Letters Patent is hereby corrected as shown below:

In col. 70, line 55, after "RPPG" insert --(SEQ ID NO:3)--.

In col. 70, line 56, after "RPPGF" insert --(SEQ ID NO:4)--.

In col. 70, line 57, after "RPPGFS" insert --(SEQ ID NO:5)--.

In col. 79, line 24, replace "finction" with --function--.

In col. 80, line 8, replace the hyphen before "H." with a space.

In col. 80, line 26, replace "imntnidoesters" with --immidoesters--.

In col. 80, line 32, replace "succinirnidyl" with --succinimidyl--.

Signed and Sealed this

Third Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,211,376 B2
APPLICATION NO. : 10/721047
DATED : May 1, 2007
INVENTOR(S) : Schneider et al.

It is certified that error appears in the above-identified patent and that said Letters Patent is hereby corrected as shown below:

In col. 10, line 14, replace "carlalso" with --can also--.

In col. 16, line 14, replace "bya" with --by a--.

In col. 17, line 32, replace "electropherograin" with --electropherogram--.

In col. 18, line 9, replace "1MB" with --IBM--.

In col. 19, line 10, replace the hyphen before the open parenthesis with a space.

In col. 19, line 39, there seems to be missing text in the sentence beginning "The of the amino acids....".

In col. 19, line 49, replace "-disubstituted" with --disubstituted-- (the word without the hyphen).

In col. 25, line 62, replace "in-he" with --in the--.

In col. 25, line 62, replace "farther" with --further--.

In col. 27, line 39, replace "spacially" with --spatially--.

In col. 27, line 43, replace "spacially" with --spatially--.

In col. 28, line 2, replace "invention-includes" with --invention includes-- (remove hyphen).

In col. 30, line 43, replace "spacially" with --spatially--.

In col. 32, line 36, replace "ampholyte-gradient" with --ampholyte gradient-- (remove hyphen).

In col. 33, line 16, replace "("BRIJ"721)" with --("BRIJ" 721)--.

In col. 35, line 67, replace "the." with --the--.

In col. 38, line 43, remove the space after "21".

UNITED STATES PATENT AND TRADEMARK OFFICE
CERTIFICATE OF CORRECTION

PATENT NO.        : 7,211,376 B2
APPLICATION NO.   : 10/721047
DATED             : May 1, 2007
INVENTOR(S)       : Schneider et al.

It is certified that error appears in the above-identified patent and that said Letters Patent is hereby corrected as shown below:

In col. 39, line 22, replace "EACalif" with --EACA--.

In col. 39, line 24, replace "EACalif" with --EACA--.

In col. 41, line 3, remove the hyphen after "completion".

In col. 45, line 1, replace "anmnonium" with --ammonium--.

In col. 46, line 62, replace "I min" with --1 min--.

In col. 48, line 32, insert a period after "tag".

In col. 51, line 10, replace "carboduimides" with --carbodiimides--.

In col. 52, line 25, insert a space after "(4)".

In col. 56, lines 3, replace "orutan-" with --or tan--.

In col. 56, line 40, replace "m-ore" with --more--.

In col. 57, line 46, replace "Hom" with --Horn--.

In col. 58, lines 1-2, remove the space between "T" and "M".

In col. 58, line 62, replace the hyphen after "and" with a space.

In col. 61, line 2, replace "ab" with --above--.

In col. 62, line 27, replace "identies" with --identities--.

In col. 64, line 40, replace "Becklman" with --Beckman--.

In col. 67, line 35, replace "10/%" with --1%--.

In col. 69, line 54, replace "SEO" with --SEQ--.

In col. 69, line 57, replace "TagIdent" with --TagIdent--.

UNITED STATES PATENT AND TRADEMARK OFFICE
CERTIFICATE OF CORRECTION

PATENT NO. : 7,211,376 B2
APPLICATION NO. : 10/721047
DATED : May 1, 2007
INVENTOR(S) : Schneider et al.

It is certified that error appears in the above-identified patent and that said Letters Patent is hereby corrected as shown below:

In col. 70, line 55, after "RPPG" insert --(SEQ ID NO:3)--.

In col. 70, line 56, after "RPPGF" insert --(SEQ ID NO:4)--.

In col. 70, line 57, after "RPPGFS" insert --(SEQ ID NO:5)--.

In col. 79, line 24, replace "finction" with --function--.

In col. 80, line 8, replace the hyphen before "H." with a space.

In col. 80, line 26, replace "imntnidoesters" with --immidoesters--.

In col. 80, line 32, replace "succinirnidyl" with --succinimidyl--.

This certificate supersedes the Certificate of Correction issued June 3, 2008.

Signed and Sealed this

First Day of July, 2008

JON W. DUDAS
*Director of the United States Patent and Trademark Office*